US010793625B2

(12) United States Patent
Cao

(10) Patent No.: US 10,793,625 B2
(45) Date of Patent: Oct. 6, 2020

(54) COMPOSITIONS AND METHODS FOR TREATING OR PREVENTING OSTEOARTHRITIS

(71) Applicant: THE JOHNS HOPKINS UNIVERSITY, Baltimore, MD (US)

(72) Inventor: Xu Cao, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 226 days.

(21) Appl. No.: 14/397,933

(22) PCT Filed: May 1, 2013

(86) PCT No.: PCT/US2013/039076
§ 371 (c)(1),
(2) Date: Oct. 30, 2014

(87) PCT Pub. No.: WO2013/166156
PCT Pub. Date: Nov. 7, 2013

(65) Prior Publication Data
US 2015/0139909 A1 May 21, 2015

Related U.S. Application Data

(60) Provisional application No. 61/640,886, filed on May 1, 2012, provisional application No. 61/697,483, filed on Sep. 6, 2012.

(51) Int. Cl.
| *C07K 16/22* | (2006.01) |
| *A61K 31/4439* | (2006.01) |
| *A61K 31/663* | (2006.01) |
| *A61K 49/06* | (2006.01) |
| *A61K 39/00* | (2006.01) |

(52) U.S. Cl.
CPC .......... *C07K 16/22* (2013.01); *A61K 31/4439* (2013.01); *A61K 31/663* (2013.01); *A61K 49/06* (2013.01); *A61K 2039/505* (2013.01)

(58) Field of Classification Search
None
See application file for complete search history.

(56) References Cited

U.S. PATENT DOCUMENTS

2008/0177218 A1* 7/2008 McKay ............... A61B 17/56
604/19
2010/0150838 A1    7/2010 Ling

FOREIGN PATENT DOCUMENTS

WO    WO 2005010049 A2 *  2/2005  ............ C07K 16/22
WO         2013/166156 A2    7/2013

OTHER PUBLICATIONS

McErlain et al. An in vivo investigation of the initiation and progression of subchondral cysts in a rodent model of secondary osteoarthritis. 2012 Arthritis Res. Ther. 14: R26, 12 pages. Published Feb. 3, 2012.*
DaCosta Byfield et al. SB-505124 is a selective inhibitor of transforming growth factor-beta type I receptors ALK4, ALK5, and ALK7. 2004 Mol. Pharmacol. 65: 744-752.*
Uludag et al. Bisphosphonate conjugation to proteins as a means to impart bone affinity. 2000 Biotechnol. Prog. 16: 258-267.*
Ruzek et al. Minimal effects on immune parameters following chronic anti-TGF-beta monoclonal antibody administration to normal mice. 2003 Immunopharmacol. Immunotoxicol. 25: 235-257. (Year: 2003).*
Hoffman, Robert M. "The potential of nestin-expressing hair follicle stem cells in regenerative medicine." (Expert Opin Biol Ther. Mar. 2007;7(3):289-91.
Zhang, Ming, et al. "Smad3 prevents β-catenin degradation and facilitates β-catenin nuclear translocation in chondrocytes." Journal of Biological Chemistry 285.12 (2010): 8703-8710.
T. F. Li et al., Smad3-deficient chondrocytes have enhanced BMP signaling and accelerated differentiation. J Bone Miner Res 21, 4 (Jan. 2006).
Lohmander, L. Stefan, et al. "The long-term consequence of anterior cruciate ligament and meniscus injuries osteoarthritis." The American journal of sports medicine 35.10 (2007): 1756-1769.
Mankin, Henry J., et al. "Biochemical and metabolic abnormalities in articular cartilage from osteo-arthritic human hips." The Journal of Bone & Joint Surgery 53.3 (1971): 523-537.
Van der Sluijs, J. A., et al. "The reliability of the Mankin score for osteoarthritis." Journal of Orthopaedic Research 10.1 (1992): 58-61.
Burns, Kevin A., et al. "Developmental and post-injury cortical gliogenesis: A Genetic fate—mapping study with Nestin—CreER mice." Glia 57.10 (2009): 1115-1129.
Chytil, Anna, et al. "Conditional inactivation of the TGF-β type II receptor using Cre: Lox." Genesis 32.2 (2002): 73-75.
Jones, Michael D., et al. "In vivo microfocal computed tomography and micro-magnetic resonance imaging evaluation of antiresorptive and antiinflammatory drugs as preventive treatments of osteoarthritis in the rat." Arthritis & Rheumatism 62.9 (2010): 2726-2735.
Lee, Jonathan H., et al. "Subchondral fluid dynamics in a model of osteoarthritis: use of dynamic contrast-enhanced magnetic resonance imaging." Osteoarthritis and Cartilage 17.10 (2009): 1350-1355.
Wu, Xiangwei, et al. "Inhibition of Sca-1-positive skeletal stem cell recruitment by alendronate blunts the anabolic effects of parathyroid hormone on bone remodeling." Cell stem cell 7.5 (2010): 571-580.
M. D. Jones et al., In vivo microfocal computed tomography and micro-magnetic resonance imaging evaluation of antiresorptive and antiinflammatory drugs as preventive treatments of osteoarthritis in the rat. Arthritis and rheumatism 62, 2726 (Sep. 2010).

(Continued)

*Primary Examiner* — Jennifer Lamberski
(74) *Attorney, Agent, or Firm* — Casimir Jones, SC; Robert A. Goetz

(57) ABSTRACT

The present invention relates to the field of osteoarthritis. More specifically, the present invention provides compositions and methods useful for treating or preventing osteoarthritis. In one embodiment, a method for treating or preventing osteoarthritis in a patient comprises the step of administering to the patient a therapeutically effective amount of a transforming growth factor beta (TGF-beta) inhibitor.

7 Claims, 55 Drawing Sheets

Specification includes a Sequence Listing.

(56) References Cited

OTHER PUBLICATIONS

J. Yao et al., Deterioration of stress distribution due to tunnel creation in single-bundle and double-bundle anterior cruciate ligament reconstructions. Ann Biomed Eng (Feb. 1, 2012).

Frobell, R. B., et al. "Presence, location, type and size of denuded areas of subchondral bone in the knee as a function of radiographic stage of OA—data from the OA initiative." Osteoarthritis and Cartilage 18.5 (2010): 668-676.

Ding, Cicuttini, Flavia Cicuttini, and Graeme Jones. "Tibial subchondral bone size and knee cartilage defects: relevance to knee osteoarthritis." Osteoarthritis and cartilage 15.5 (2007): 479-486.

Doré, Dawn, et al. "Subchondral bone and cartilage damage: a prospective study in older adults." Arthritis & Rheumatism 62.7 (2010): 1967-1973.

Choi, K., et al. "The elastic moduli of human subchondral, trabecular, and cortical bone tissue and the size-dependency of cortical bone modulus." Journal of biomechanics 23.11 (1990): 1103-1113.

M. J. Douglas, J. D. Hutchison, A. G. Sutherland, Anterior cruciate ligament integrity in osteoarthritis of the knee in patients undergoing total knee replacement. Journal of orthopaedics and traumatology : official journal of the Italian Society of Orthopaedics and Traumatology 11, 149 (Sep. 2010).

C. H. Heldin, K. Miyazono, P. ten Dijke, TGF-beta signalling from cell membrane to nucleus through SMAD proteins. Nature 390, 465 (Dec. 4, 1997).

S. Koelling et al., Migratory chondrogenic progenitor cells from repair tissue during the later stages of human osteoarthritis. Cell stem cell 4, 324 (Apr. 3, 2009).

S. P. Grogan, S. Miyaki, H. Asahara, D. D. D'Lima, M. K. Lotz, Mesenchymal progenitor cell markers in human articular cartilage: normal distribution and changes in osteoarthritis. Arthritis research & therapy 11, R85 (2009).

M. C. Arufe, A. De la Fuente, I. Fuentes, F. J. de Toro, F. J. Blanco, Chondrogenic potential of subpopulations of cells expressing mesenchymal stem cell markers derived from human synovial membranes. Journal of cellular biochemistry 111, 834 (Nov. 1, 2010).

S. Y. Lee, T. Nakagawa, A. H. Reddi, Mesenchymal progenitor cells derived from synovium and infrapatellar fat pad as a source for superficial zone cartilage tissue engineering: analysis of superficial zone protein/lubricin expression. Tissue engineering. Part A 16, 317 (Jan. 2010).

D. J. Hunter et al., Bone marrow lesions from osteoarthritis knees are characterized by sclerotic bone that is less well mineralized. Arthritis research & therapy 11, R11 (2009).

F. Echtermeyer et al., Syndecan-4 regulates ADAMTS-5 activation and cartilage breakdown in osteoarthritis. Nature medicine 15, 1072 (Sep. 2009).

A. C. Lin et al., Modulating hedgehog signaling can attenuate the severity of osteoarthritis. Nature medicine 15, 1421 (Dec. 2009).

T. Saito et al., Transcriptional regulation of endochondral ossification by HIF-2alpha during skeletal growth and osteoarthritis development. Nature medicine 16, 678 (Jun. 2010).

S. S. Glasson et al., Deletion of active ADAMTS5 prevents cartilage degradation in a murine model of osteoarthritis. Nature 434, 644 (Mar. 31, 2005).

Qiu et al (2010) TGF-beta type II receptor phosphorylates PTH receptor to integrate bone remodelling signalling. Nat Cell Biol. Mar. 2010;12(3):224-34. doi: 10.1038/ncb2022. Epub Feb. 7, 2010.

Cao et al (2011) Targeting communication between osteoclast and osteoblast. Nature Medicine 17:1344-6.

Van der Kraan, P, Vitters, E, van den Berg, W. (1992). Differential effect of transforming growth factor beta on freshly isolated and cultured articular chondrocytes. The Journal of Rheumatology. 19(1):140-145, Abstract only provided.

Davidson, E.N., van der Kraan, P.M., van der Berg, WB. (2007). TGF-β and osteoarthritis. Osteoarthritis and Cartilage. vol. 15, Issue 6: 597-604.

Scharstuhl A, Glansbeek, H.L, van Beuningen, H.M., Vitters, E.L., van der Kraan, P.M., van der Berg, W.B. (2002). Inhibition of Endogenous TGF-During Experimental Osteoarthritis Prevents Osteophyte Formation and Impairs Cartilage Repair. The Journal of Immunology. 169: 507-514.

E. R. Sampson et al., Teriparatide as a chondroregenerative therapy for injury-induced osteoarthritis. Science translational medicine 3, 101ra93 (Sep. 21, 2011).

W. B. van den Berg, Osteoarthritis year 2010 in review: pathomechanisms. Osteoarthritis and cartilage / OARS, Osteoarthritis Research Society 19, 338 (Apr. 2011).

F. Berenbaum, Osteoarthritis year 2010 in review: pharmacological therapies. Osteoarthritis and cartilage / OARS, Osteoarthritis Research Society 19, 361 (Apr. 2011).

G. A. Hawker, S. Mian, K. Bednis, I. Stanaitis, Osteoarthritis year 2010 in review: nonpharmacologic therapy. Osteoarthritis and cartilage / OARS, Osteoarthritis Research Society 19, 366 (Apr. 2011).

R. J. Lories, F. P. Luyten, The bone-cartilage unit in osteoarthritis. Nature reviews. Rheumatology 7, 43 (Jan. 2011).

D. B. Burr, E. L. Radin, Microfractures and microcracks in subchondral bone: are they relevant to osteoarthrosis? Rheumatic diseases clinics of North America 29, 675 (Nov. 2003).

H. Madry, C. N. van Dijk, M. Mueller-Gerbl, The basic science of the subchondral bone. Knee surgery, sports traumatology, arthroscopy : official journal of the ESSKA 18, 419 (Apr. 2010).

S. Amin et al., Complete anterior cruciate ligament tear and the risk for cartilage loss and progression of symptoms in men and women with knee osteoarthritis. Osteoarthritis and cartilage / OARS, Osteoarthritis Research Society 16, 897 (Aug. 2008).

C. L. Hill et al., Cruciate ligament integrity in osteoarthritis of the knee. Arthritis and rheumatism 52, 794 (Mar. 2005).

S. Suri, D. A. Walsh, Osteochondral alterations in osteoarthritis. Bone, (Oct. 17, 2011).

D. J. Hunter et al., Increase in bone marrow lesions associated with cartilage loss: a longitudinal magnetic resonance imaging study of knee osteoarthritis. Arthritis and rheumatism 54, 1529 (May 2006).

R. Dreier, Hypertrophic differentiation of chondrocytes in osteoarthritis: the developmental aspect of degenerative joint disorders. Arthritis research & therapy 12, 216 (2010).

E. V. Tchetina, Developmental mechanisms in articular cartilage degradation in osteoarthritis. Arthritis 2011, 683970 (2011).

E. N. Blaney Davidson, P. M. van der Kraan, W. B. van den Berg, TGF-beta and osteoarthritis. Osteoarthritis and cartilage / OARS, Osteoarthritis Research Society 15, 597 (Jun. 2007).

M. Pombo-Suarez, M. T. Castano-Oreja, M. Calaza, J. Gomez-Reino, A. Gonzalez, Differential upregulation of the three transforming growth factor beta isoforms in human osteoarthritic cartilage. Annals of the rheumatic diseases 68, 568 (Apr. 2009).

P. M. van der Kraan, M. J. Goumans, E. Blaney Davidson, P. Ten Dijke, Age-dependent alteration of TGF-beta signalling in osteoarthritis. Cell and tissue research 347, 257 (Jan. 2012).

E. N. Blaney Davidson et al., Increase in ALK1/ALK5 ratio as a cause for elevated MMP-13 expression in osteoarthritis in humans and mice. J Immunol 182, 7937 (Jun. 15, 2009).

E. N. Blaney Davidson, E. L. Vitters, P. M. van der Kraan, W. B. van den Berg, Expression of transforming growth factor-beta (TGFbeta) and the TGFbeta signalling molecule SMAD-2P in spontaneous and instability-induced osteoarthritis: role in cartilage degradation, chondrogenesis and osteophyte formation. Annals of the rheumatic diseases 65, 1414 (Nov. 2006).

A. M. Valdes et al., Genetic variation in the SMAD3 gene is associated with hip and knee osteoarthritis. Arthritis and rheumatism 62, 2347 (Aug. 2010).

I. M. van de Laar et al., Mutations in SMAD3 cause a syndromic form of aortic aneurysms and dissections with early-onset osteoarthritis. Nature genetics 43, 121 (Feb. 2011).

I. M. van de Laar et al., Phenotypic spectrum of the SMAD3-related aneurysms-osteoarthritis syndrome. Journal of medical genetics 49, 47 (Jan. 2012).

A. M. Valdes et al., Association study of candidate genes for the prevalence and progression of knee osteoarthritis. Arthritis and rheumatism 50, 2497 (Aug. 2004).

(56) References Cited

OTHER PUBLICATIONS

J. Y. Yao et al., Mutation analysis of the Smad3 gene in human osteoarthritis. European journal of human genetics : EJHG 11, 714 (Sep. 2003).
X. Yang et al., TGF-beta/Smad3 signals repress chondrocyte hypertrophic differentiation and are required for maintaining articular cartilage. The Journal of cell biology 153, 35 (Apr. 2, 2001).
Q. Wu et al., Induction of an osteoarthritis-like phenotype and degradation of phosphorylated Smad3 by Smurf2 in transgenic mice. Arthritis and rheumatism 58, 3132 (Oct. 2008).
A. Scharstuhl et al., Inhibition of endogenous TGF-beta during experimental osteoarthritis prevents osteophyte formation and impairs cartilage repair. J Immunol 169, 507 (Jul. 1, 2002).
A. Scharstuhl, E. L. Vitters, P. M. van der Kraan, W. B. van den Berg, Reduction of osteophyte formation and synovial thickening by adenoviral overexpression of transforming growth factor beta/bone morphogenetic protein inhibitors during experimental osteoarthritis. Arthritis and rheumatism 48, 3442 (Dec. 2003).
A. E. Nelson et al., Serum transforming growth factor-beta 1 is not a robust biomarker of incident and progressive radiographic osteoarthritis at the hip and knee: the Johnston County Osteoarthritis Project. Osteoarthritis and cartilage / OARS, Osteoarthritis Research Society 18, 825 (Jun. 2010).
A. Fahlgren, B. Andersson, K. Messner, TGF-beta1 as a prognostic factor in the process of early osteoarthrosis in the rabbit knee. Osteoarthritis and cartilage / OARS, Osteoarthritis Research Society 9, 195 (Apr. 2001).
Y. Tang et al., TGF-beta1-induced migration of bone mesenchymal stem cells couples bone resorption with formation. Nature medicine 15, 757 (Jul. 2009).
Hahn, M., et al. "Trabecular bone pattern factor—a new parameter for simple quantification of bone microarchitecture." Bone 13.4 (1992): 327-330.
Wiese, C., et al. "Nestin expression—a property of multi-lineage progenitor cells?." Cellular and Molecular Life Sciences CMLS 61.19-20 (2004): 2510-2522.
Shi, Minlong, et al. "Latent TGF-[beta] structure and activation." Nature 474.7351 (2011): 343-349.
X. Cao et al., Irradiation induces bone injury by damaging bone marrow microenvironment for stem cells. Proceedings of the National Academy of Sciences of the United States of America 108, 1609 (Jan. 25, 2011).
K. S. Mohammad et al., TGF-beta-RI kinase inhibitor SD-208 reduces the development and progression of melanoma bone metastases. Cancer research 71, 175 (Jan. 1, 2011).
Javelaud, Delphine, et al. "TGF-β/SMAD/GLI2 signaling axis in cancer progression and metastasis." Cancer research 71.17 (2011): 5606-5610.
Kamekura, S., et al. "Osteoarthritis development in novel experimental mouse models induced by knee joint instability." Osteoarthritis and cartilage 13.7 (2005): 632-641.
S. Yang et al., Hypoxia-inducible factor-2alpha is a catabolic regulator of osteoarthritic cartilage destruction. Nature medicine 16, 687 (Jun. 2010).
Lotz, M. "Osteoarthritis year 2011 in review: biology." Osteoarthritis and Cartilage 20.3 (2012): 192-196.
Attur, Mukundan, et al. "Targeting the synovial tissue for treating osteoarthritis (OA): where is the evidence?." Best Practice & Research Clinical Rheumatology 24.1 (2010): 71-79.
Q. Wang et al., Identification of a central role for complement in osteoarthritis. Nature medicine 17, 1674 (2011).
Li, M., et al. "[Therapeutic effectiveness of intra-knee-articular injection of platelet-rich plasma on knee articular cartilage degeneration]." Zhongguo xiu fu chong jian wai ke za zhi= Zhongguo xiufu chongjian waike zazhi= Chinese journal of reparative and reconstructive surgery 25.10 (2011): 1192-1196.
Sekiya, Ichiro, et al. "Human mesenchymal stem cells in synovial fluid increase in the knee with degenerated cartilage and osteoarthritis." Journal of Orthopaedic Research 30.6 (2012): 943-949.
Koyama, Noriaki, et al. "Pluripotency of mesenchymal cells derived from synovial fluid in patients with temporomandibular joint disorder." Life sciences 89.19 (2011): 741-747.
Michalczyk, Karolina, and Melanie Ziman. "Nestin structure and predicted function in cellular cytoskeletal organisation." Histology and histopathology 20.2 (2005): 665-671.
Méndez-Ferrer, Simón, et al. "Mesenchymal and haematopoietic stem cells form a unique bone marrow niche." nature 466.7308 (2010): 829-834.
Bonaguidi, Michael A., et al. "In vivo clonal analysis reveals self-renewing and multipotent adult neural stem cell characteristics." Cell 145.7 (2011): 1142-1155.
Van Beuningen, H.M. et al. "Osteoarthritis-like changes in the murine knee joint resulting from intra-articular transforming growth factor-Beta injections" Osteoarthritis and Cartilage 2000, 8, 25-33.

\* cited by examiner

FIGS. 1A(ii)

FIGS. 1A(iii)

FIGS. 1A(iv)

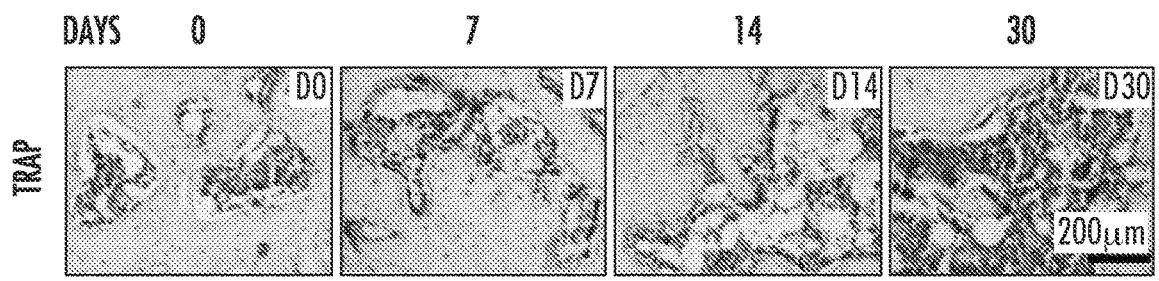
*FIGS. 1E(i)*
*FIGS. 1F(i)*
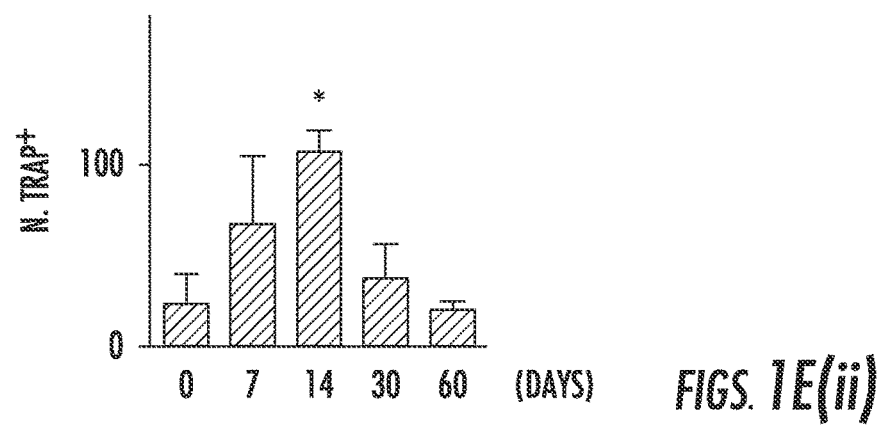
*FIGS. 1E(ii)*
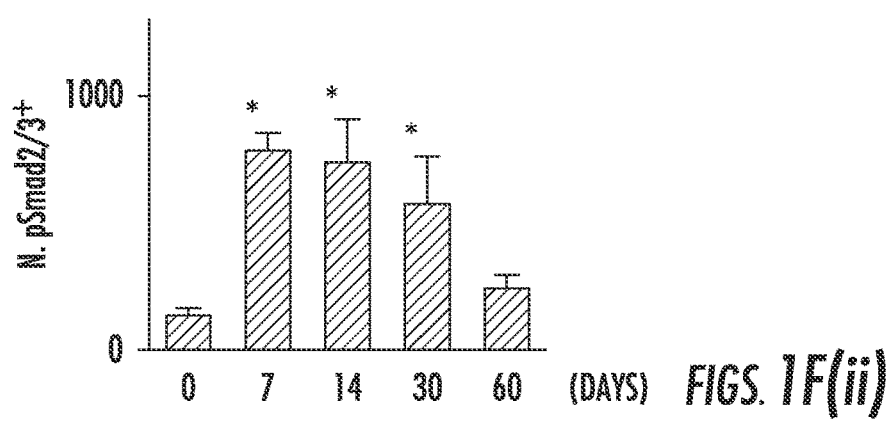
*FIGS. 1F(ii)*

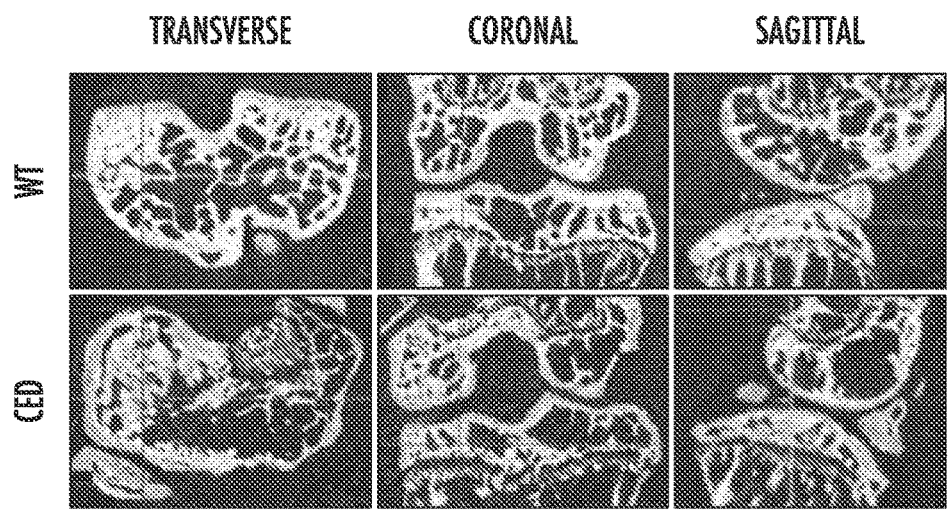
FIGS. 2A(i)
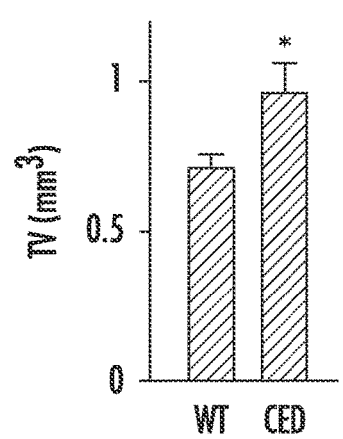
FIGS. 2A(ii)
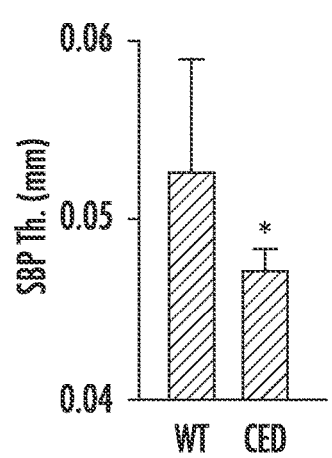
FIGS. 2A(iii)
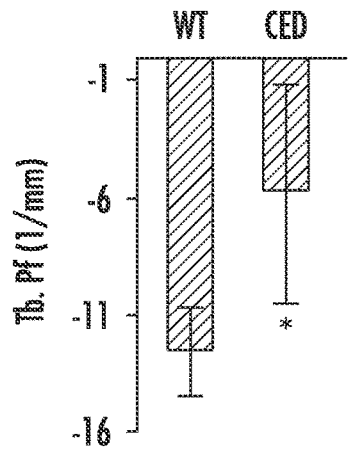
FIGS. 2A(iv)

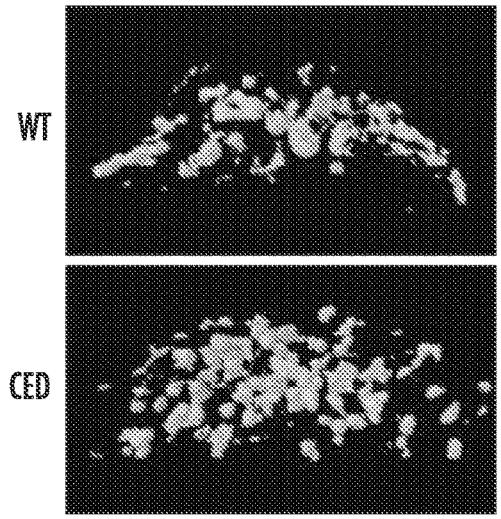
FIGS. 2E(i)
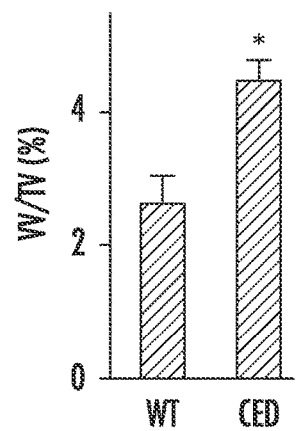
FIGS. 2E(ii)
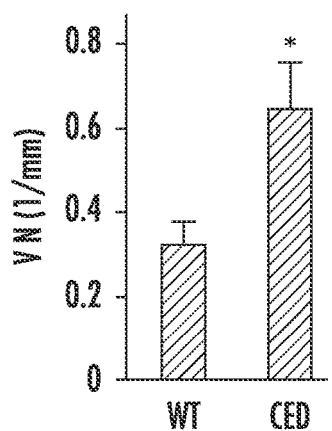
FIGS. 2E(iii)
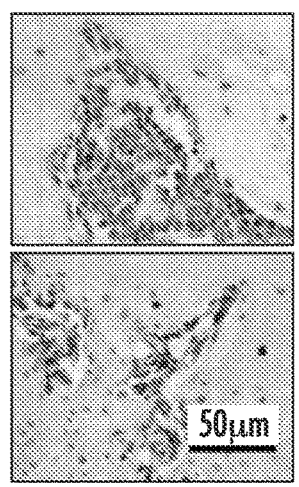
FIGS. 2F(i)
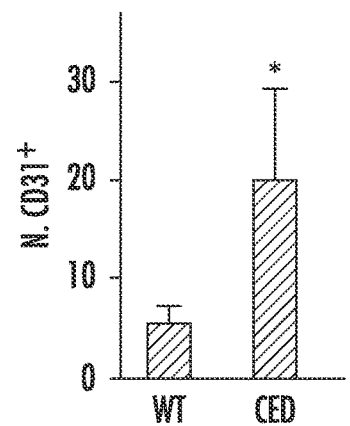
FIGS. 2F(ii)

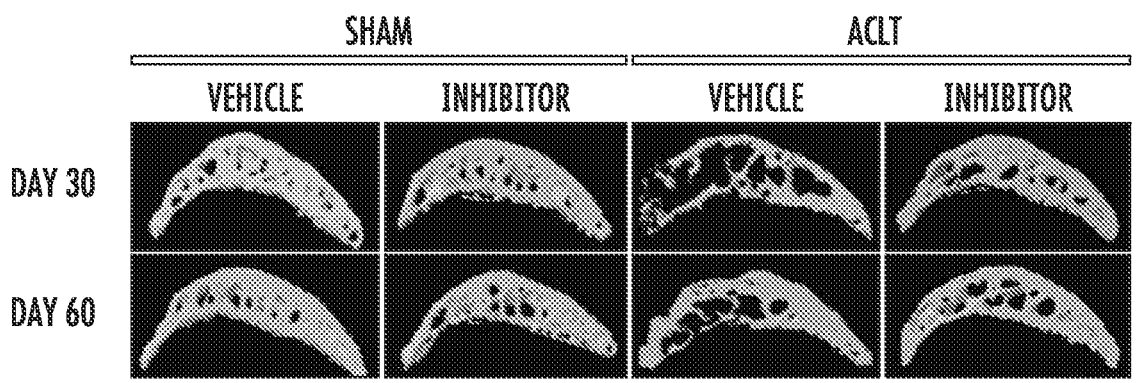
FIGS. 3A(i)
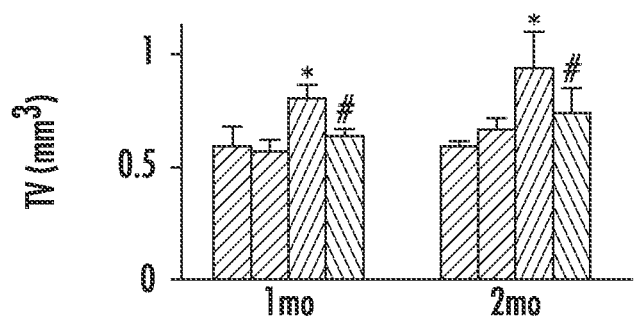
FIGS. 3A(ii)
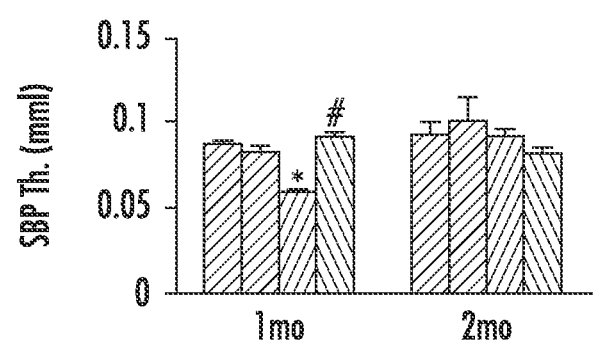
FIGS. 3A(iii)
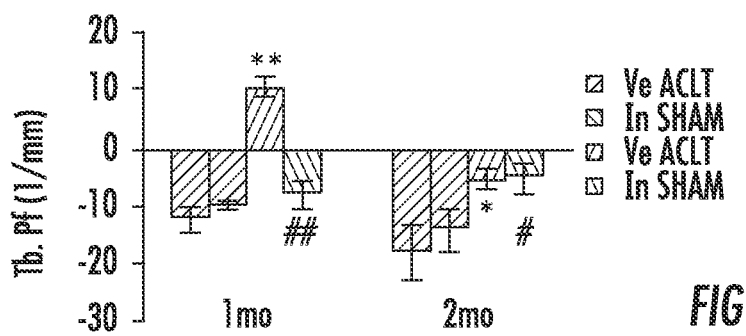
FIGS. 3A(iv)

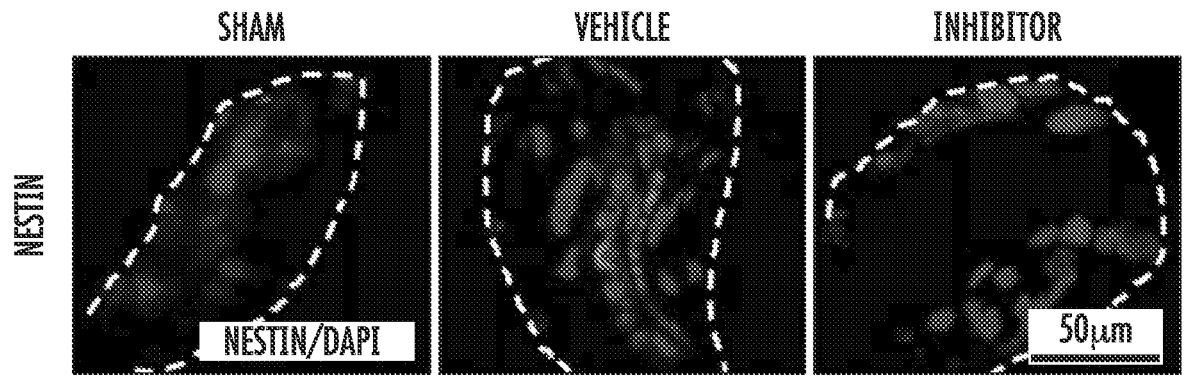
FIGS. 4A(i)
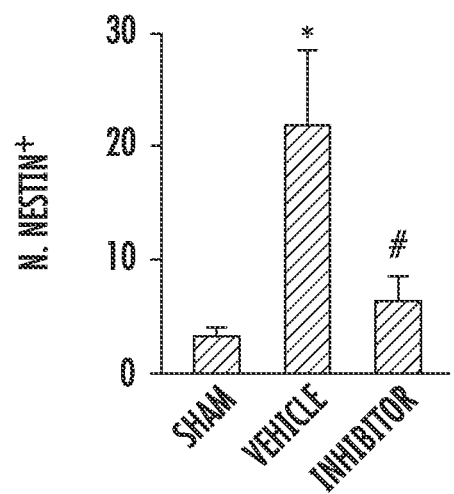
FIGS. 4A(ii)

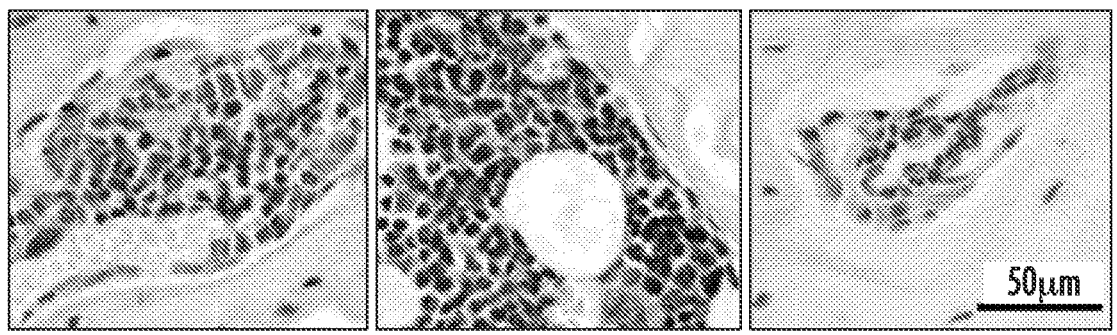
FIGS. 4B(i)
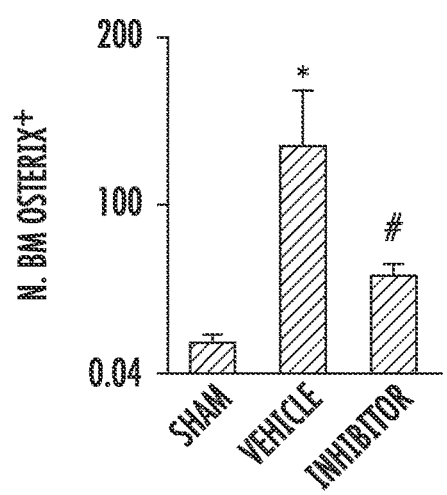
FIGS. 4B(ii)

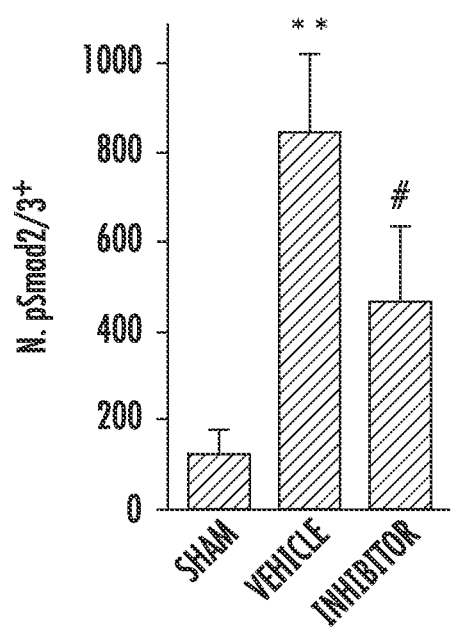
FIGS. 4I(ii)
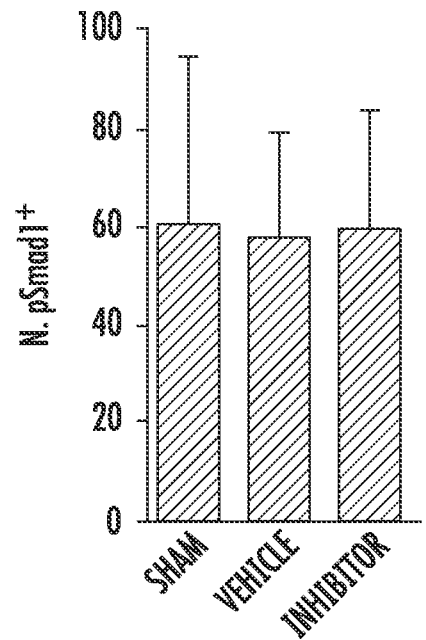
FIGS. 4J(ii)
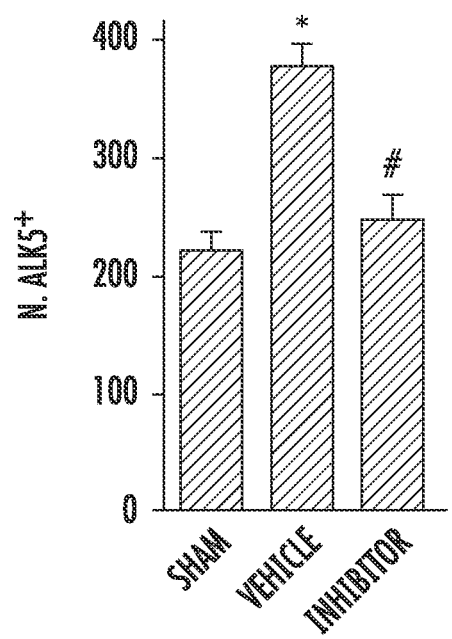
FIGS. 4K(ii)
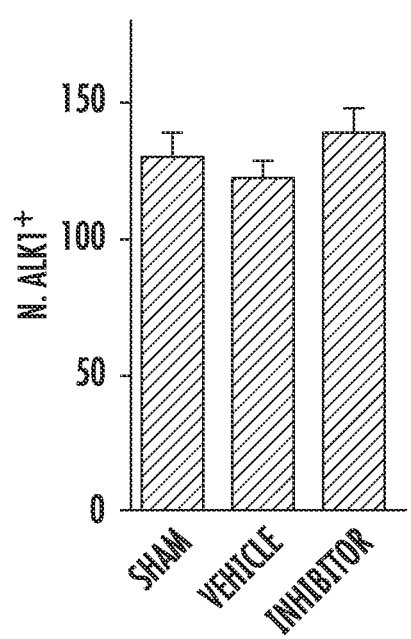
FIGS. 4L(ii)

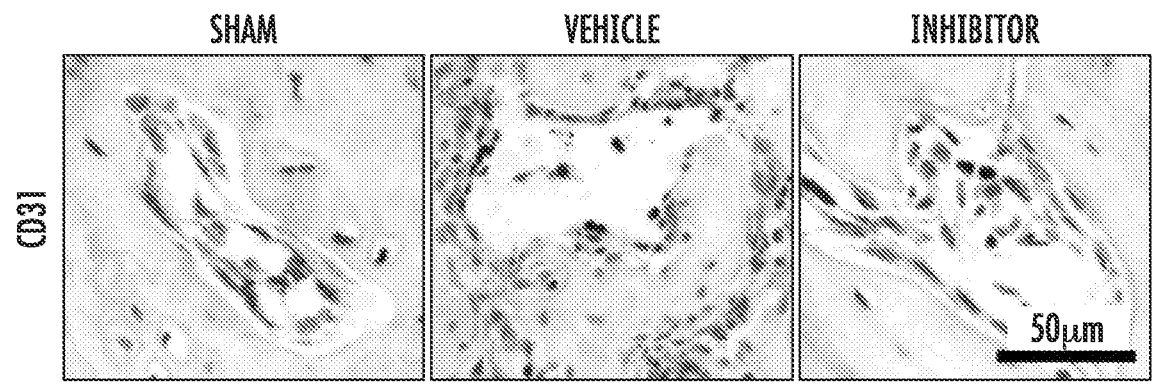
FIGS. 4M(i)
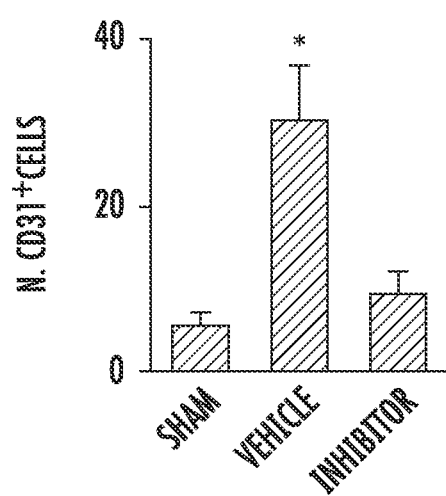
FIGS. 4M(ii)

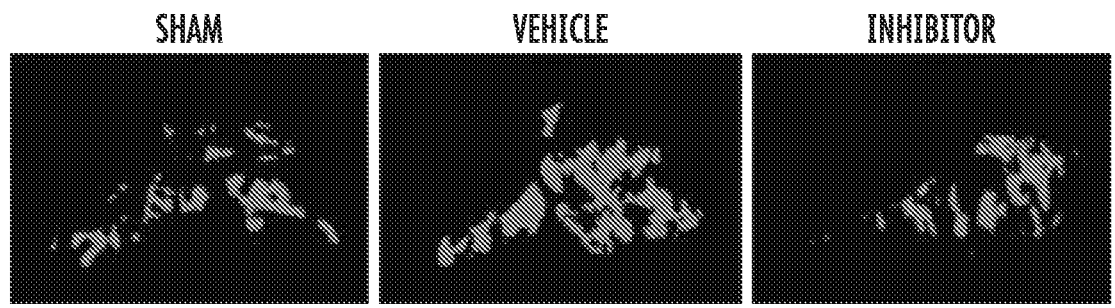
FIGS. 4N(i)
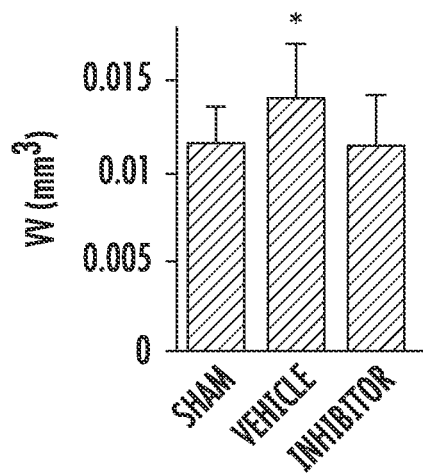
FIGS. 4N(ii)
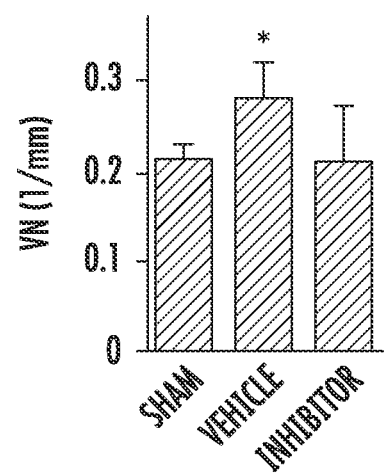
FIGS. 4N(iii)

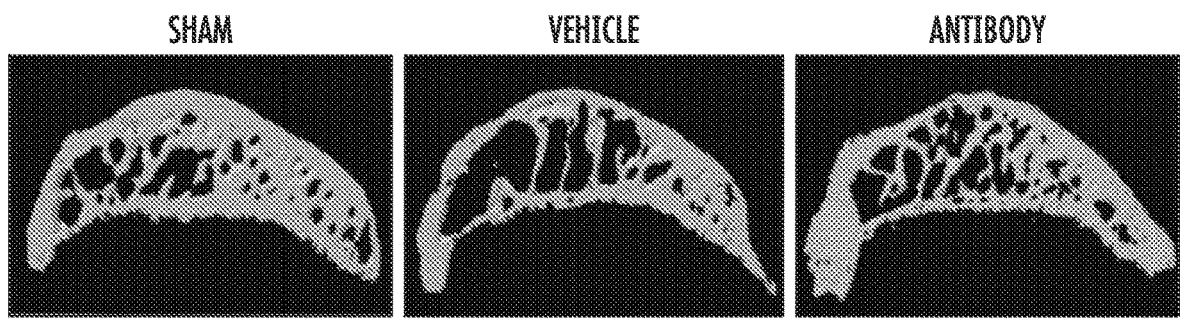
FIGS. 5A(i)
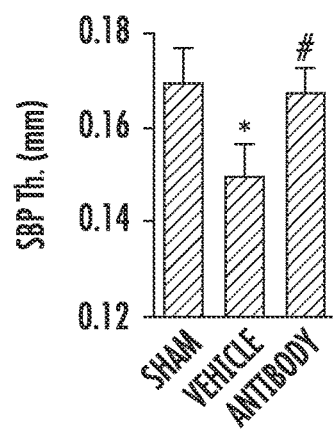
FIGS. 5A(ii)
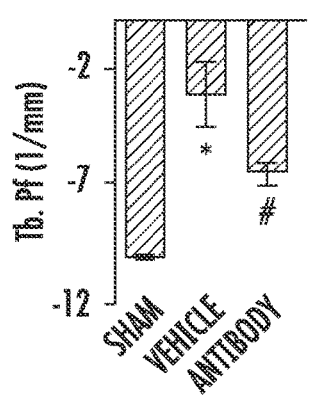
FIGS. 5A(iii)
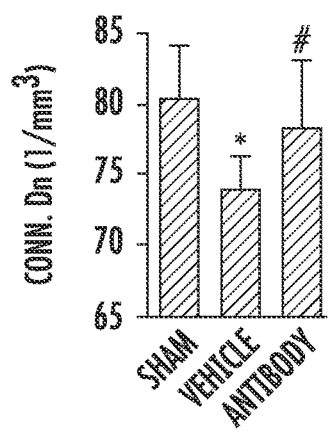
FIGS. 5A(iv)

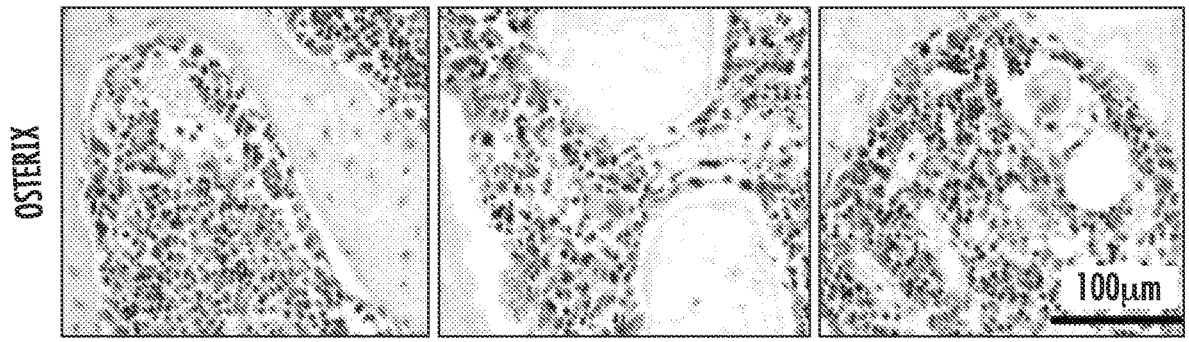
FIGS. 5B(i)
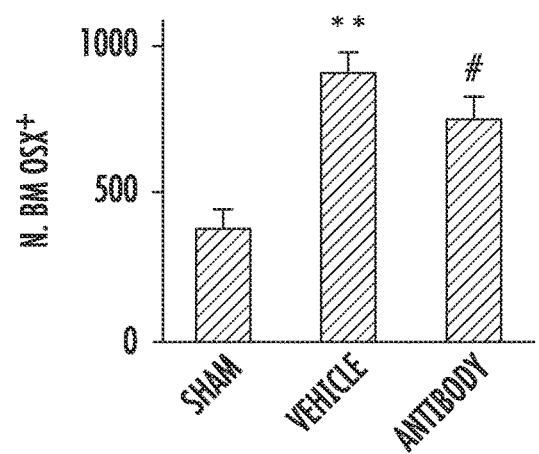
FIGS. 5B(ii)

FIGS. 5E(i)
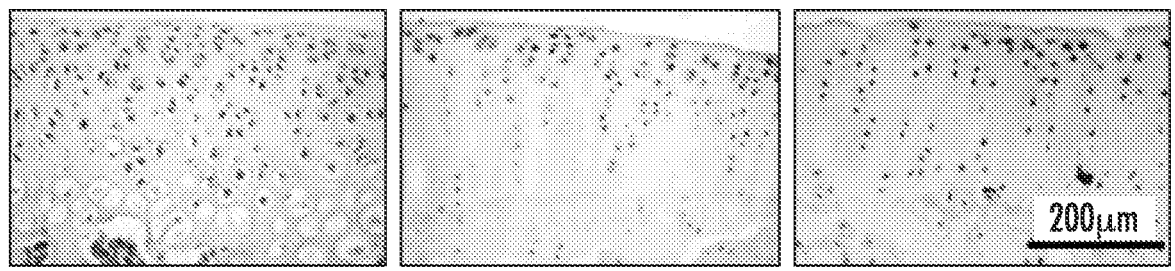
FIGS. 5F(i)
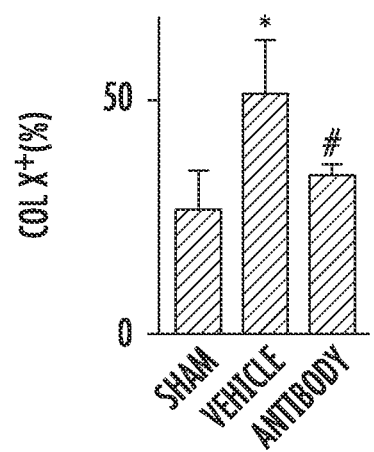
FIGS. 5E(ii)
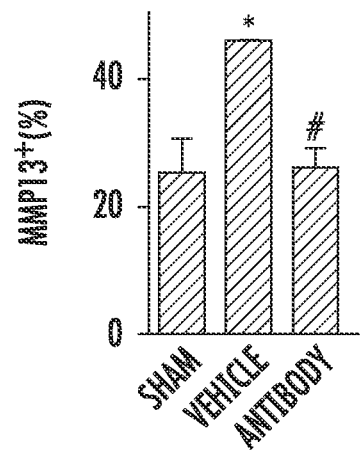
FIGS. 5F(ii)

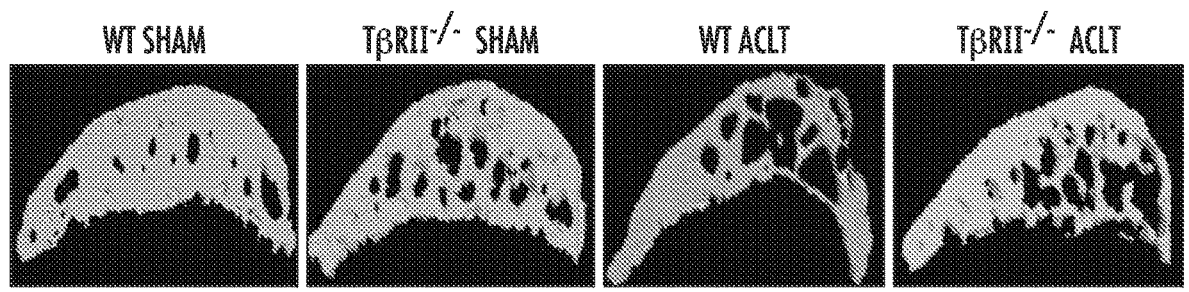
FIGS. 6A(i)
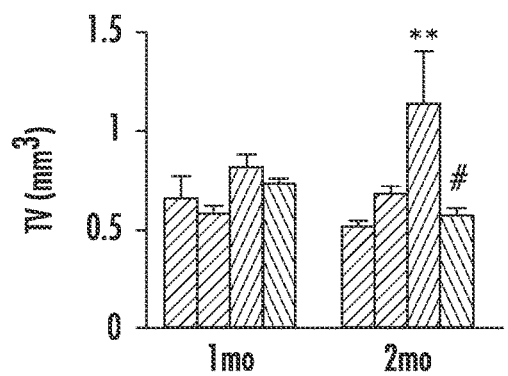
FIGS. 6A(ii)
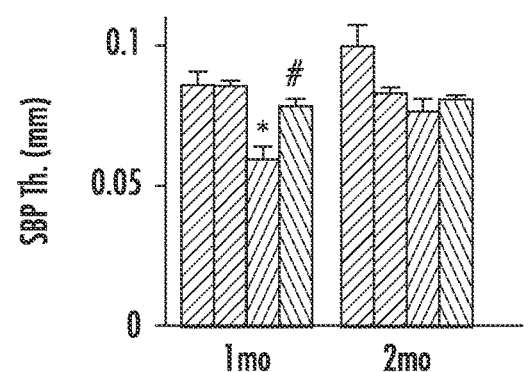
FIGS. 6A(iii)
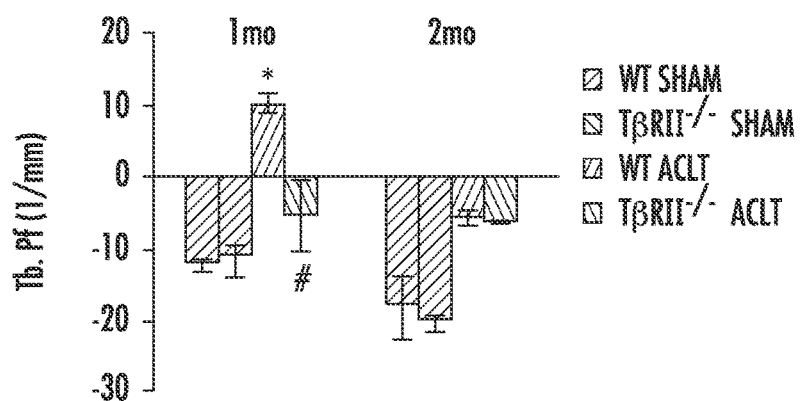
FIGS. 6A(iv)

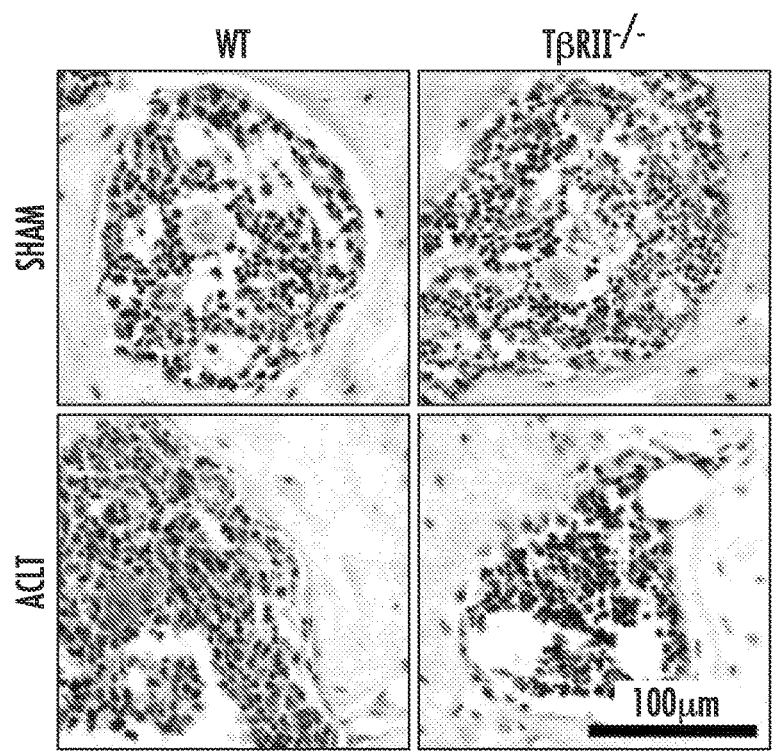
FIGS. 6B(i)
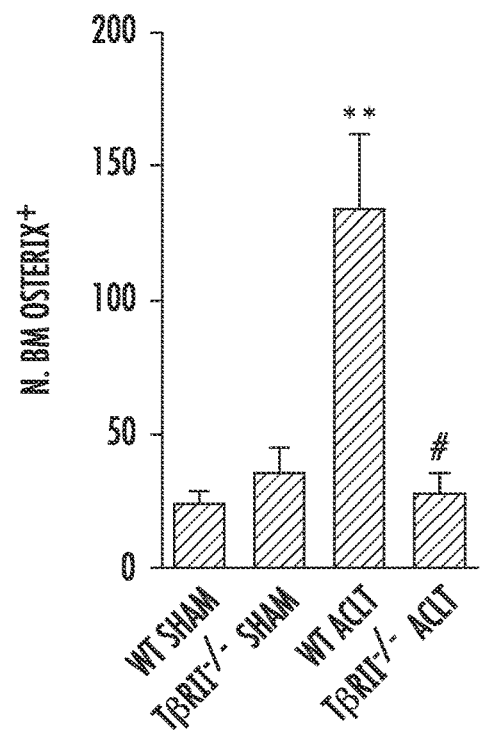
FIGS. 6B(ii)

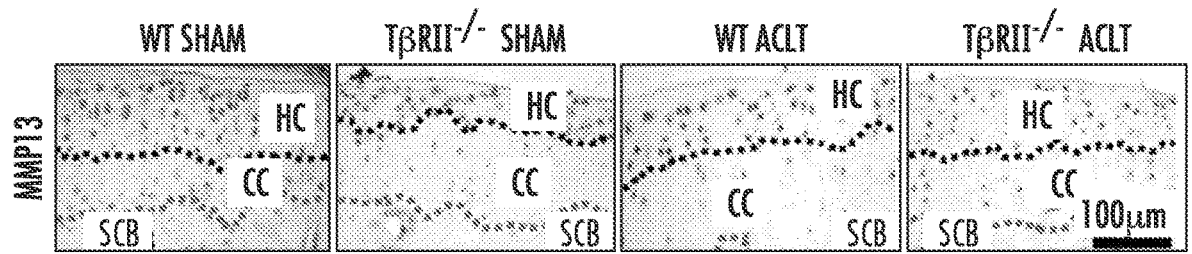
*FIGS. 6H(i)*
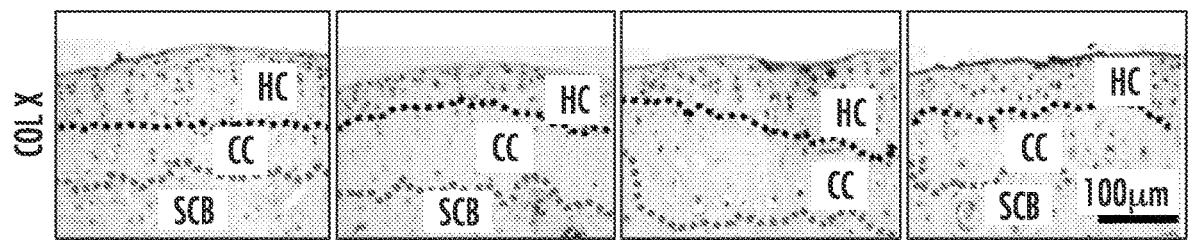
*FIGS. 6I(i)*
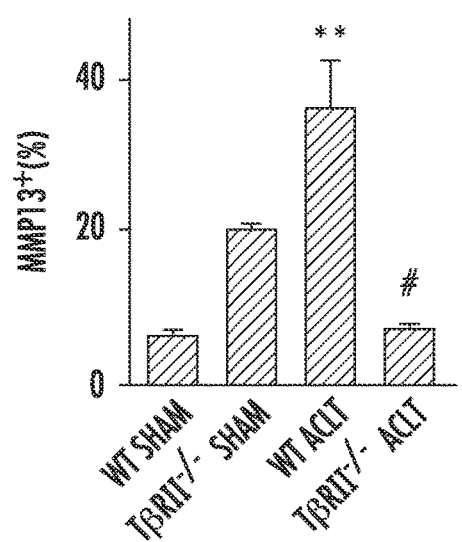
*FIGS. 6H(ii)*
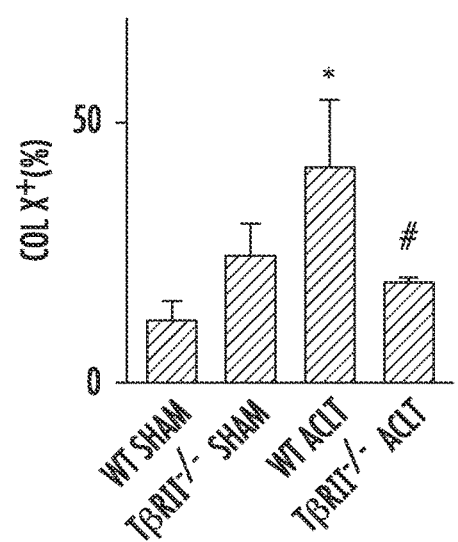
*FIGS. 6I(ii)*

TIBIAL PLATEAU

TIBIAL CORONAL SECTION

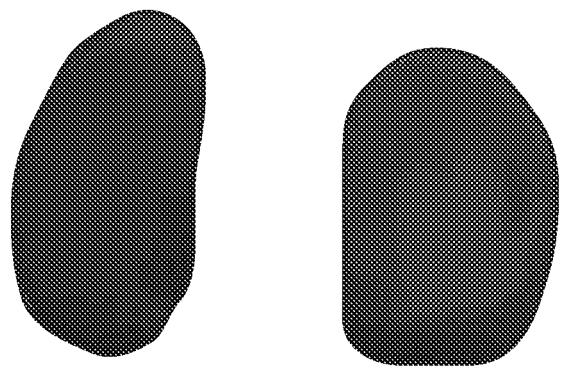
NORMAL
FIGS. 8C
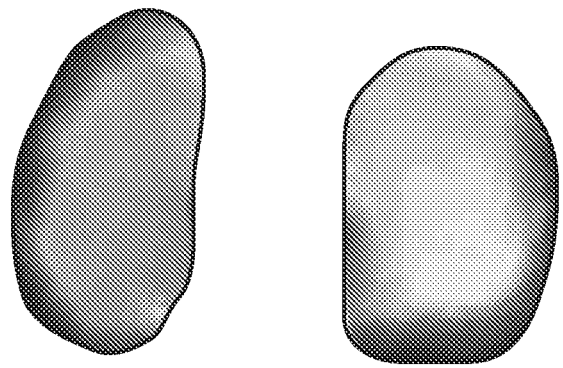
TIBIAL PLATEAU BONE AREA EXPANSION BY 1%
FIGS. 8D
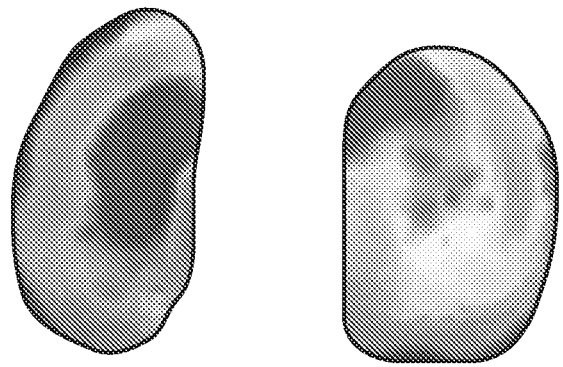
TIBIAL PLATEAU BONE AREA EXPANSION BY 2%
FIGS. 8E
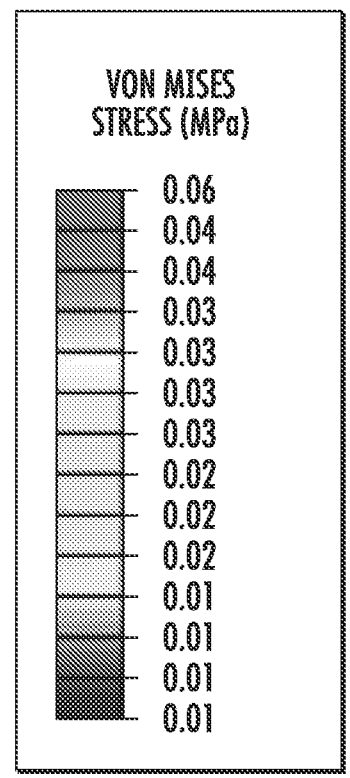
VON MISES STRESS (MPa)
- 0.06
- 0.04
- 0.04
- 0.03
- 0.03
- 0.03
- 0.03
- 0.02
- 0.02
- 0.02
- 0.01
- 0.01
- 0.01
- 0.01

STRESS DISTRIBUTION IN TIBIAL ARTICULAR CARTILAGE

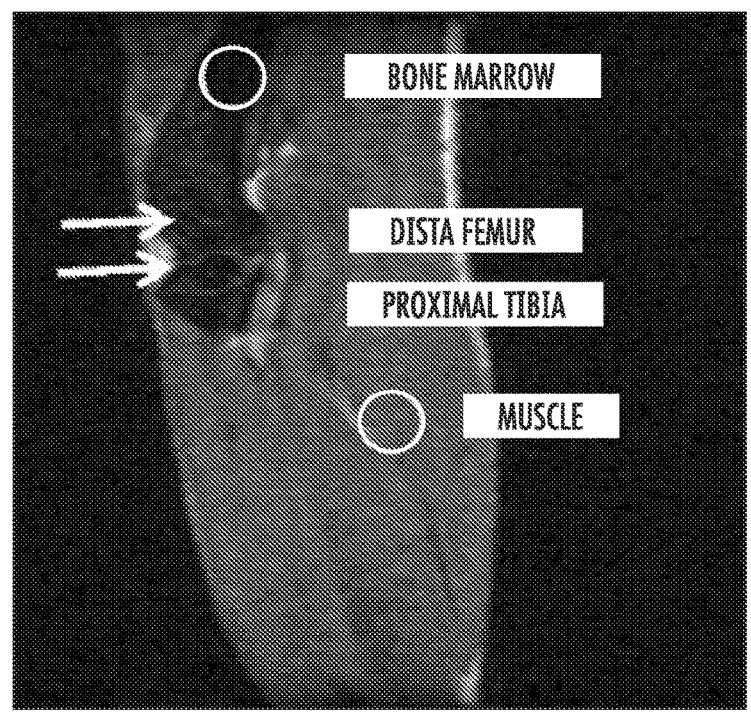
FIGS. 13A
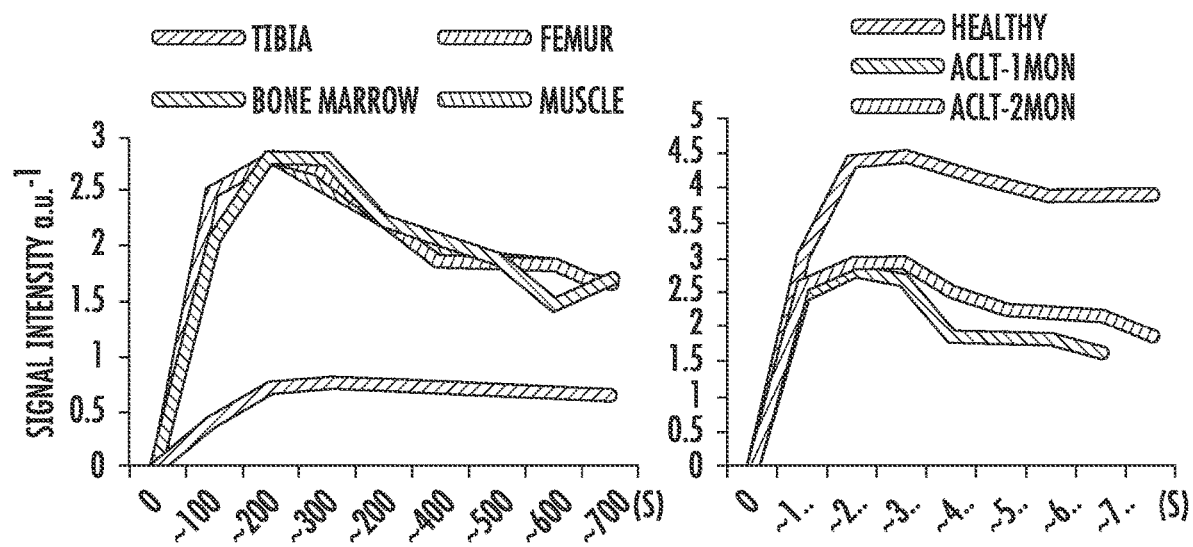
FIGS. 13B
FIGS. 13C

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: 5' Cre primer

<400> SEQUENCE: 1
caaatagccc tggcagat                                                  18

<210> SEQ ID NO 2
<211> LENGTH: 20
<212> TYPE: DNA
<213> ORGANISM: Artificial Sequence
<220> FEATURE:
<223> OTHER INFORMATION: 3' Cre primer

<400> SEQUENCE: 2
tgatacaagg gacatcttcc                                                20

<210> SEQ ID NO 3
<211> LENGTH: 20
<212> TYPE: DNA
<213> ORGANISM: Artificial Sequence
<220> FEATURE:
<223> OTHER INFORMATION: 5' lox1F primer

<400> SEQUENCE: 3
taaacaaggt ccggagccca                                                20

<210> SEQ ID NO 4
<211> LENGTH: 20
<212> TYPE: DNA
```

```
<213> ORGANISM: Artificial Sequence
<220> FEATURE:
<223> OTHER INFORMATION: 3' lox1R primer

<400> SEQUENCE: 4
acttctgcaa gaggtcccct                                              20
```

COMPOSITIONS AND METHODS FOR TREATING OR PREVENTING OSTEOARTHRITIS

CROSS-REFERENCE TO RELATED APPLICATIONS

This application is a 35 U.S.C. § 371 U.S. national entry of International Application PCT/US2013/039076, having an international filing date of May 1, 2013, which claims the benefit of U.S. Provisional Application No. 61/640,886, filed May 1, 2012, and U.S. Provisional Application No. 61/697,483, filed Sep. 6, 2012, the contents of each of the aforementioned applications are herein incorporated by reference in their entireties.

STATEMENT OF GOVERNMENTAL INTEREST

This invention was made with government support under grant nos. AR053973 and DK057501 awarded by the National Institutes of Health. The government has certain rights in the invention.

FIELD OF THE INVENTION

The present invention relates to the field of osteoarthritis. More specifically, the present invention provides compositions and methods useful for treating or preventing osteoarthritis.

INCORPORATION-BY-REFERENCE OF MATERIAL SUBMITTED ELECTRONICALLY

This application contains a sequence listing. It has been submitted electronically via EFS-Web as an ASCII text file entitled "P11908-04_ST25.txt." The sequence listing is 1,106 bytes in size, and was created on Oct. 30, 2014. It is hereby incorporated by reference in its entirety.

BACKGROUND OF THE INVENTION

Osteoarthritis is the most common degenerative joint disorder, mainly afflicting the weight-bearing joints, like hips and knees, and is the leading cause of physical disability, predicted to affect 67 million people in the United States by 2030. Despite the identified risk factors, e.g. mechanical, metabolic or genetic, the exact pathogenesis of osteoarthritis remains unclear. Currently, there is no effective disease modifying treatment for osteoarthritis until the end stage of disease necessitating joint replacement.

SUMMARY OF THE INVENTION

The present invention is based, at least in part, on the discovery that inhibition of transforming growth factor beta (TGF-beta or TGFβ) can be used as a therapy for osteoarthritis. In addition, the present inventors discovered that bone marrow osteoid islet/lesions can be used as a biomarker or readout to monitor the progress of osteoarthritis therapies.

In one aspect, the present invention provides methods and compositions useful for treating or preventing osteoarthritis. In one embodiment, a method for treating or preventing osteoarthritis in a patient comprises the step of administering to the patient a therapeutically effective amount of a transforming growth factor beta (TGF-beta) inhibitor. In a specific embodiment, the TGF beta is a member of the TGF-beta superfamily. In more specific embodiments, the TGF-beta is TGF-beta 1, TGF-beta 2, TGF-beta 3. In a specific embodiment, the TGF-beta is TGF-beta 1. In other embodiments, the inhibitor is a small molecule, an antibody, a protein, a peptide, or a nucleic acid. In a specific embodiment, the inhibitor is an antibody. In other embodiments, the inhibitor inhibits active TGF-beta, TGF-beta receptor, a protease responsible for activating a precursor TGF-beta into mature TGF-beta, expression of TGF-beta, or combinations of the foregoing.

In particular embodiments, the inhibitor is administered into the subchondral bone area. In a more specific embodiment, a method for treating or preventing osteoarthritis osteoarthritis in a patient comprises the step of administering to the patient a therapeutically effective amount of a TGF-beta inhibitor into the subchondral bone area. In another embodiment, a method for treating or preventing osteoarthritis in a patient comprises the step of administering to the patient a therapeutically effective amount of a TGF-beta 1 blocking antibody into the subchondral bone area.

The present invention also provides a method for preventing onset of ligament injury-induced osteoarthritis in a patient comprising the step of administering to the patient a therapeutically effective amount of a TGF-beta inhibitor into the subchondral bone of the joint affected by the injured ligament. In a further embodiment, a method for preventing onset of ligament injury-induced osteoarthritis in a patient comprises the step of administering to the patient a therapeutically effective amount of a TGF-beta inhibitor into the subchondral bone of the joint affected by the injured ligament.

The present invention also provides a method for reducing the degeneration of articular cartilage in a joint comprising the step of administering an effective amount of a TGF-beta inhibitor locally at or near the joint site. In one embodiment, the inhibitor is administered into the subchondral bone area of the joint. In another embodiment, the inhibitor is a small molecule. In certain embodiments, the small molecule is halofuginone, kartogenin, or SB-505124. In certain embodiments, the TGF-beta inhibitor is conjugated to bisphosphonate or a derivative thereof. In a specific embodiment, the bisphosphonate is alendronate. The preset invention also provides a method for treating or preventing osteoarthritis in a patient comprising the step of administering an effective amount of a small molecule TGF-beta 1 inhibitor conjugated to bisphosphonate.

In another aspect, the present invention provides methods for diagnosing osteoarthritis and monitoring treatment thereof. In general, the formation, presence, absence, increase or decrease in bone marrow osteoid islets/lesions can be used to diagnose or monitor treatment of osteoarthritis. In one embodiment, a method for diagnosing osteoarthritis in a patient comprises the step of identifying the presence or absence of osteoid islets in the subchondral bone marrow of the patient, wherein the presence or absence of the osteoid islets provides the diagnosis. In a specific embodiment, the islets are identified by using magnetic resonance imaging (MRI). In one embodiment, a method for diagnosing osteoarthritis in a patient comprises the step of identifying the presence or absence of osteoid islets in the subchondral bone marrow of the patient using magnetic resonance imaging (MRI), wherein the presence or absence of the osteoid islets provides the diagnosis. In another embodiment, a method for monitoring osteoarthritis therapy in a patient comprises the step of comparing the extent of osteoid islets formation in the subchondral bone marrow of the patient at at least two time points, wherein the osteoid islets are detected using MRI. Time points can include, but are not limited to, prior to, during and after osteoarthritis treatment. In a further embodiment, the present invention provides a method for treating osteoarthritis in a patient comprising the steps of (a) detecting the presence of osteoid islets in the subchondral bone marrow of the patient using MRI; and (b) administering a TGF-β inhibitor to the patient.

BRIEF DESCRIPTION OF THE FIGURES

FIGS. 1A-1F. Upregulated TGF-β signaling in the subchondral bone is associated with changes of subchondral bone architecture in ACLT mice. (FIG. 1A(i) (top)) Three-dimensional high-resolution μCT images of tibial subchondral bone medial compartment (sagittal view) at 0, 30, or 60 days post sham or ACLT surgery. Altered morphology of subchondral bone plate is indicated by red arrows. Scale bar, 500 μm. (FIG. 1B (center)) Sanfranin O-Fast green staining of sagittal sections of tibia medial compartment, proteoglycan (red) and bone (green). Arrows indicate loss of proteoglycan at 30 and 60 days post-surgery. Scale bar, 500 μm. (FIG. 1C (bottom) H&E staining of subchondral bone plate (SBP) and cartilage. Hyaline cartilage (HC) and calcified cartilage (CC) thickness are indicated by double arrowed lines. Scale bar, 100 μm. Quantitative analysis of structural parameters of subchondral bone by μCT analysis: (FIG. 1A(ii) total tissue volume (TV), (FIG. 1A(iii) thickness of subchondral bone plates (SBP Th) and (FIG. 1A(iv) trabecular pattern factor (Tb. Pf). n=8; *$P<0.05$ vs. sham group at corresponding time points; #$P<0.05$ vs. ACLT group at 30 days post-surgery. (FIG. 1D) OARSI scores at 0-90 days post-surgery. n=8; *$P<0.05$ and **$P<0.01$ vs. Day 0 group. (FIG. 1E(i)) TRAP staining (pink, top), scale bar, 200 μm and (FIG. 1F(i)) immunohistochemical analysis of pSmad2/3$^+$ cells (brown, bottom), scale bar, 100 μm in mouse tibial subchondral bone after ACLT surgery. Quantitative analysis of TRAP$^+$ (FIG. 1E(ii)) or p-Smad2/3$^+$ cells (FIG. 1F(ii)) per bone marrow area (mm$^2$), reported as mean±SD. n=8; *$P<0.05$ vs. Day 0 group.

FIGS. 2A-2I. CED mice with transgenic activating mutation of TGF-β1 demonstrate knee OA phenotype. (FIG. 2A(i)) μCT images of transverse, coronal and sagittal views of tibia subchondral bone of 4 month old CED mice vs. wild-type (WT) littermates. Scale bar, 1 mm, with quantitative analysis of structural parameters of subchondral bone: (FIG. 2A(ii) total tissue volume (TV), (FIG. 2A(iii) thickness of subchondral bone plates (SBP Th) and (FIG. 2A(iv) trabecular pattern factor (Tb. Pf). (FIG. 2B) Sanfranin O-Fast green, scale bar, 500 μm(top) and (FIG. 2C) H&E staining of sagittal sections of tibia medial compartment, scale bar, 100 μm(bottom). Double arrowed lines indicate hyaline cartilage (HC) and calcified cartilage (CC) thickness. Subchondral bone plate=SBP. (FIG. 2D) OARSI scores of CED vs. WT littermates. (FIG. 2E(i)) CT-based micro-angiography of tibia subchondral bone of CED vs. WT littermates with quantification of vessel volume relative to (FIG. 2E(ii)) tissue volume (VV/TV) and (FIG. 2E(iii)) vessel number (VN). Scale bar, 500 μm. (FIG. 2F(i)) Immunohistochemical or immunofluorescent analysis of CD31$^+$ (brown), scale bar, 50 μm (FIG. 2F(ii)); FIG. 2G(i) nestin$^+$ (red, top), scale bar, 50 μm; (FIG. 2H(i) osterix$^+$ (brown, bottom) cells, scale bar, 100 μm. DAPI stains nuclei (blue) ((top)) in tibial subchondral bone of CED vs. WT littermates. (FIGS. 2G(ii) and FIG. 2H(ii)) n=10; *$P<0.05$, **$P<0.01$. ((FIG. 2I)) ELISA analysis of active TGF-β1 in condition medium of human tibia subchondral bone specimen. Healthy: subchondral bone collected from healthy donors, Oac$^+$: OA subchondral bone with articular cartilage, Oac$^-$: OA subchondral bone without articular cartilage. n=10; *$P<0.05$; **$P<0.01$. Data reported as mean±SD.

FIGS. 3A-3F. TβRI inhibitor stabilized subchondral bone architecture and attenuated articular cartilage degeneration in ACLT mice. (FIG. 3A(i)) Three-dimensional μCT images of tibia subchondral bone medial compartment (sagittal view) of mice treated with 1 mg kg$^{-1}$ of TβRI inhibitor daily for 30 days and sacrificed 1 or 2 months post ACLT or sham surgery. Scale bar, 1 mm. Quantitative analysis of structural parameters of subchondral bone by μCT analysis: (FIG. 3A(ii) tissue volume (TV), (FIG. 3A(iii) thickness of subchondral bone plate (SBP), and (FIG. 3A(iv) trabecular pattern factor (Tb. Pf). (FIG. 3B) Sanfranin O-fast green staining of articular cartilage in sagittal sections of tibia medial compartment from mice treated with vehicle or inhibitor for 1 month and sacrificed 2 months post ACLT or sham surgery. Scale bar, 500 μm (top) or 100 μm (bottom). (FIG. 3C) OARSI scores of sham or ACLT mice treated with either vehicle (Ve) or TβRI inhibitor (In). Quantitative analysis of the percentage of (FIG. 3D) MMP13$^+$ and (FIG. 3E) type X collagen$^+$ chondrocytes in immunohistochemically stained articular cartilage tissue sections. (FIG. 3F) Maxcontactat (%) of the gait analysis in mice 2 months post ACLT or sham surgery treated with vehicle or inhibitor for 1 month. n=8-12; *$P<0.05$ **$P<0.01$ vs. Ve Sham; #$P<0.05$, ##$P<0.01$ vs. Ve ACLT, NS: not significant. Data reported as mean±SD.

(FIG. 4P) Representative MRI T1 weighted images. Red arrow indicates bone marrow lesion. n=8-12; *$P<0.05$ vs. sham; #$P<0.05$ vs. vehicle.

FIGS. 5A-5F. Local subchondral administration of TGF-β antibody reduced aberrant subchondral bone formation and articular cartilage degeneration in ACLT rats. (FIG. 5A(i)) Three dimensional μCT images of tibia subchondral bone medial compartment (sagittal view) in rats that underwent sham (Sham) or ACLT surgery with implantation of an alginate bead containing either vehicle (Vehicle) or TGF-β antibody (Antibody) 3 months post-surgery. Scale bar, 1 mm. Quantitative analysis of structural parameters of subchondral bone by μCT analysis: (FIG. 5A(ii) thickness of subchondral bone plate (SBP), (FIG. 5A(iii) trabecular pattern factor (Tb. Pf) and (FIG. 5A(iv) connectivity density (Conn. Dn). (FIGS. 5B(i) and 5B(ii)) Immunohistochemical and quantitative analysis of osterix (brown). Scale bars, 100 μm. (FIG. 5C) Sanfranin O-fast green staining of sagittal sections of subchondral tibia medial compartment, scale bar, 400 μm. (FIG. 5D) OARSI scores. Immunofluorescent or immunohistochemical and quantitative analysis of (FIGS. 5E(i) and 5E(ii)) type X collagen (green) and (FIGS. 5F(i) and 5F(ii)) MMP13 (brown) in articular cartilage. DAPI stains nuclei (blue) (center). Scale bars, 200 μm. n=8; *$P<0.05$, **$P<0.01$ vs. sham, #$P<0.05$ vs. vehicle ACLT rats.

FIGS. 6A-6I. Inducible knockout of TβRII in nestin+ cells reduced the changes in subchondral bone and articular cartilage in ACLT mice. (FIG. 6A(i)) Three-dimensional μCT images of tibia subchondral bone medial compartment (sagittal view) in wild-type (WT) or Nestin-Cre™ER:: TβRII$^{fl/fl}$ (TβRII$^{-/-}$) mice 2 months after undergoing sham or ACLT surgery. Scale bar, 500 μm, and quantitative analysis of structural parameters of subchondral bone by μCT analysis: (FIG. 6A(ii) subchondral bone tissue volume (TV), (FIG. 6A(iii) thickness of subchondral bone plate (SBP), and (FIG. 6A(iv) trabecular pattern factor (Tb. Pf). (FIGS. 6B(i) and 6B(ii)) Immunohistochemical and quantitative analysis of osterix (brown). Scale bar, 100 μm. (FIG. 6C) Double-immunofluorescent analysis of osteocalcin (red) and β-gal (green) in subchondral bone of Nestin-Cre™ER::Rosa26-LacZ$^{fl/fl}$ mice that underwent sham or ACLT operation and were treated with vehicle- or TβRI inhibitor. Scale bar, 40 μm. (FIGS. 6D and 6E) Sanfranin O-fast green and H&E staining of the sagittal sections of tibia medial compartment. Scale bar, 100 μm. (FIG. 6F) OARSI scores. (FIG. 6G) Max_contact_at (%) of the gait analysis in mice. Immunohistochemical and quantitative analysis of (FIGS. 6H(i) and 6H(ii)) MMP13 and (FIGS. 6I(i) and 6I(ii)) type X collagen (both stain brown). HC=hylane cartilage; CC=calcified cartilage; SCB=subchondral bone. n=8; *$P<0.05$, **$P<0.01$ vs. wild type sham, #$P<0.05$, ##$P<0.01$ vs. wild type ACLT group. Scale bars, 100 μm. Model of elevated active TGF-β1 in the subchondral bone at the onset of OA. TGF-β1 is activated in the subchondral bone in response to abnormal mechanical loading. The accumulated high concentrations of active TGF-β1 stimulate increases in MSCs and osteoprogenitors in the marrow, which lead to aberrant bone formation and angiogenesis for OA progression.

(FIG. 7A) Representative 3D reconstructed μCT images (top panel) and H&E staining (bottom panel) of cross-section of subchondral bone medial compartment. The coronal view in the top panel demonstrates increased bone volume and disrupted bone structure in OA patients compared to healthy controls. Consistent with μCT scanning results, hyaline cartilage (HC) was decreased over OA subchondral bone. At the same time, calcified cartilage (CC) and subchondral bone (SCB) moved toward articular cartilage, and articular cartilage was totally lost at the late stages of OA. Double tide marks are indicated by arrows. Quantitative analysis of structural parameters of subchondral bone from μCT analysis: (FIG. 7B) bone volume/tissue volume (BV/TV), (FIG. 7C) bone mineral density (BMD), and (FIG. 7D) average subchondral bone plate thickness (SBP Th). BV/TV increased at the sites where cartilage was worn out (Oac−). BMD was not significantly increased parallel to the bone volume fraction, indicating that the newly formed bone was less mineralized. The average SBP Th was greater in OA samples compared to healthy controls, regardless of the presence of articular cartilage. (FIG. 7E) Percent distribution of SBP Th (SBP Th Distr). The increased thickness of the SBP in OA samples was not uniform. The SBP generally became thicker as evidenced by a right shift in the distribution curves in the OA samples. (FIG. 7F) Immunohistochemical analysis of pSmad2/3 in tibia subchondral bone. Consistent with increased levels of active TGFβ1 in OA subchondral bone, pSmad2/3+ cell number was also increased in OA subchondral bone. n=10; *$P<0.05$; **$P<0.01$ vs. healthy. Oac+: OA subchondral bone covered with cartilage, Oac−: OA subchondral bone without cartilage.

FIGS. 8A-8G: Computerized simulation of articular cartilage stress distribution changes with subchondral bone expansion or subchondral bone material properties in human tibia. (FIGS. 8A-8B) An established FE model of human tibial plateau was used for simulation. The subchondral plate modulus Lateral Stress distribution in tibial articular cartilage) p subchondral bone size expansion is simulated based on previously published data from large-scale clinical OA studies 1-3 in order to predict overlying articular cartilage stress distribution changes. As compared with the normal situation (FIG. 8C), an incremental increase of 1% (FIG. 8D) or 2% (FIG. 8E) in subchondral bone size will lead to a significant increase in the stress of articular cartilage. (FIG. 8F) The stress distribution in human articular tibial cartilage with the normal subchondral stiffness modulus under dynamic compression loading of body weight 4. Point I is the peak stress in the medial condyle articular cartilage; Point II is the peak stress in lateral condyle. (FIG. 8G) According to previously published data of bone mineral density with OA progression 3, it is estimated that the increment of subchondral plate stiffness modulus by 10% or 20% will result in significant increase in peak stress on articular surface for both medial and lateral condyles.

(FIG. 9A) Representative images of immunohistochemical analysis of TRAP (red) y) and osterix (brown) staining in bone marrow area of tibial subchondral bone in ACLT OA mouse model at 0 (left column), 14 (middle column), and 30 days (right column) after ACLT surgery. (FIG. 9B) Histomorphometry analysis atlas of overall distribution of osterix and TRAP positive cells in bone marrow of tibial subchondral bone. TRAP positive cells (osteoclasts) represent the bone remodeling surface and are indicated as white lines; osterixpositive cells are indicated as green dots. As compared with those in Day 0, osteoclasts were increased at day 14 and reduced to baseline by Day 30; in contrast, osterix-positive cells were increased in tibial subchondral bone marrow at Day 30. n=8.

(FIG. 10A) Safranin O staining of tibia articular cartilage and adjacent subchondral bone of knee joints from ACLT mice treated with different doses of TβRI inhibitor 2 month after ACLT surgery. (FIG. 10B) 3D reconstructed μCT images of subchondral bone knee joints from ACLT. Quantitative analysis of μCT parameters of subchondral bone at 30 and 60 days post ACLT surgery: bone volume/tissue volume (BV/TV) (FIG. 10C), tissue volume (TV) (FIG. 10D), and trabecular pattern factor (Tb. Pf) (FIG.

10E). Dotted line indicates the average TV at 30 days post ACLT. Sham-operated mice maintained articular cartilage and subchondral bone structure. In contrast, the ACLT mice treated with vehicle lost most of articular cartilage and had altered subchondral bone morphology. TβRI inhibitor of 1 mg/kg rescued the subchondral bone changes and prevented the degeneration of articular cartilage. Lower doses (0.1 and 0.5 mg/kg) of inhibitor did not completely rescue bone structure, nor prevent the degeneration of articular cartilage. Higher doses (2.5 and 5 mg/kg) of inhibitor could rescue the bone structure but also caused deleterious effects on the articular cartilage, likely because TGFβ1 signaling is essential for maintenance of the articular cartilage. While treatment with the inhibitor did not change BV/TV (c), treatment with high doses of the inhibitor (1, 2.5, and 5 mg/kg) inhibited the increase in TV (d) and decreased Tb. Pf induced by ACLT surgery (e). n=10, *P<0.05 vs. vehicle group.

Figure 11:
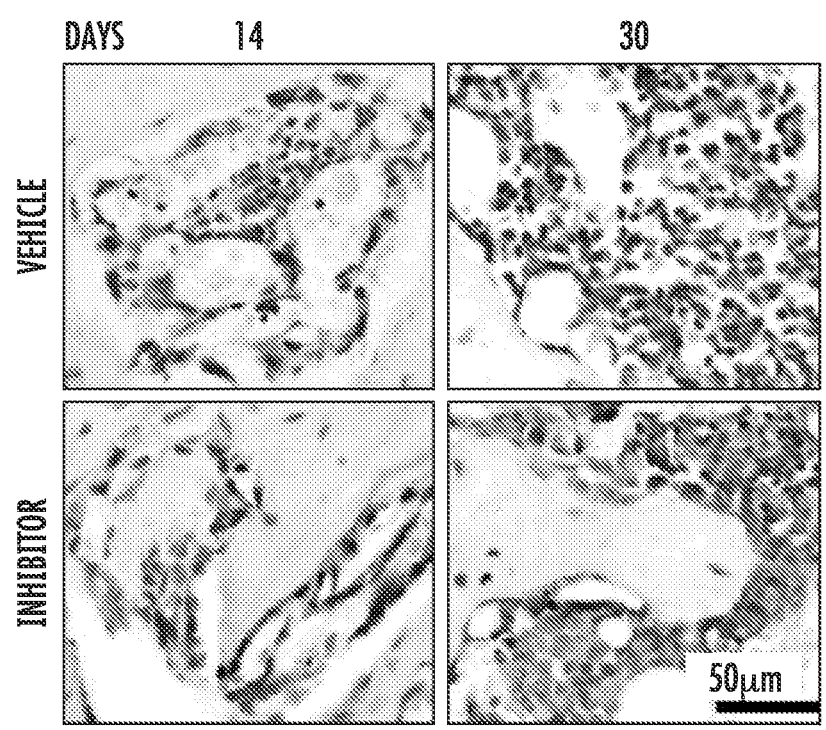
Figure 12A:
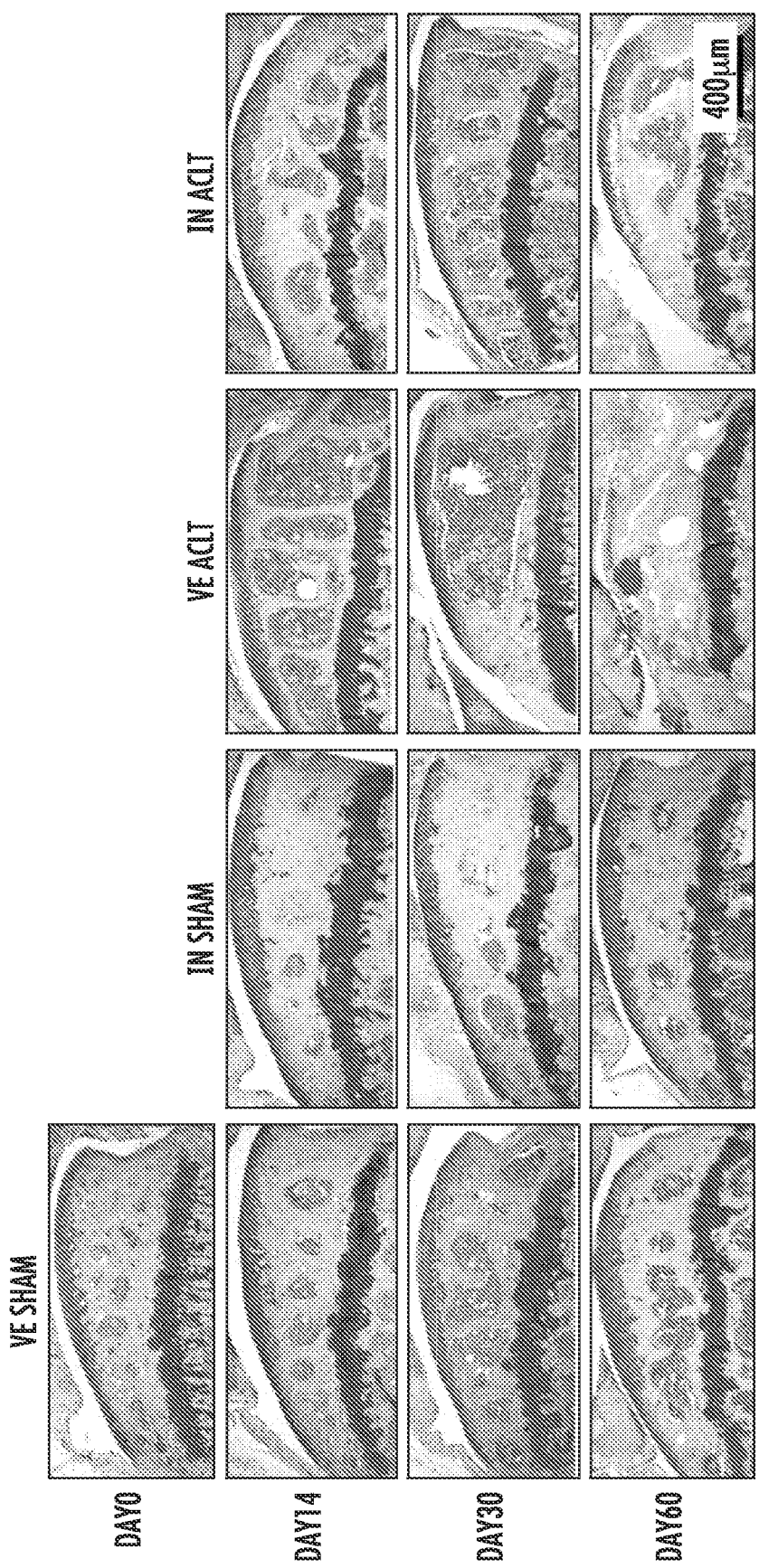
Figure 12B:
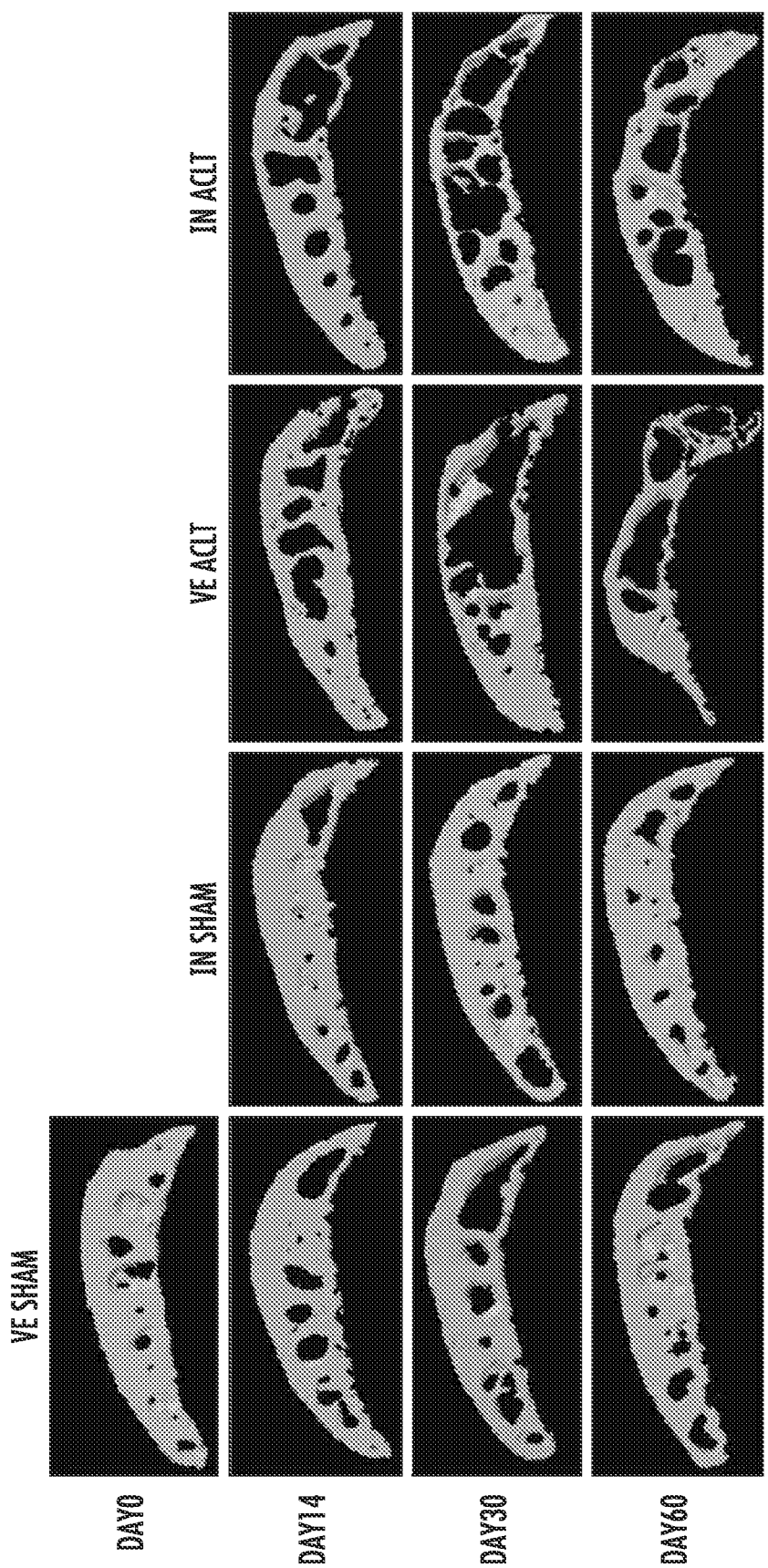
Figure 12C:
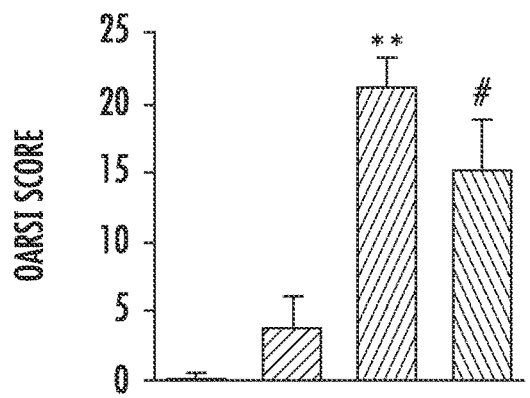
Figure 12D:
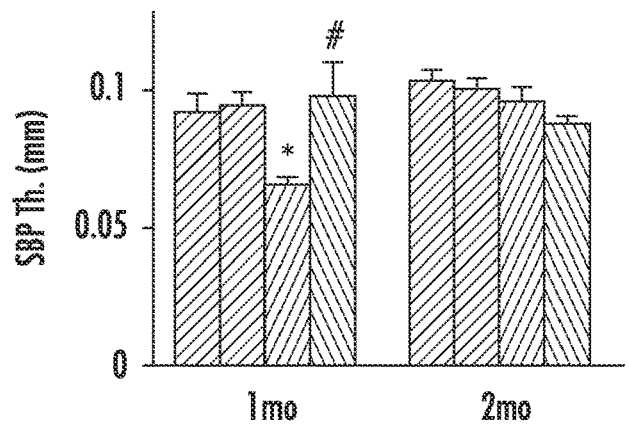
Figure 12E:
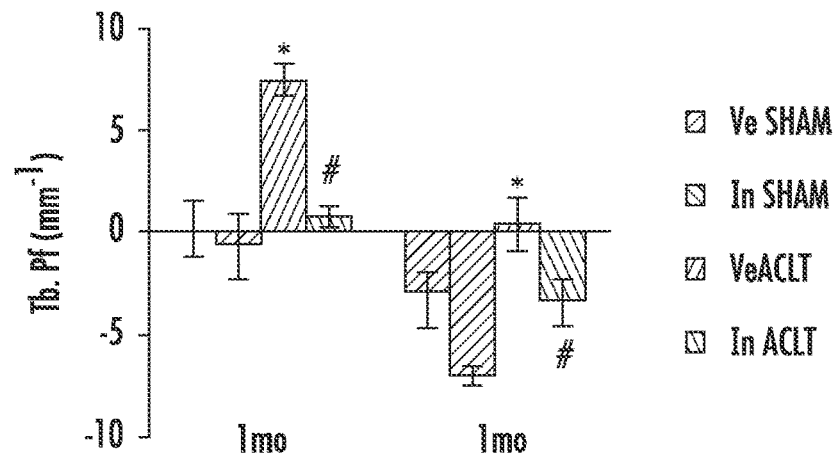

FIG. 11: Effect of TβRI inhibitor treatment on cartilage TGFβ downstream signaling and subchondral bone remodeling in ACLT mice. (b) Immunostaining demonstrated that osterix+osteoprogenitors (brown) did not co-localize with TRAP+ osteoclasts (pink) in ACLT-Vehicle treated mice (top panels at 14 and 30 days). However, co-localization of osterix and TRAP was seen in ACLT-TβRI inhibitor treated mice (bottom panels). n=8.

FIGS. 12A-12E: TβRI inhibitor treatment improved subchondral bone architecture and attenuated articular cartilage degeneration in 9 month old mice. (FIG. 12A) Safranin O staining of tibia articular cartilage and subchondral bone of mice sacrificed at 0, 14, 30, and 60 days post sham or ACLT surgery and treated with either vehicle or TβRI inhibitor (SB505124-1 mg/kg) daily beginning 3 days post-surgery for 1 month. For those mice analyzed at earlier time points, the mice were treated until sacrificed. (FIG. 12B) 3D μCT images of subchondral bone of knee joints. The sham operated mice maintained articular cartilage and subchondral bone structure throughout the duration of the experiment. TβRI inhibitor treatment in sham-operated mice did not have significant effect on articular cartilage and only a slight increase in subchondral bone volume fraction. The degeneration of articular cartilage and disrupted subchondral bone morphology and structure in vehicle treated ACLT mice significantly progressed over 2 months. TβRI inhibitor treatment improved subchondral bone architecture and attenuated the articular cartilage degeneration compared to the ACLT-Vehicle treated mice at similar time points. (FIG. 12C) OARSI score based on the histology analysis. Quantitative analysis of structural parameters by μCT analysis: (FIG. 12D) thickness of subchondral bone plate (SBP) and (FIG. 12E) trabecular pattern factor (Tb. Pf). The thickness of the subchondral bone plate was decreased in ACLT-Vehicle treated mice at 1 month post-surgery, but remained normal in the ACLT-inhibitor treated mice compared to the sham-operated controls. TβRI inhibitor treatment also decreased the trabecular pattern factor relative to ACLT-Vehicle treated mice at 1 and 2 months post ACLT indicating improvement in bone micro-architecture and connectivity. n=8, **P<0.01 vs. vehicle sham, # P<0.05 vs. vehicle ACLT. Ve-Sham: vehicle treated in sham operated; In-Sham: TβRI inhibitor treat in sham operated; Ve-ACLT: vehicle treated in ACLT operated; In-ACLT: TβRI inhibitor treated in ACLT operated mice.

FIGS. 13A-13C: Perfusion of subchondral bone of ACLT mice. (FIG. 13A) Representative MRI T2 weighted image of knee joint from ACLT mice. (FIG. 13B) Validation of the perfusion measurement. Perfusion rates at different sites (marked in (FIG. 13A)) in subchondral bone were quantified. As showed in (FIG. 13B), the perfusion rates were high in tibia, femur and bone marrow where blood was well supplied. The perfusion rates were low in muscle where blood supply was low. (FIG. 13C) Perfusion in subchondral bone of ACLT mice was significantly increased at 1 month, then decreased close to, but still higher than, healthy subchondral bone by 2 months after ACLT surgery. n=8.

Figure 14:
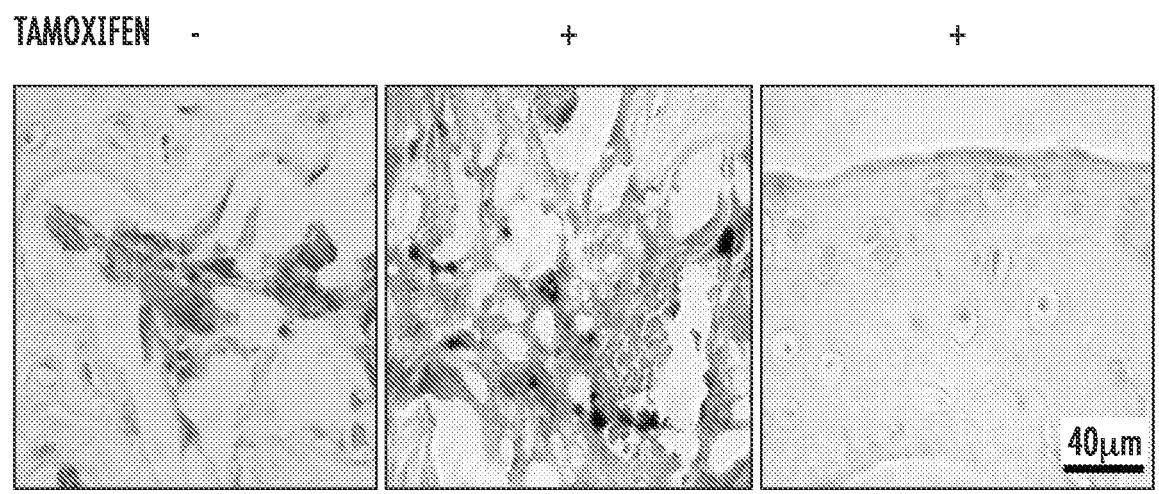

FIG. 14: β-gal positive cell distributions in tibial subchondral bone and articular cartilage of Nestin-CreER::Rosa26-lacZfl/fl mice 1 month post ACLT surgery. Mice homozygous for the Gtrosa26tm1Sor targeted mutation were used to test the cellular expression pattern of the Nestin-Cre transgene. Once induced by tamoxifen, Cre expression results in the removal of a loxP-flanked stop sequence that prevents expression of a lacZ gene. Therefore, X-gal staining for LacZ (blue) is permanently expressed in Nestin-Cre expressing cells and their daughter populations. β-gal positive cells were detected in subchondral bone marrow cavity (2nd panel) but not detected in the articular cartilage after tamoxifen induction 1 mo post ACLT (3rd panel). n=8.

FIGS. 15A-15H: Formation of osteoid islets in the subchondral TβRI inhibitor reduced uncoupled bone formation and angiogenesis in ACLT mice. (FIG. 15A) Immunofluorescent or immunohistochemical analysis and quantification of nestin (red) and osterix (brown) in tibial subchondral bone collected one month after sham operation treated with vehicle (Sham), ACLT operated treated with vehicle (Vehicle), or ACLT operated treated with TβRI inhibitor (Inhibitor). DAPI stains nuclei (blue) (top). Scale bars, 50 μm. (FIG. 15B) Immunohistochemical analysis of osteocalcin (brown) and trichrome staining in tibial subchondral bone sections. Scale bars, 50 μm. Open arrowheads indicating osteocalcin$^+$ cells and close arrowheads indicating osteoid. (FIG. 15C) Flow cytometry analysis of nestin and osterix in bone marrow from mouse subchondral bone. (FIG. 15D) Calcein (green) and xylenol orange (orange) fluorescent double labeling. Scale bar, 100 μm. (FIG. 15E) Immunohistochemical analysis and quantification of CD31 (brown) in subchondral bone. Scale bar, 50 μm. (FIG. 15F) CT-based micro-angiography of the tibia subchondral bone and quantification of subchondral bone vessel volume (VV) and vessel number (VN), Scale bar, 500 μm. (FIG. 15G) Perfusion rate obtained via T2 weighted MRI scanning with contrast. (FIG. 15H) Representative MRI T1 weighted images. Red arrow indicates bone marrow lesion. n=8-12; *P<0.05 vs. sham; #P<0.05 vs. vehicle.

Figure 16A:
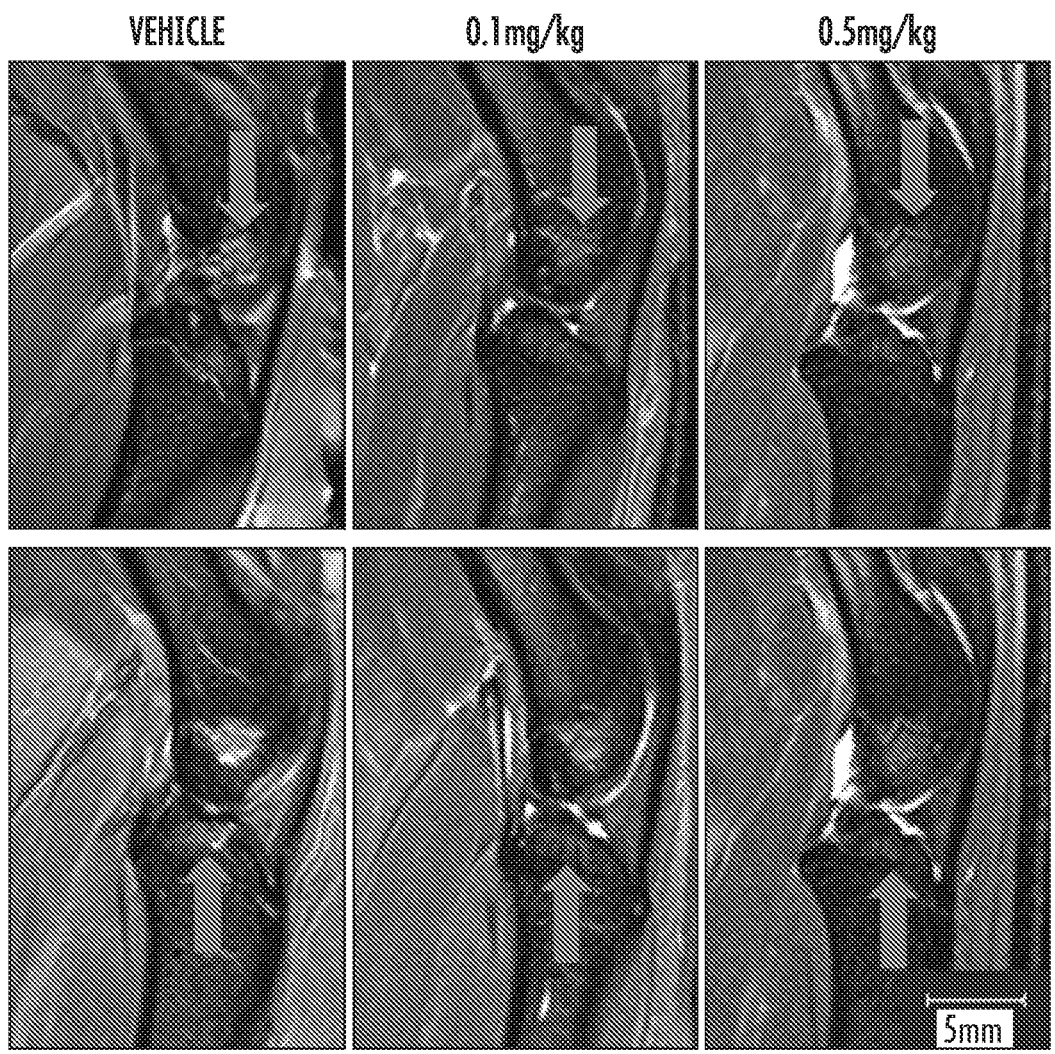
Figure 16B:
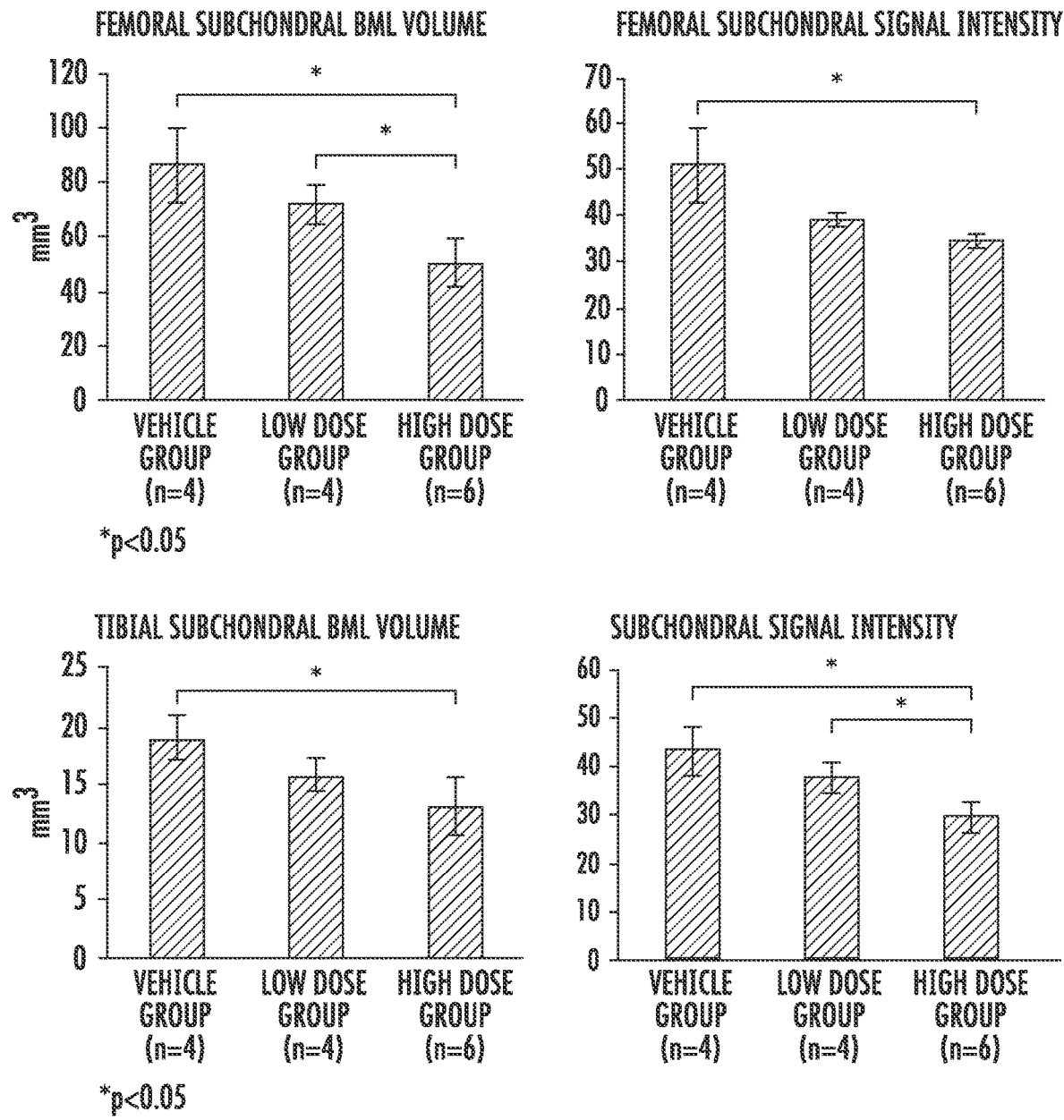

FIGS. 16A-16B: Subchondral bone marrow bone lesions in the knee joints of Dunkin Hartley guinea pig spontaneous osteoarthritis was inhibited when TGFβ type I receptor inhibitor was injected for 3 months, the bone marrow lesions were significantly reduced. (FIG. 16A) MRI scanning of knee joints of the guinea pig with different dose of TβRI inhibitor or vehicle treatment for 3 months. Red arrows pointing the bone marrow lesions in the subchondral bone of distal femur (upper row) or tibiae plateau (lower row). (FIG. 16B) Quantitative analysis of the bone marrow lesion intensity.

DETAILED DESCRIPTION OF THE INVENTION

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Articular cartilage degeneration is the primary concern in osteoarthritis, which has recently been attributed to hypoxia-inducible factor-2α (HIF-2α) and complement component 5 (C5), in addition to the well-established ADAMTS5 and matrix metalloproteinase 13 (MMP13). Homeostasis and integrity of articular cartilage rely on its biochemical and biomechanical interplay with subchondral bone and other joint tissues. Subchondral bone provides the mechanical support for overlying articular cartilage during the movement of joints and undergoes constant adaptation in response to changes in the mechanical environment through modeling or remodeling. In the situation of instability of mechanical loading on weight-bearing joints, such as occurs with ligament injury, excessive body weight, or weakening muscles during aging, the subchondral bone and calcified cartilage zone undergo changes. For instance, rupture of anterior cruciate ligament (ACL) increases the risk of knee osteoarthritis, and approximately 20-35% of individuals with osteoarthritis are estimated to have had an incidental ACL tear. Clinically, osteophyte formation, subchondral bone sclerosis, disruption of tidemark accompanied by angiogenesis at the osteochondral junction, and articular cartilage degeneration are characteristics of osteoarthritis. Bone marrow lesions are closely associated with pain and implicated to predict the severity of cartilage damage in osteoarthritis. In healthy articular cartilage, matrix turnover remains at relatively low rates and chondrocytes resist proliferation and terminal differentiation. During progression of osteoarthritis, type X collagen, alkaline phosphatase, Runt-related transcription factor 2 (RUNX2), and MMP13 are expressed in articular chondrocytes with decreased proteoglycans and expanded calcified cartilage zones in articular cartilage. However, the exact mechanism underlying the potential contributions of subchondral bone to articular cartilage degeneration during osteoarthritis progression is largely unknown.

The role of TGF-β in the pathogenesis of osteoarthritis has drawn more and more attention in recent years. TGF-β is essential for maintenance of articular cartilage metabolic homeostasis and structural integrity. TGF-β1 stimulates chondrocyte proliferation, and knockout of TGF-β1 or interruption of TGF-β signaling in the articular cartilage results in loss of proteoglycans and cartilage degeneration in mice. The elevated ALK1-Smad1/5 vs. ALK5-Smad2/3 ratio in articular cartilage might contribute to pathogenesis of osteoarthritis. Several groups have demonstrated that ablation of endogenous TGF-β1 activity reduces osteophyte formation in vivo but aggravates articular cartilage degeneration in osteoarthritis animal models. We have previously shown that TGF-β1 is activated during osteoclastic bone resorption and induces the migration of bone marrow MSCs to resorption pits for new bone formation serving as a coupling factor. In this study, we investigated the role of TGF-β1 on subchondral bone pathology and articular cartilage degeneration during progression of osteoarthritis. We found that inhibition of TGF-β1 activity in the subchondral bone attenuated its pathological changes and reduced degeneration of articular cartilage in different osteoarthritis animal models.

I. Definitions

The following definitions are used throughout this specification. Other definitions are embedded within the specification for ease of reference.

"Agent" refers to all materials that may be used as or in pharmaceutical compositions, or that may be compounds such as small synthetic or naturally derived organic compounds, nucleic acids, proteins, polypeptides/peptides, antibodies, fragments, isoforms, variants, or other materials that may be used independently for such purposes, all in accordance with the present invention.

Peptides can be useful as agents. The term "peptide" is used broadly herein to refer to a molecule containing two or more amino acids or amino acid analogs (or modified forms thereof) linked by peptide bonds. As such, peptide agents can contain one or more D-amino acids and/or L-amino acids: and/or one or more amino acid analogs, for example, an amino acid that has been derivatized or otherwise modified at its reactive side chain. In addition, one or more peptide bonds in the peptide can be modified, and a reactive group at the amino terminus or the carboxy terminus or both can be modified. Peptides containing D-amino acids, or L-amino acid analogs, or the like, can have improved stability to a protease, an oxidizing agent or other reactive material the peptide may encounter in a biological environment. Further, the stability of a peptide agent (or test agent) can be improved by generating (or linking) a fusion protein comprising the peptide and a second polypeptide (e.g., an Fc domain of an antibody) that increases the half-life of the peptide agent in vivo. Peptides also can be modified to have decreased stability in a biological environment, if desired, such that the period of time the peptide is active in the environment is reduced.

Antibodies provide an example of peptides useful as agents in the present invention. As used herein, the term "antibody" is used in its broadest sense to include polyclonal and monoclonal antibodies, as well as antigen binding fragments of such antibodies. Antibodies are characterized, in part, in that they specifically bind to an antigen, particularly to one or more epitopes of an antigen such as a TGF-beta (e.g., TGF-beta 1, etc.) or TGF-beta receptor (TGF-beta RI, RII, etc.). The terms "specifically binds," "binds specifically," "specific binding activity" and the like, when used in reference to an antibody, means that an interaction of the antibody and a particular epitope has a dissociation constant of at least about $1 \times 10^{-6}$ M, generally at least about $1 \times 10^{-7}$ M, usually at least about $1 \times 10^{-8}$ M, and particularly at least about $1 \times 10^{-9}$ M or $1 \times 10^{-10}$ M or less. As such, Fab, F(ab')$_2$, Fd and Fv fragments of an antibody that retain specific binding activity are included within the definition of an antibody. In certain embodiments, the present invention utilizes antibodies that directly or indirectly block or neutralize TGF-beta. In specific embodiments, an antibody against TGF-beta 1 is used. Such antibodies are commercially available.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains See Huse et al. 246 SCIENCE 1275-1281 (1989). These and other methods of making, for example, chimeric, humanized, CDR-grafted, single chain, and bifunctional antibodies are well known in the art. See generally, Harlow and Lane, ANTIBODIES. A LABORATORY MANUAL (Cold Spring Harbor Laboratory Press, 1999); Borrabeck, Antibody Engineering, 2d ed. (Oxford University Press 1995); Winter and Harris, 14 IMMUNOL. TODAY 243-46 (1993); Hilyard et al, PROTEIN ENGINEERING. A PRACTICAL APPROACH (IRL Press 1992); and Ward et al., 341 NATURE 544-46 (1989).

A "small molecule" refers to a composition that has a molecular weight of less than 3 about kilodaltons (kDa), less than about 1.5 kilodaltons, or less than about 1 kilodalton. Small molecules may be nucleic acids, peptides, polypeptides, peptidomimetics, carbohydrates, lipids or other organic (carbon-containing) or inorganic molecules. A "small organic molecule" is an organic compound (or organic compound complexed with an inorganic compound (e.g., metal)) that has a molecular weight of less than about 3 kilodaltons, less than about 1.5 kilodaltons, or less than about 1 kDa.

As used herein, a "subject" or "patient" means an individual and can include domesticated animals, (e.g., cats, dogs, etc.); livestock (e.g., cattle, horses, pigs, sheep, goats, etc.), laboratory animals (e.g., mouse, rabbit, rat, guinea pig, etc.) and birds. In one aspect, the subject is a mammal such as a primate or a human. In particular, the term also includes mammals diagnosed with, or at risk of developing, osteoarthritis.

As used herein, the term "effective," means adequate to accomplish a desired, expected, or intended result. More particularly, a "therapeutically effective amount" as provided herein refers to an amount of a TGF-beta inhibitor of the present invention, either alone or in combination with another therapeutic agent (e.g., another TGF-beta inhibitor and/or a different therapeutic agent), necessary to provide the desired therapeutic effect, e.g., an amount that is effective to prevent, alleviate, or ameliorate symptoms of disease or prolong the survival of the subject being treated. In a specific embodiment, the term "therapeutically effective amount" as provided herein refers to an amount of a TGF-beta inhibitor, necessary to provide the desired therapeutic effect, e.g., an amount that is effective to prevent, alleviate, or ameliorate symptoms of disease or condition, or prolong the survival of the subject being treated. In a more specific embodiment, a therapeutically effective amount of a TGF-beta inhibitor refers to an amount necessary to treat or prevent osteoarthritis, prevent onset of ligament injury-induced osteoarthritis, prevent onset of osteoarthritis in an unstable joint, or reduce the degeneration of articular cartilage in a joint.

As would be appreciated by one of ordinary skill in the art, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

As used herein, the terms "treatment," "treating," and the like, refer to obtaining a desired pharmacologic and/or physiologic effect. The effect may be prophylactic in terms of completely or partially preventing a disease, condition or symptom thereof and/or may be therapeutic in terms of a partial or complete cure for a disease or condition and/or adverse effect attributable to the disease or condition. "Treatment," as used herein, covers any treatment of a disease or condition in a subject, particularly in a human, and includes: (a) preventing the disease or condition from occurring in a subject which may be predisposed to the disease but has not yet been diagnosed as having it; (b) inhibiting the disease or condition, i.e., arresting its development; and (c) relieving the disease or condition, e.g., causing regression of the disease or condition, e.g., to completely or partially remove symptoms of the disease or condition.

II. TGF-Beta Inhibitors

In certain embodiments, the methods of the present invention utilize a TGF-beta inhibitor. The term "TGF-beta" refers to one or more members of the transforming growth factor-beta family of proteins, e.g., TGF-beta 1, TGF-beta 2, and TGF-beta 3, which are pleiotropic modulators of cell growth and differentiation, embryonic and bone development, extracellular matrix formation, hematopoiesis, immune and inflammatory responses. Other members of this superfamily include activin, inhibin, bone morphogenic protein, and Mullerian inhibiting substance. TGF-beta initiates an intracellular signaling pathway leading ultimately to the expression of genes that regulate the cell cycle, control proliferative responses, or relate to extracellular matrix proteins that mediate outside-in cell signaling, cell adhesion, migration, and intercellular communication. It is understood that the use of the term "TGF-beta" refers to one or more members of the superfamily. In certain embodiments, the term "TGF-beta" refers to TGF-beta 1.

The term "TGF-beta inhibitor" refers to an agent having the ability to directly or indirectly inhibit a biological function of TGF-beta. Thus, TGF-beta inhibitors include, but are not limited to, inhibitors (e.g., blocking (neutralizing) antibodies) specific for TGF-beta, soluble TGF-beta receptors (which would competitively inhibit TGF-beta), membrane-bound TGF-beta receptors, protease inhibitors that inactivate a protease responsible for activating a precursor TGF-beta into mature TGF-beta, inhibitors (e.g., antibodies or small molecules) specific to TGF-beta receptors (Types I, II or III) that prevent TGF-beta binding to the receptor, siRNA or antisense RNA that block expression of TGF-beta or combinations of the foregoing.

Accordingly, the term "TGF-beta inhibitor" is intended to encompass naturally occurring inhibitors including, but not limited to, chordin and noggin proteins, Cerebus, Gremlin, DAN and other members of the DAN protein family, and follistatin. Small molecule TGF-beta inhibitors include but are not limited to, SB43154 (GlaxoSmithKline, King of Prussia, Pa.), LY 2157299 (Axon Medichem, Groningen, NL) and TGF-beta receptor kinase inhibitors such as [3-(pyridine-2yl)-4-(4-quinonyl)]-1H pyrazole and SD-208

(Scios, Inc. Fremont, Calif.), or TGF-beta 2 inhibitor AP 12009 (Antisense Pharma, Regensburg, Bavaria), Pirfenidone (InterMune Inc., Brisbane, Calif.). See Yingling et al., 3 NATURE REVIEWS DRUG DISCOVERY 1011-22 (2004). In other embodiments, a TGF-beta inhibitor include mannose-6-phosphate (BTG), LF-984, tamoxifen (ethanamine, 2-(4-(1, 2-diphenyl-1-butenyl)phenoxy)-N,N-dimethyl-, (Z)—), pirfenidone (CAS No. 53179-13-8) (MARNAC), tranilast (CAS No. 53902-12-8) (Kissei), IN-1130 (In2Gen), TGF-beta antagonists from Inflazyme (Pharmaprojects No. 6075), TGF-beta receptor kinase inhibitors from Eli Lilly (U.S. Pat. No. 7,511,056; U.S. Patent Publication No. 20080262004), and analogues or derivatives thereof.

TGF-beta inhibitors can be conjugated to molecules that target the heteroconjugate to the site of action. In certain embodiments, the TGF-beta inhibitor can be conjugated to a bisphosphonate or derivatives thereof. In one embodiment, a TGF-beta inhibitor can be conjugated to aldendronate. In another embodiment, the TGF-beta inhibitor can be conjugated to actenol. In yet another embodiment, the TGF-beta inhibitor can he conjugated to zoledronate (ACLASTA®). In certain embodiments, a TGF-beta inhibitor antibody is conjugated to a bisphosphonate or derivatives thereof. In other embodiments, a TGF-beta inhibitor small molecule is conjugated to a bisphosphonate or derivatives thereof. In a specific embodiment, the small molecule comprises halofuginone, kartogenin, SB-505124, or derivatives thereof. In particular embodiments, conjugation can involve a linker. See, e.g., Guan et al., 18 (3) NATURE MEDICINE 456-U159 (2012) and Johnson et al., 336(6082) SCIENCE 717-21 (2012).

The effects of TGF-beta are mediated by the binding of active TGF-beta to specific receptors present on cells, followed by transduction of signal to those cells. TGF-beta inhibitors or antagonists are further defined herein as molecules that inhibit TGF-beta signal transduction. In certain embodiments, molecules that bind TGF-beta and prevent TGF-beta from binding to a TGF-beta receptor will act as TGF-beta antagonists. Such molecules include neutralizing antibodies to TGF-beta. See, e.g., WO 2005/010049; Lucas et al. 145 J. IMMUNOL. 1415-22 (1990) and Dasch et al 142 J. IMMUNOL. 1536-41 (1989). Those skilled in the art recognize various ways in which an antibody derived from one species, for example a mouse, can be engineered in order to be therapeutically useful in a second species, for example a human.

Soluble forms of TGF-beta receptors will also bind TGF-beta and prevent binding to membrane-associated TGF-beta receptors. See Lin et al., 68 CELL 775-85 (1992); and Wang et al., 67 CELL 797-805 (1991). Soluble forms of TGF-beta receptors can be prepared by methods that are known in the art. For example, deletion mutants lacking the transmembrane domain of a TGF-beta receptor can be prepared, which will express a soluble TGF-beta binding protein. See, Miyazono et al., 55 Adv. Immunol. 181 (1994), Similarly, selective TGF-beta receptor inhibitors such as SB431542, LY364947, SD-208, and A-83-01 can be employed.

Other types of TGF-beta antagonists are also known in the art. For example, decorin is a small chondroitin-dermatan sulphate proteoglycan that binds TGF-beta and modulates the activity of this growth factor. See Yamaguchi et al., 346 NATURE 281-84 (1990). Protein kinase inhibitors that block certain biological activities of TGF-beta can be used. See Ohtsuki. & Massague, 12 MOL. CELL BIOL. 261-65 (199). See also Mselle et al., 124 CLIN. IMMUNOL. 69 (2007); Eriksson et al., 56 AM. J. REPROD. IMM. 321 (2006); Eriksson et al., 176 J. IMMUNOL. 6219 (2006); Meadows et al., 6 INT. IMMUNOPHARM. 1020 (2006); Saunier & Akhurst, 6 CURR. CAN. DRUG TARGETS 565 (2006); Tsuchida et al., 6 MINI-REVIEWS MED. CHEM. 1255 (2006); Wira et al., 206 IMMUNOL. REV. 306 (2005); Garba, et al., 168 J. IMMUNOL. 2247 (2002); and Sato et al., 164 J. IMMUNOL. 2285 (2000).

TGF-beta inhibitors can also include peptide agents. These molecules are of peptidic nature, meaning that they comprise alpha-amino acids linked by an amide bond, i.e., the peptidic bond. The term "peptide" is not to be limited to short amino acid chains; it can include chains of more than 50 amino acids in length. As such, the term peptide as used herein encompasses as well polypeptides and proteins. In specific embodiments, a TGF-beta 1 inhibitor peptide may be a peptide described in U.S. Patent Publication No. 20110294734 (see Table 1).

In particular embodiments, a TGF-beta 1 inhibitor peptide has the ability to inhibit a biological function of TGF-beta 1 by interacting with the active form of TGF-beta1. In certain embodiments, for example, although a TGF-beta 1 inhibitor is characterized by its ability to interact with TGF-beta 1, it is understood that the inhibitor might additionally interact with the other mammalian isoforms (e.g., TGF-beta 2 and/or -beta 3). This activity inhibits TGF-beta interaction with the corresponding superfamily receptors, like type I receptors such as activin like kinases ALK1, ALK2, ALK5; type II receptors such as type II TGF-beta receptor (TGF-beta RII); co-receptors such as endoglin and crypto. Additionally, the inhibitors may as well interact with type I receptors like ALK3, ALK4, ALK6, ALK7; type II receptors like ActRII, ActRIIb, BMPRII, MISRII, and TGF-beta RII; co-receptors like RGMa, RGMb, and hemoiuvelin; pseudo-receptors like BAMBJ; signaling components such as chordin, follistatin, leftyl, noggin, sclerostin; and other members in the TGF-beta signal transduction pathway or members shared by the TGF-beta signal transduction pathway and another pathway. Inhibition of TGF-beta activity (e.g., in the subchondral bone) can also be achieved by inhibition of TGF-beta downstream components through siRNA, peptide, or TGF-beta antagonists or negative regulators.

TGF-beta inhibitor peptides may be obtained from a variety of cell sources that synthesize these peptides including, for example, cells transfected with recombinant DNA molecules capable of directing the synthesis or secretion of the peptides. Alternatively, TGF-beta inhibitor peptides may be synthesized by chemical synthetic methods, including but not limited to, solid phase peptide synthesis. The peptides are as well commercially available, for instance P144 is supplied by Sigma-Genosys, Ltd. (Cambridge, UK).

III. Pharmaceutical Compositions and Administration

Accordingly, a pharmaceutical composition of the present invention may comprise an effective amount of a TGF-beta inhibitor. As used herein, the term "effective," means adequate to accomplish a desired, expected, or intended result. More particularly, an "effective amount" or a "therapeutically effective amount" is used interchangeably and refers to an amount of at least one TGF-beta inhibitor, perhaps in further combination with yet another therapeutic agent, necessary to provide the desired "treatment" (defined herein) or therapeutic effect, e.g., an amount that is effective to prevent, alleviate, treat or ameliorate symptoms of a disease or condition or prolong the survival of the subject being treated. In particular embodiments, the pharmaceutical compositions of the present invention are administered in a therapeutically effective amount to treat patients having osteoarthritis or patients at risk of developing osteoarthritis including patients suffering from a ligament injury. As would be appreciated by one of ordinary skill in the art, the exact TGF-beta inhibitor dose amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

The pharmaceutical compositions of the present invention are in biologically compatible form suitable for administration in vivo for subjects. The pharmaceutical compositions can further comprise a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the TGF-beta inhibitor is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water may be a carrier when the pharmaceutical composition is administered orally. Saline and aqueous dextrose may be carriers when the pharmaceutical composition is administered intravenously. Saline solutions and aqueous dextrose and glycerol solutions may be employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The pharmaceutical composition may also contain minor amounts of wetting or emulsifying agents, or pH buffering agents.

The pharmaceutical compositions of the present invention can take the form of solutions, suspensions, emulsions, tablets, pills, capsules, powders, sustained-release formulations and the like. The composition can be formulated as a suppository, with traditional binders and carriers such as triglycerides, Oral formulation may include standard carriers such as pharmaceutical grades of mannitol, lactose, starch, magnesium stearate, sodium saccharine, cellulose, magnesium carbonate, etc. In a specific embodiment, a pharmaceutical composition comprises an effective amount of a TGF-beta inhibitor together with a suitable amount of a pharmaceutically acceptable carrier so as to provide the form for proper administration to the patient. The formulation should suit the mode of administration.

The pharmaceutical compositions of the present invention may be administered by any particular route of administration including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocadial, intraosteal, intraosseous, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means. Most suitable routes are oral administration or injection. In certain embodiments, an injection into the affected joint area is preferred.

In general, the pharmaceutical compositions comprising a TGF-beta inhibitor may be used alone or in concert with other therapeutic agents at appropriate dosages defined by routine testing in order to obtain optimal efficacy while minimizing any potential toxicity. The dosage regimen utilizing a pharmaceutical composition of the present invention may be selected in accordance with a variety of factors including type, species, age, weight, sex, medical condition of the patient; the severity of the condition to be treated; the route of administration; the renal and hepatic function of the patient; and the particular pharmaceutical composition employed. A physician of ordinary skill can readily determine and prescribe the effective amount of the pharmaceutical composition (and potentially other agents including therapeutic agents) required to prevent, counter, or arrest the progress of the condition.

Optimal precision in achieving concentrations of the therapeutic regimen (e.g., pharmaceutical compositions comprising at least one TOT-beta inhibitor (and optionally in combination with another therapeutic agent)) within the range that yields maximum efficacy with minimal toxicity may require a regimen based on the kinetics of the pharmaceutical composition's availability to one or more target sites. Distribution, equilibrium, and elimination of a pharmaceutical composition may be considered when determining the optimal concentration for a treatment regimen. The dosages of a pharmaceutical composition disclosed herein may be adjusted when combined to achieve desired effects. On the other hand, dosages of the pharmaceutical compositions and various therapeutic agents may be independently optimized and combined to achieve a synergistic result wherein the pathology is reduced more than it would be if either was used alone.

In the case of injections, it is usually convenient to give in an amount of about 0.0001 µg-30 mg, about 0.01 ng-20 mg or about 0.0140 mg per day to adults (at about 60 kg). In the case of other animals, the dose calculated for 60 kg may be administered as well.

Doses of a pharmaceutical composition of the present invention can optionally include about 0.0001 µg to about 1,000 mg/kg/administration, or about 0.001 µg to about 100.0 mg/kg/administration, from about 0.01 µg to about 10 mg/kg/administration, from about 0.1 µg to about 10 mg/kg/administration, including, but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration or any range, value or fraction thereof.

As a non-limiting example, treatment of patients can be provided as a one-time or periodic dosage of a composition of the present invention of about 0.1 ng to about 100 mg/kg such as 0.0001, 0.001, 0.01, 0.1 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Specifically, the pharmaceutical compositions of the present invention may be administered at least once a week over the course of several weeks. In one embodiment, the pharmaceutical compositions are administered at least once a week over several weeks to several months. In another embodiment, the pharmaceutical compositions are administered once a week over four to eight weeks. In yet another embodiment, the pharmaceutical compositions are administered once a week over four weeks.

More specifically, the pharmaceutical compositions may be administered at least once a day for about 2 days, at least once a day for about 3 days, at least once a day for about 4 days, at least once a day for about 5 days, at least once a day for about 6 days, at least once a day for about 7 days, at least once a day for about 8 days, at least once a day for about 9 days, at least once a day for about 10 days, at least once a day for about 11 days, at least once a day for about 12 days, at least once a day for about 13 days, at least once a day for about 14 days, at least once a day for about 15 days, at least once a day for about 16 days, at least once a day for about 17 days, at least once a day for about 18 days, at least once a day for about 19 days, at least once a day for about 20 days, at least once a day for about 21 days, at least once a day for about 22 days, at least once a day for about 23 days, at least once a day for about 24 days, at least once a day for about 25 days, at least once a day for about 26 days, at least once a day for about 27 days, at least once a day for about 28 days, at least once a day for about 29 days, at least once a day for about 30 days, or at least once a day for about 31 days.

Alternatively, the pharmaceutical compositions may be administered about once every day, about once every 2 days, about once every 3 days, about once every 4 days, about once every 5 days, about once every 6 days, about once every 7 days, about once every 8 days, about once every 9 days, about once every 10 days, about once every 11 days, about once every 12 days, about once every 13 days, about once every 14 days, about once every 15 days, about once every 16 days, about once every 17 days, about once every 18 days, about once every 19 days, about once every 20 days, about once every 21 days, about once every 22 days, about once every 23 days, about once every 24 days, about once every 25 days, about once every 26 days, about once every 27 days, about once every 28 days, about once every 29 days, about once every 30 days, or about once every 31 days.

The pharmaceutical compositions of the present invention may alternatively be administered about once every week, about once every 2 weeks, about once every 3 weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks.

Alternatively, the pharmaceutical compositions of the present invention may be administered about once every month, about once every 2 months, about once every 3 months, about once every 4 months, about once every 5 months, about once every 6 months, about once every 7 months, about once every 8 months, about once every 9 months, about once every 10 months, about once every 11 months, or about once every 12 months.

Alternatively, the pharmaceutical compositions may be administered at least once a week for about 2 weeks, at least once a week for about 3 weeks, at least once a week for about 4 weeks, at least once a week for about 5 weeks, at least once a week for about 6 weeks, at least once a week for about 7 weeks, at least once a week for about 8 weeks, at least once a week for about 9 weeks, at least once a week for about 10 weeks, at least once a week for about 11 weeks, at least once a week for about 12 weeks, at least once a week for about 13 weeks, at least once a week for about 14 weeks, at least once a week for about 15 weeks, at least once a week for about 16 weeks, at least once a week for about 17 weeks, at least once a week for about 18 weeks, at least once a week for about 19 weeks, or at least once a week for about 20 weeks.

Alternatively the pharmaceutical compositions may be administered at least once a week for about 1 month, at least once a week for about 2 months, at least once a week for about 3 months, at least once a week for about 4 months, at least once a week for about 5 months, at least once a week for about 6 months, at least once a week for about 7 months, at least once a week for about 8 months, at least once a week for about 9 months, at least once a week for about 10 months, at least once a week for about 11 months, or at least once a week for about 12 months.

The pharmaceutical compositions may further be combined with one or more additional therapeutic agents. The determination of the identity and amount of the pharmaceutical compositions for use in the methods of the present invention can be readily made by ordinarily skilled medical practitioners using standard techniques known in the art. In other specific embodiments, a TGF-beta inhibitor can be administered in combination with an effective amount of another TGF-beta inhibitor, an osteoarthritis therapeutic agent (e.g., a corticosteroid, hyaluronic acid, etc.) or another therapeutic agent.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Human Subjects. After IRB approval, we collected tibial plateau specimens from 78 individuals with osteoarthritis that were undergoing total knee replacement surgery. The specimens were processed for μCT ELISA and histological examination. We purchased healthy knees specimens from the Nation Disease Research Interchange (NDRI) to serves as controls.

Mice. We purchased C57BL/6J (wild type) mice from Charles River. We anesthetized two months old male mice with ketamine and xylazine and then transected the anterior cruciate ligament surgically to induce mechanical instability associated osteoarthritis on the right knee. Sham operations were done on independent mice. For the time-course experiment, operated animals were euthanized at 0, 14, 30, 60 and 90 days post-surgery, n=8-12. For the dosage screening experiment, 2-month-old sham and ACLT-operated mice were assigned into 6 groups, n=10 per group. Beginning three days after surgery, we injected either different doses (0.1, 0.5, 1, 2.5, and 5 mg kg$^{-1}$) of TβRI inhibitor (SB505124, Sigma Aldrich) or the equivalent volume of vehicle (DMSO+PBS) intra-peritoneally daily for 30 days. Mice were euthanized 30 and 60 days post-surgery.

We purchased Nestin-Cre™ER and (ROSA) 26Sortm1Sor/J mice from the Jackson Laboratory. Floxed type II TGF-β receptor (TβRII$^{fl/fl}$) mice were obtained from Dr. Moses' lab. Nestin-Cre™ER mice were crossed with TβRII$^{fl/fl}$ mice. The offspring were intercrossed to generate the following offspring: nestin-Cre™ER::TβRII$^{fl/fl}$, in which Cre was fused with a mutated estrogen receptor that could be activated by Tamoxifen. We determined the genotype of transgenic mice by PCR analyses of genomic DNA isolated from mouse tails. Genotyping for the Cre transgene was performed by PCR with the primers Cre 5' (5'-CAAATAGC-CCTGGCAGAT-3') and Cre 3' (5'-TGATACAAGGGA-CATCTTCC-3'). The loxP TβRII allele was identified with the primerslox1F (5'-TAAACAAGGTCCGGAGCCCA-3') and lox1R (5'-ACTTCTGCAAGAGGTCCCCT-3'). We generated Nestin-Cre™ER::Rosa26-LacZ$^{fl/fl}$ mice by crossing nestin-Cre™ER mice with mice homozygous with a loxP-flanked DNA STOP sequence preventing expression of the downstream lacZ gene. The offspring were then intercrossed to generate the following genotype: Nestin-Cre™ER::Rosa26-LacZ$^{fl/fl}$. We performed sham or ACLT operations on two month-old, male WT, Nestin-Cre™ER:: TβRII$^{fl/fl}$ and Nestin-Cre™ER::Rosa26-lacZ$^{fl/fl}$ male mice. Three days after surgery, we treated each group with 100 mg kg$^{-1}$ body weight of tamoxifen daily for 30 days and sacrificed the mice at either 30 or 60 days after surgery (n=8 per treatment group). CED mice were generated in our laboratory as previously described, in which the CED-derived TGF-β1 mutation (H222D) is specifically expressed by osteoblastic cells driven by a 2.3-kb type I collagen promoter.

Rats. We purchased two month-old male Lewis rats from Charles River. ACLT was conducted as described as above. After ACLT, we made a canal in the medial plateau using a 20G needle. An alginate bead containing 0.1 μg 1D11 (TGF-β1 neutralizing antibody, R&D Systems, Minneapolis, Minn.) or vehicle was embedded in the subchondral bone canal. The canal was then closed with bone wax. We euthanized the animals at 0, 1, 2. and 3 months post-surgery 8 per group). Knee joints were processed for μCT and histological analysis accordingly.

All animals were maintained in the Animal Facility of the Johns Hopkins University School of Medicine. The experimental protocol was reviewed and approved by the Institutional Animal Care and Use Committee of the Johns Hopkins University, Baltimore, Md., USA.

Cell Culture. We obtained green fluorescent protein (GFP)-labeled mouse adult MSCs from the Texas A&M Health Science Center College of Medicine Institute (College Station). We maintained cells (Passage 3-5) Iscove's modified Dulbecco's medium (Invitrogen) supplemented with 10% fetal calf serum (Atlanta Biologicals), 10% horse serum (Thermo Scientific), and (% penicillin-streptomycin (Mediatech). We cultured MSCs in 6-well plates at a density of 1.8×10$^5$ cells per well, then starved them for 6 h followed by TGF-β1 (R&D Systems) and TβRI inhibitor (SB-505124) (Sigma-Aldrich) treatment as indicated.

ELISA and Western Blot, We determined the concentration of active TGF-β1 in the conditioned media by the ELISA Development kit (R&D Systems) according to the manufacturer's instructions. Western blot analyses were conducted on the protein of lysates from in vitro cultured MSCs. The cell lysates were centrifuged and the supernatants were separated by SDS-PAGE and blotted on polyvinylidene fluoride membrane (Bio-Rad Laboratories). Following incubation in specific antibodies, we detected proteins using an enhanced chemiluminescence kit (Amersham Biosciences). We used antibodies recognizing mouse pSmad1/5 (Cell Signaling technology Inc., 1:500), pSmad2 (Cell Signaling technology Inc., 1:1000), Smad1/5/8 (Cell Signaling technology Inc., 1:1000) and Smad2 (Cell Signaling technology Inc., 1:1000) to examine the protein concentrations in the lysates.

Histochemistry, Immunohistochemistry and Histomorphometry. At the time of sacrifice, we resected and fixed the knee joints in 10% buffered formalin for 48 hours, decalcified in 10% ethylenediamine tetraacetic acid (pH 7.4) for 21 days and embedded in paraffin or O.C.T. compound (Sakura Finetek). Four-μm-thick sagittal oriented sections of the knee joint medial compartment were processed for hematoxylin and eosin and sanfranin O-Fast green staining. Tartrate resistant acid phosphatase staining was performed using standard protocol (Sigma-Aldrich). Immunostaining was performed using standard protocol. We incubated sections with primary antibodies to mouse Nestin (Ayes Labs, Inc., 1:300), Osterix (Abeam, 1:600), Osteocalcin (Takara bio 1:200), p-Smad2/3 (Santa Cruz Biotechnology Inc., 1:50), p-Smad1/5 (Abcam, 1:50), ALK1 (Santa Cruz Biotechnology Inc., 1:50), ALK5 (Abeam, 1:50), CD31 (Abeam, 1:100), MMP13 (Abeam, 1:40), and Collagen X (Abeam, (1:80) overnight at 4° C. For immunohistochemical staining, a horse radish peroxidase-streptavidin detection system (Dako) was subsequently used to detect the immunoactivity followed by counterstaining with hematoxylin (Dako). For immunofluorescent staining, secondary antibodies conjugated with fluorescence were added and slides were incubated at room temperature for 1 hour while avoiding light. We microphotographed sections to perform histomorphometric measurements on the entire area of the tibia subchondral bone (Olympus DP71). Quantitative histomorphometric analysis was conducted in a blinded fashion with OsteoMeasureXP Software (OsteoMetrics, Inc). To label mineralization deposition, sequential subcutaneous injections of 1% calcein (Sigma, 15 mg kg$^{-1}$) and 3% xylenol orange (Sigma, 90 mg kg$^{-1}$) in 2% sodium bicarbonate solution was performed. Calcein and xylenol orange were injected 10 days and 2 days respectively before the mice were sacrificed. We counted the number of positively stained cells in whole tibia subchondral bone area per specimen, in five sequential sections per mouse in each group. We calculated OARSI scores as previously described.

Flow cytometry. We divided C57/Bl6 mice into 3 groups (n=10 per group): sham operation with vehicle treatment, ACLT with vehicle treatment and ACLT with TβRI inhibitor (SB505124) treatment. One month after surgery, we sacrificed mice and pooled tibia subchondral bone marrow cells from each group together. Red blood cells were lysed by commercial ACK lysis buffer (Quality Biological, Inc.). After centrifugation, the cell pellet was resuspended and fixed in 4% paraformaldehyde. We then washed cells with 0.1% bovine serum albumin (BSA) in PBS and counted them. 1×10$^6$ cells per milliliter were permeabilized in 0.1% Triton X-100 prior to blocking in 3% FACS buffer (PBS, 3% FBS, 0.1% NaN3 sodium azide) for 30 min on ice. We incubated the cells with Alexa Fluor 647-conjugated Nestin antibody (BD Pharmingen), anti-Osterix (Abcam, 1:400) or isotype control for 1 hour at 37° C. in dark room, and then washed twice with 0.1% BSA in PBS. The cells for Osterix staining were further incubated with fluorochrome-conjugated secondary antibody for 30 minutes on ice. The cells were acquired immediately after washing with 3% FACS buffer. Probes were analyzed using a FACS Calibur flow cytometer and CellQuest software (Becton Dickinson).

In Vivo Micro-MRI. We performed all MRI studies on a horizontal 30 cm bore 9.4T Bruker Biospec preclinical scanner, using a custom-built, single-turn volume coil positioned orthogonal to the $B_0$ magnetic field. Anesthesia was initiated with 4% isoflurane and maintained with a 2% isoflurane/oxygen mixture. We acquired T2-weighted images with a 2D RARE (Rapid Acquisition with Relaxation Enhancement) sequence, TE/TR (echo time/repetition time) =15.17/3000 ms, 35 slices at thickness of 0.35 mm, FONT 1.75×1.75 cm, and matrix size 256×128. We acquired T2-weighted images with a chemical shift selective flit saturation pulse tuned to the fat resonant frequency. All T2-weighted images were processed to a final matrix size of 256×256 with an isotropic resolution of 0.068 mm pixel$^{-1}$. We acquired T1-weighted images with a 3D gradient echo sequence using a 30° flip angle, TE/TR=1.5/8 ms, FOV 1.5×1.5×1.5 cm, and matrix size 128×64×64 before and for 10 minutes after the injection of 0.1 ml 0.1M gadopentetate dimeglumine. All T1-weighted images were processed to a final matrix size of 128×128×128 with an isotropic resolution of 0.12 mm pixel$^{-1}$.

Micro-Computed Tomography (μCT). We dissected knee joints from mice free of soft tissue, fixed overnight in 70% ethanol and analyzed by high resolution μCT (Skyscan1172). We reconstructed and analyzed images using NRecon v1.6 and CTAn v1.9, respectively. Three-dimensional model visualization software, CTVol v2.0, was used to analyze parameters of the trabecular bone in the metaphysis. The scanner was set at a voltage of 50 kVp, a current of 200 μA and a resolution of 5.7 μm per pixel. Cross-sectional images of the tibiae subchondral bone were used to perform three-dimensional histomorphometric analysis. We defined the region of interest to cover the whole subchondral bone medial compartment, and we used a total of ten consecutive images from medial tibial plateau for 3-D reconstruction and analysis. Three-dimensional structural parameters analyzed included: TV: total tissue volume (contains both trabecular and cortical bone), BV/TV: trabecular bone volume per tissue volume, Tb. Th: trabecular thickness, Tb. Sp: trabecular separation, SMI, Conn. Dn: connectivity density, and Tb.Pf: trabecular pattern factor.

CT-Based Microangiography. We imaged blood vessels in bone by angiography of microphil-perfused long bones. Briefly, after we euthanized the animals and opened the thoracic cavity, the inferior vena cava was severed. We flushed the vasculat system with 0.9% normal saline solution containing heparin sodium (100 U mL$^{-1}$) through a needle inserted into the left ventricle. The specimens were pressure fixed with 10% neutral buffered formalin. We washed formalin from the vessels by using heparinized saline solution and then injected a radiopaque silicone rubber compound containing lead chromate (Microfil MV-122; Flow Tech) to label the vasculature. Samples were stored at 4 overnight for contrast agent polymerization. Mouse femurs were dissected from the specimens and soaked for 4 d in 10% neutral buffered formalin to ensure complete tissue fixation. We treated specimens for 48 h in a formic acid-based solution (Cal-Ex II) to decalcify the bone and facilitate image thresholding of the femoral vasculature from the surrounding tissues. Images were obtained using μCTimaging system (Skyscan 1172) at a resolution of 9-μm isotropic voxel size. A threshold of 60 was initially chosen based on visual interpretation of threshold 2D tomograms.

Gait Analysis. We performed automated gait analysis pre-surgery and 2, 4, 6 and 8 weeks post-surgery using a "CatWalk" system (Noldus). All experiments were performed during the same period of the day (1:00 PM to 4:00 PM) and analyzed as previously reported. Briefly, we trained mice to cross the Catwalk walkway daily for 7 days before ACLT or sham operation. During the test, each mouse was placed individually in the Catwalk walkway, Which consists of a glass plate (100×15×0.6 cm) plus two Plexiglas walls, spaced 8 cm apart. The mouse was allowed to walk freely and traverse from one side to the other of the walkway glass plate. Two infrared light beams spaced 90 cm apart were used to detect the arrival of the mouse and to control the start and end of data acquisition. We carried the recordings out when the room was completely dark, with the exception of the light from the computer screen. LED light from an encased fluorescent lamp was emitted inside the glass plate and completely internally reflected. When the mouse paws made contact with the glass plate, light was reflected down and the illuminated contact area was recorded with a high speed color video camera positioned underneath the glass plate connected to a computer running Catwalk software v9.1 (Noldus). Comparison was made between the ipsilateral (left) and the contralateral (right) hind paw in each run of each animal at each time point. Paired t-test was used for statistical analysis.

Statistics. Data are presented as mean±standard deviation. The comparisons for OARSI scores, bone mass and microarchitecture among different groups were performed using multiple-factorial analysis of variance (ANOVA). When ANOVA testing indicated overall significance of main effects and without interaction between them, the difference between individual time points and sites was assessed by post hoc tests. The level of significance was set at P<0.05. All data analyses were performed using SPSS 15.0 analysis software (SPSS Inc).

Results

Example 1: Elevated Active TGF-β and Bone Resorption in Subchondral Bone

Figure 1A:
Figure 1B:
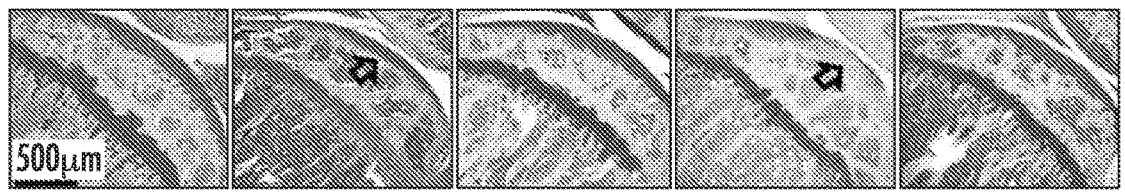
Figure 1C:
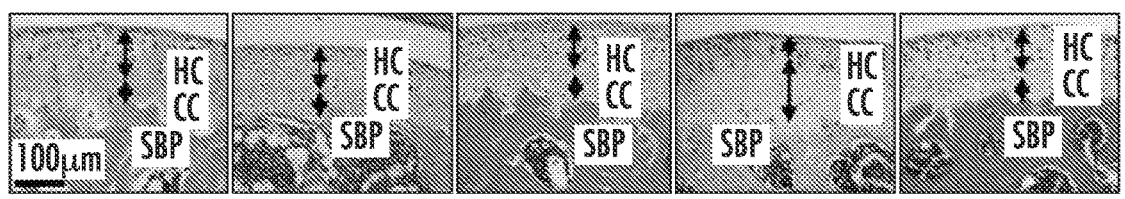
Figure 1D:
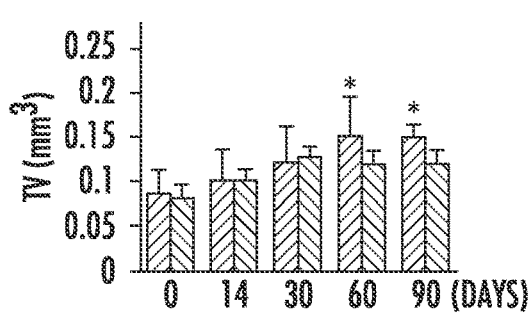
Figure 1D:
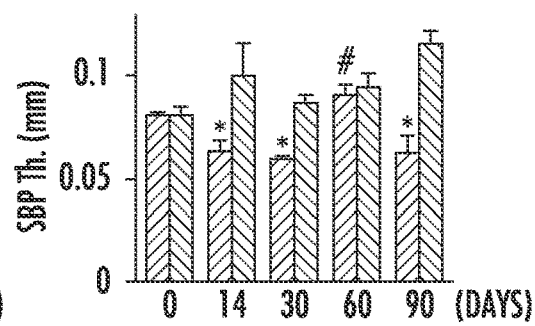
Figure 1D:
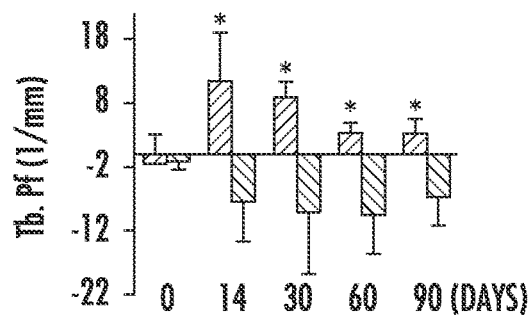
Figure 1D:
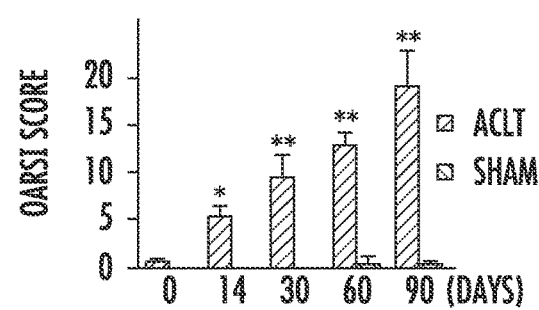

To examine the subchondral bone changes at the onset of osteoarthritis, we transected the ACL in mice to generate a destabilized osteoarthritis animal model and analyzed the effects over time. The tibial subchondral bone volume in ACLT mice dramatically changed relative to sham operated controls post-surgery in three-dimensional μCT analysis (FIG. 1a (top)). The total subchondral bone tissue volume (TV) increased by more than 20% compared to that of sham controls by 2 months post-surgery (FIG. 1b). The thickness of subchondral bone plate (SBP) fluctuated significantly from 14 to 60 days post-surgery with abnormal morphology by 60 days (FIG. 1c). Moreover, the disruption of connectivity and micro-architecture of trabecular bone was indicated by significantly increased trabecular pattern factor (Tb. Pf) in the ACLT mice compared to that of sham operated controls (FIG. 1d), indicating uncoupled bone remodeling. Proteoglycan loss in cartilage was observed 30 days post-surgery and was further aggravated at 60 days (FIG. 1a (center)). Notably, proteoglycan loss was detected at the deep zone of articular cartilage (arrows). H&E staining showed that thickness of the calcified cartilage zone increased with the tidemark moving closer to articular surface. (FIG. 1a (bottom), double arrowed OARSI scores revealed the degeneration of articular cartilage started by 14 days post ACLT and progressed gradually (FIG. 1e). TRAP staining showed that the number of osteoclasts increased in the subchondral bone as early as 7 days post-surgery, and the continued osteoclastic bone resorption generated large bone marrow cavities by 30 days (FIG. 1f (top) and a (top)). Immunostaining demonstrated that post surgery, the number of pSmad2/3+ cells increased by 7 days, maintained at high concentrations until 30 days and then gradually decreased back to baseline by 60 days (FIG. 1f (bottom)). The results suggest that altered mechanical loading induced subchondral bone resorption with elevated TGF-β concentrations in the subchondral bone.

Example 2: Expression of Active TGF-β1 in Bone Induces Osteoarthritis

Figure 2B:
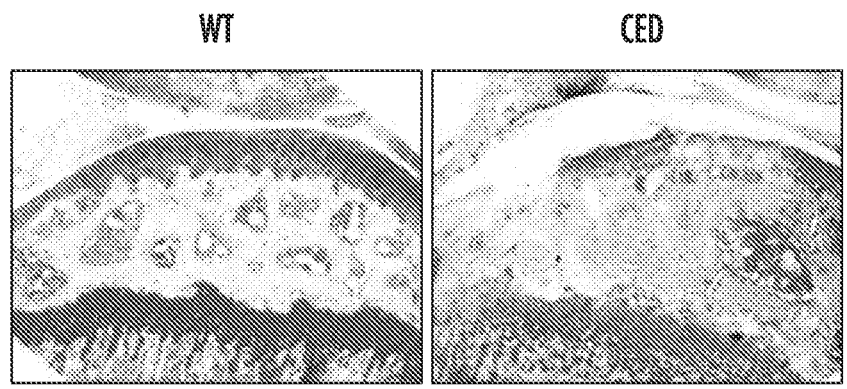
Figure 2C:
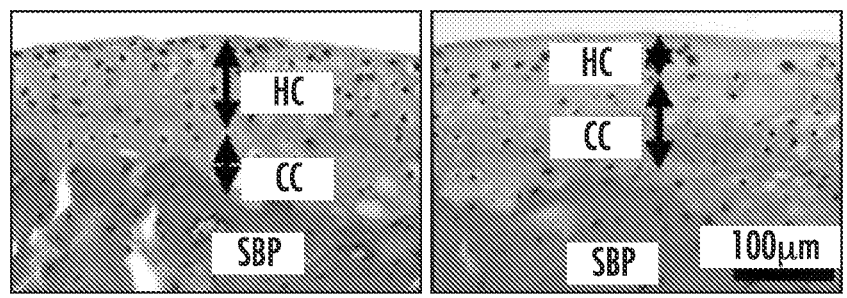

In Camurati-Engelmann disease (CED), TGF-β1 is activated upon secretion due to a point activating mutation in the TGFβ1 gene, and interestingly, people with CED are prone to develop osteoarthritis. To examine whether high concentrations of active TGF-β1 in the subchondral bone initiates osteoarthritis, we used a CED activation mutation mouse model in which TGF-β1 is activated upon secretion in the subchondral bone marrow by osteoblastic cells. Three-dimensional μCT images of cross sectional, coronal and sagittal views of tibial subchondral bone showed uneven distribution of bone mass in CED mice relative to their wild-type littermates, indicating disrupted bone formation (FIG. 2a). Similar to the ACLT mouse model, the tibial subchondral bone TV and Tb.Pf increased whereas thickness of the SBP decreased in CED mice relative to their wild-type littermates. Notably, significant proteoglycan loss was detected at the calcified cartilage zone adjacent to the subchondral plate (FIG. 2h (top)). The thickness of calcified cartilage layer significantly increased whereas the hyaline cartilage layer decreased with apparent hypocellularity (FIG. 2b (bottom)). The OARSI scores revealed significant degeneration of articular cartilage in CED mice relative to their age-matched littermates (FIG. 2c).

Figure 2D:
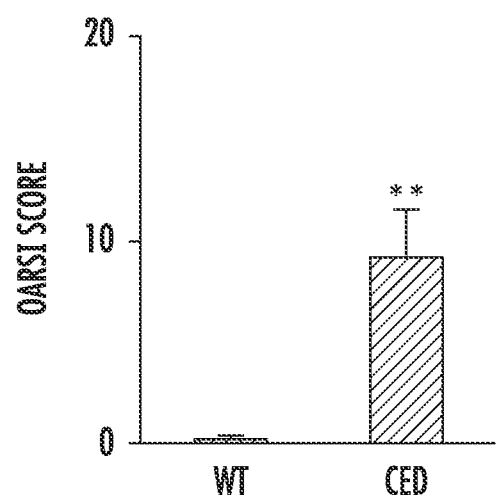
Figure 2G:
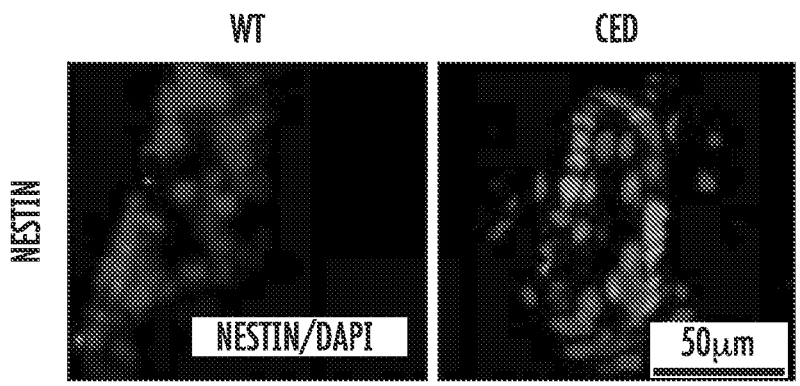
Figure 2H:
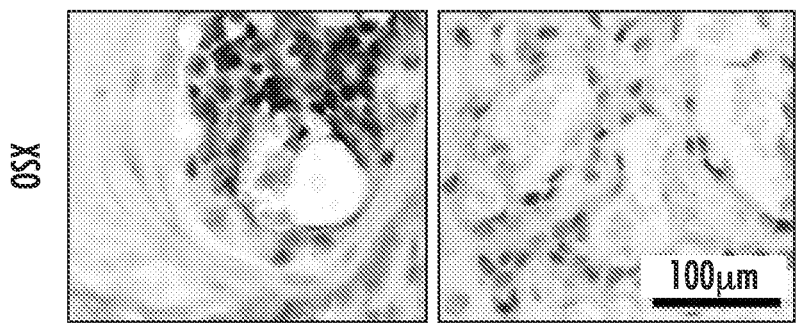
Figure 2I:
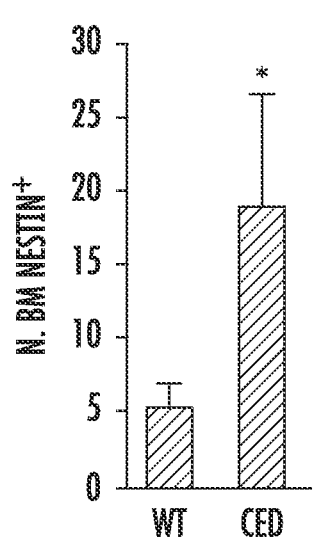
Figure 2I:
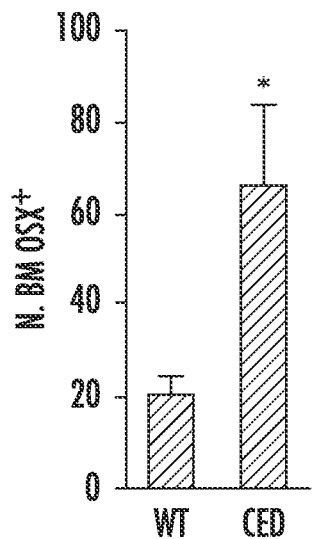
Figure 2I:
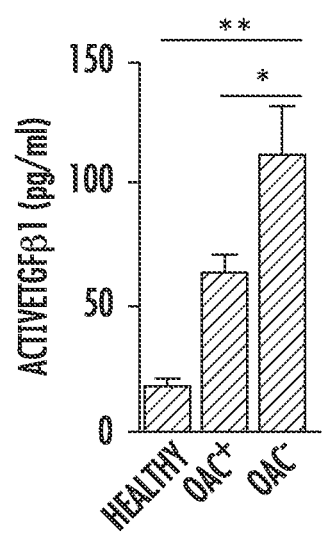

We also measured angiogenesis in these mice using microfil contrast-enhanced angiography since it is a pathological manifestation of osteoarthritis. The volume fraction and number of blood vessels in subchondral bone increased significantly in CED mice relative to their wild-type littermates (FIG. 2d). Consistently, the number of CD31+ endothelial progenitor cells also increased (FIG. 2e). Immunostaining for nestin, primarily expressed in adult bone marrow MSCs, revealed a significantly higher number of nestin+ cells in the subchondral bone marrow of CED mice compared to wild type controls (FIG. 2f). Once committed to the osteoblast lineage, MSCs express osterix, a marker of osteoprogenitors. The number of osterix+ osteoprogenitors also significantly increased in the subchondral bone marrow compared to wild type controls (FIG. 2f), indicating nestin+ MSCs undergo osteoblastic differentiation for de novo bone formation. In addition, we also measured active TGF-β1 in the subchondral bone of human knee joints at different stages of osteoarthritis. ELISA analysis showed that the concentrations of active TGF-β1 in the subchondral bone of human osteoarthritis knee joints were significantly higher than those of healthy controls (FIG. 2g). Collectively, development of the knee joint osteoarthritis phenotype CED mice was similar to that observed in the ACLT mouse model, revealing that high concentrations of active TGF-β1-induced abnormal subchondral bone formation may contribute to the degeneration of articular cartilage.

Example 3: Subchondral Bone TGF-β Inhibition Attenuates Cartilage Degeneration

Figure 3B:
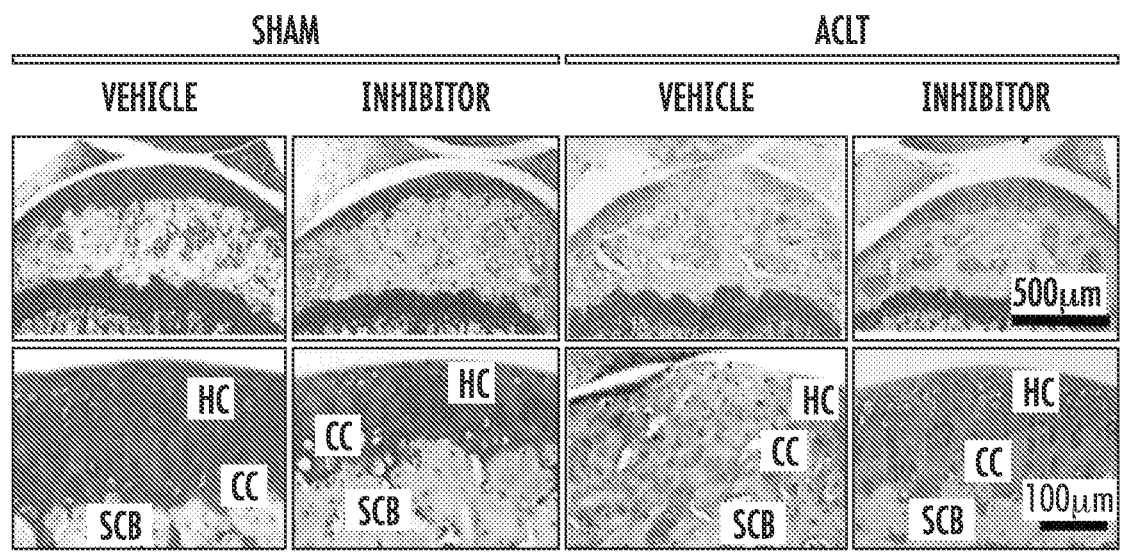
Figure 3C:
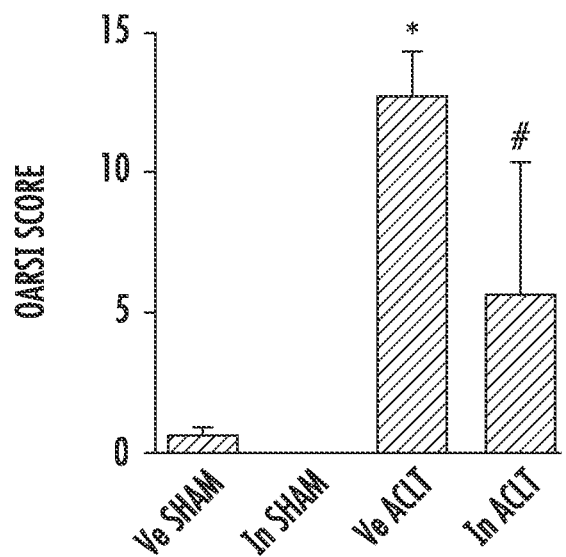
Figure 3D:
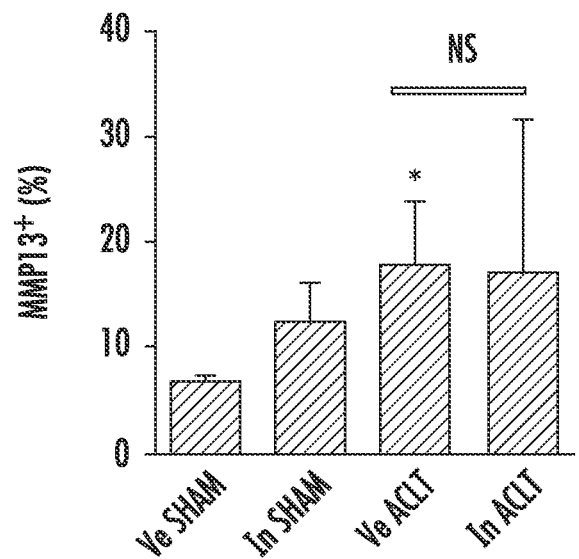
Figure 3E:
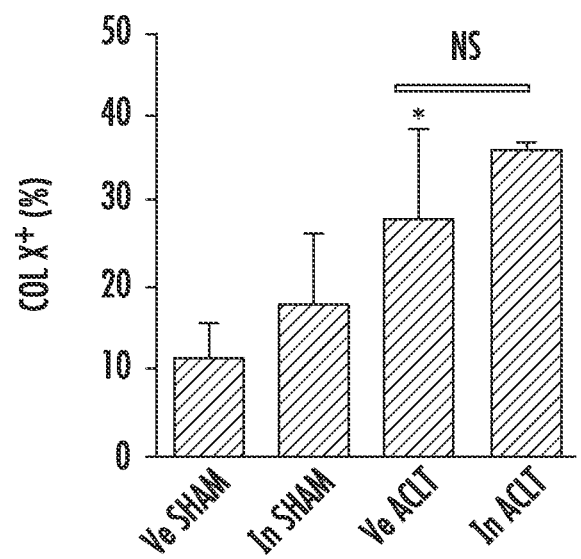
Figure 3F:
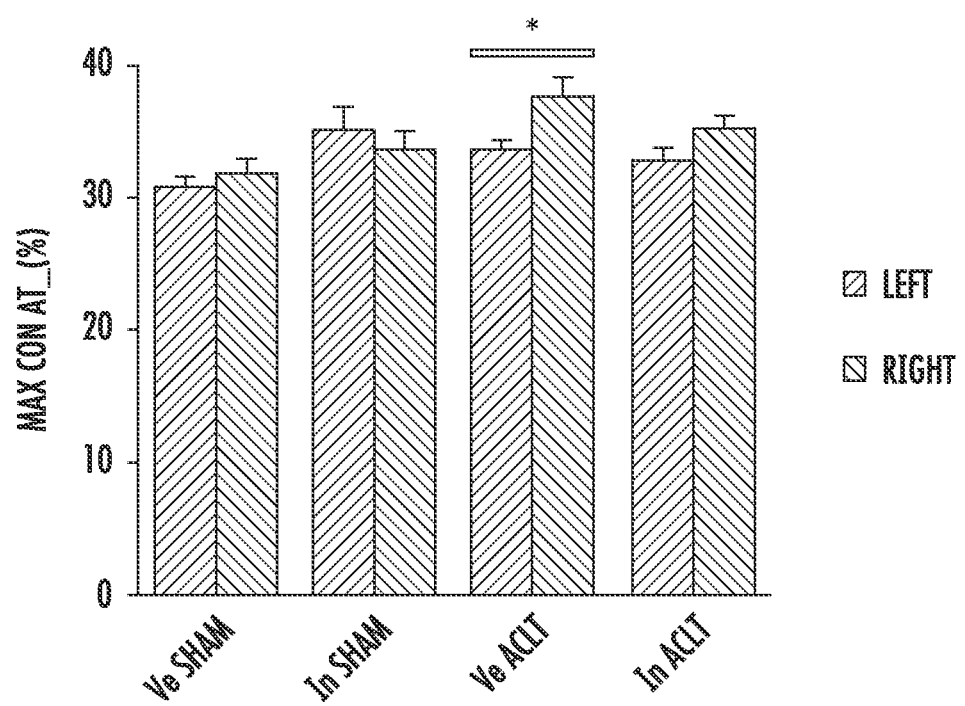
Figure 9A:
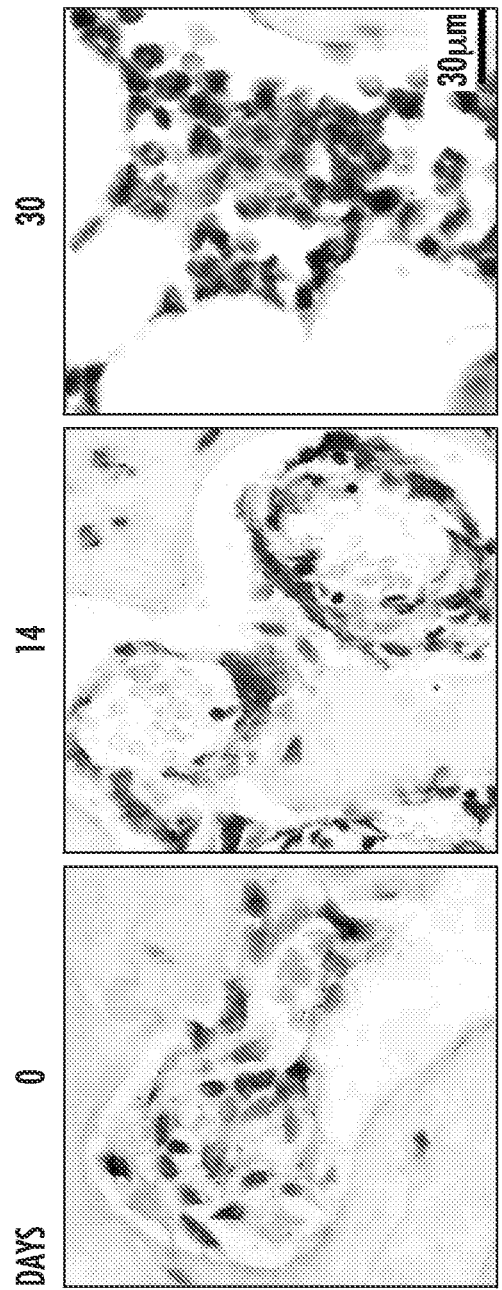
FIGS. 9A-9B: Distribution of osterix-positive cells in bone marrow of tibial subchondral bone in ACLT osteoarthritis mouse model.
Figure 9B:
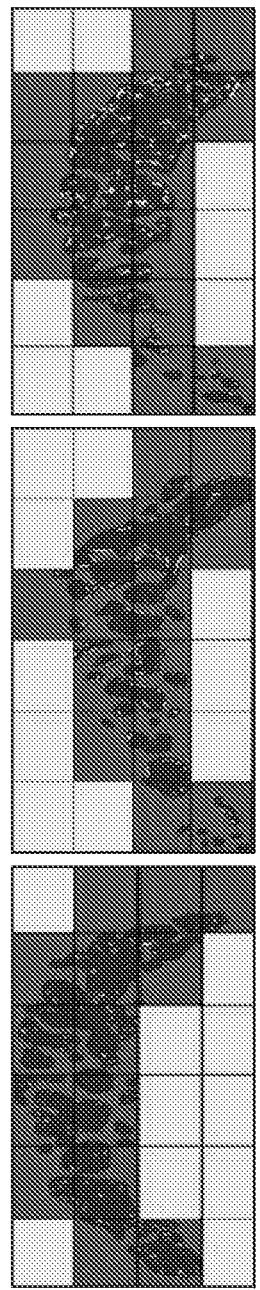
Figures 10A, 10B:
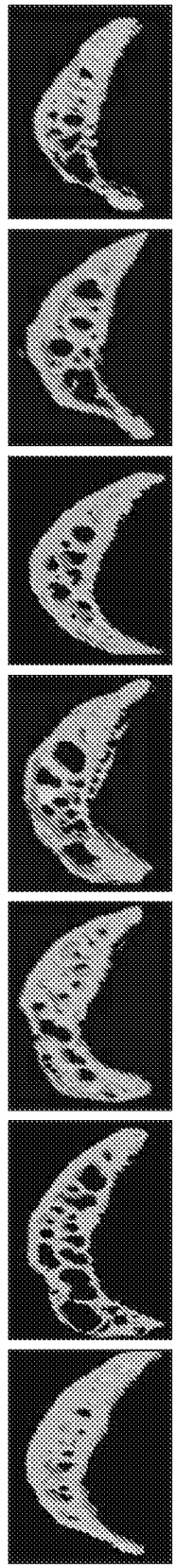
FIGS. 10A-10E: Type I TGFβ1 receptor (TβRI) inhibitor dose dependent effects on articular cartilage and subchondral bone.
Figure 10C:
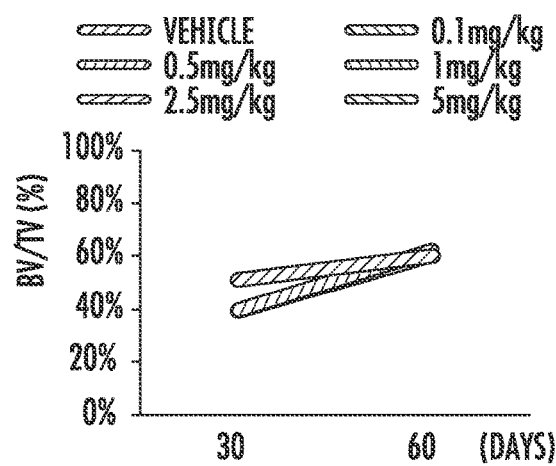
Figure 10D:
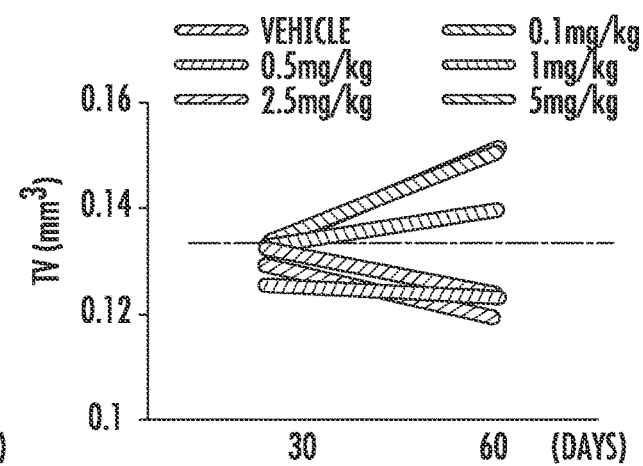
Figure 10E:
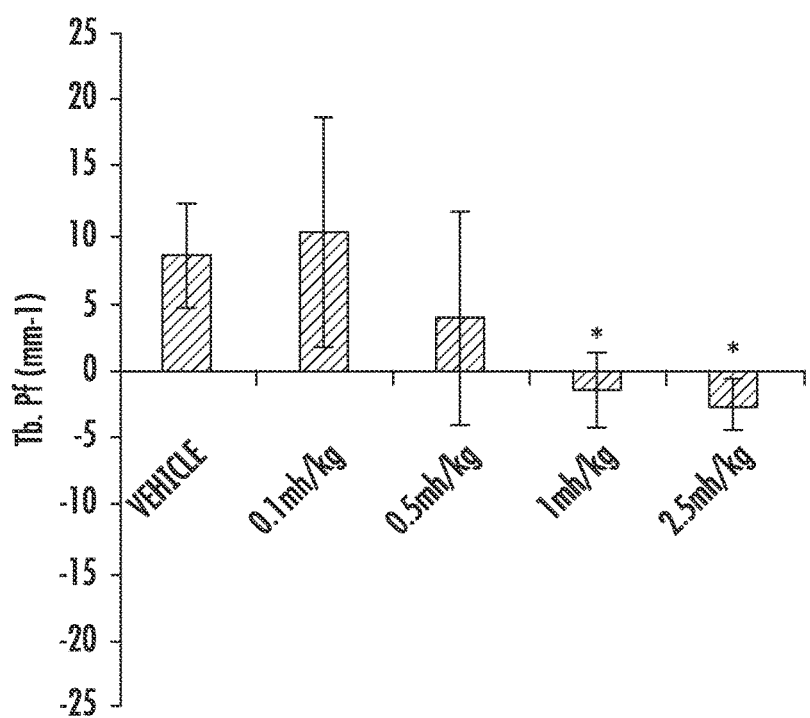

We next examined the effects of inhibition of TGF-β activity on ACLT joints. Injection of TβRI inhibitor (SB505124) has been shown to rescue uncoupled bone formation induced by high concentrations of active TGF-β1. We screened different doses of the TβRI inhibitor with ACLT mice to identify the optimal dose (FIG. 9). Low concentrations of TβRI inhibitor (0.1 or 0.5 mg kg$^{-1}$) had minimal effects on the subchondral bone, whereas higher concentrations, beginning at 1 mg kg$^{-1}$ improved subchondral bone structure (FIG. 3a). On the contrary, proteoglycan loss in articular cartilage was induced at higher concentrations (2.5 or 5 mg kg$^{-1}$) (FIG. 9a). Of note, proteoglycan loss induced by higher doses of inhibitor was primarily observed in the superficial to middle zones of articular cartilage (FIG. 9a). Improvement of trabeculae connectivity and micro-architecture with 1 mg kg$^{-1}$ of the TβRI inhibitor was demonstrated by normalization of subchondral bone TV (FIG. 3b), maintenance of the thickness of SBP (FIG. 3c) and volume decrease in Tb. Pf (FIG. 3d). Notably, proteoglycan loss and calcification of articular cartilage were attenuated in ACLT mice 2 months post-surgery, a time point often used for analysis of destabilized osteoarthritis mice models (FIG. 3e). The protective effect of the TβRI inhibitor on articular cartilage in TβRI inhibitor treated compared to vehicle treated ACLT mice was quantified using OARSI system (FIG. 3f). The inhibitor had no significant effects on the elevated concentrations of MMP13 or type X collagen chondrocytes as compared to vehicle treated ACLT group (FIG. 3g, h).

Similar results were observed in 9-month-old ACLT mice. Subchondral bone structure was improved and articular cartilage degeneration was attenuated in aged ACLT mice treated with 1 mg kg$^{-1}$ of WI inhibitor (FIG. 12). Moreover, gait analysis with Catwalk system revealed significant disparity between the percentages of maximum contact time (Maxcontactat %) of the two hind limbs two months post-surgery, which was rescued in the inhibitor-treated ACLT group (FIG. 3i). Taken together, the results indicate that TGF-β plays distinct roles in the subchondral bone and articular cartilage and inhibition of TGF-β activity in the subchondral bone may prevent degeneration of articular cartilage during osteoarthritis development.

Figure 4C:
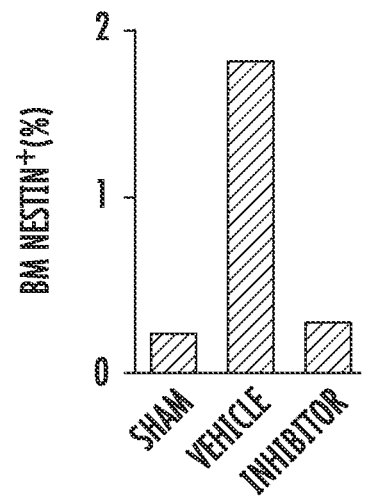
FIGS. 4A-4P. TβRI inhibitor reduced uncoupled bone formation and angiogenesis in ACLT mice. (a) Immunofluorescent or immunohistochemical analysis and quantification of (FIG. 4A(i), 4A(ii) and 4C nestin (red) and (FIGS. 4B(i), 4B(ii) and 4D osterix (brown) in tibial subchondral bone collected one month after sham operation treated with vehicle (Sham), ACLT operated treated with vehicle (Vehicle), or ACLT operated treated with TβRI inhibitor (Inhibitor). DAPI stains nuclei (blue) (top). Scale bars, 50 μm.
(FIG. 4E) Immunohistochemical analysis of osteocalcin (brown) and (FIG. 4F) trichrome staining in tibial subchondral bone sections. Scale bars, 50 μm. Open arrowheads indicating osteocalcin$^+$ cells and close arrowheads indicating osteoid.
(FIG. 4G) Flow cytometry analysis of nestin and osterix in bone marrow from mouse subchondral bone. Calcein (green) and xylenol orange (orange) fluorescent double labeling. Scale bar, 100 μm.
(FIG. 4H) Western blot analysis of pSmad1/5/8, Smad1/5, pSmad2 and Smad2 of in cultured MSCs treated with increasing doses of recombinant hTGF-β1, Immunohistochemical analysis and quantification of (FIGS. 4I(i) and 4I(ii) pSmad2/3, (FIGS. 4J(i) and 4J(ii) pSmad1, (FIGS. 4K(i) and 4K(ii) ALK5 and (FIGS. 4L(i) and 4L(ii) ALK1 (all stained brown) in subchondral bone of the mice 2 weeks post-surgery. Scale bar, 50 μm.
(FIGS. 4M(i) and 4M(ii)) Immunohistochemical analysis and quantification of CD31 (brown) in subchondral bone. Scale bar, 50 μm.
(FIG. 4N(i)) CT-based micro-angiography of the tibia subchondral bone and quantification of subchondral bone (FIG. 4N(ii) vessel volume (VV) and (FIG. 4N(iii) vessel number (VN), Scale bar, 500 μm.
(FIG. 4O) Perfusion rate obtained via T2 weighted MM scanning with contrast.
Figure 4D:
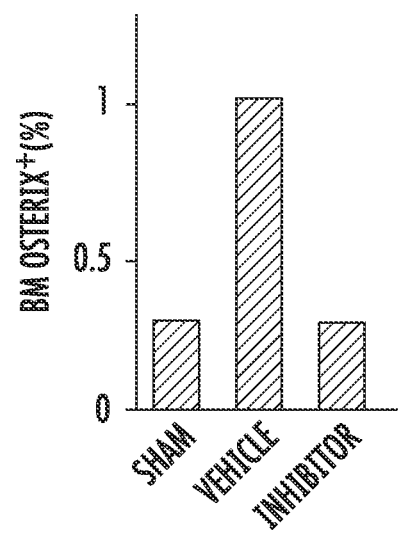

Example 4: Increase of MSC Clusters Leads to Osteoid Islets in the Subchondral Bone Marrow To examine the cellular mechanism, we analyzed the effect of TβRI inhibitor on MSCs in the subchondral bone. We found by immunostaining that nesting$^+$ MSCs in subchondral bone marrow were dramatically increased in numbers by 30 days post-surgery in ACLT mice as compared to that of sham controls (FIG. 4a). This effect was prevented by the TβRI inhibitor (FIG. 4a). Similarly, osterix osteoprogenitors were largely located on the bone surface in sham controls (FIG. 4a) and the significantly increased number of osteoprogenitor clusters detected in the bone marrow in the vehicle-treated ACLT group was attenuated with TβRI inhibitor treatment (FIG. 4a). These results were confirmed in flow cytometry analysis of nestin$^+$ MSCs and osterix$^+$ osteoprogenitors from subchondral bone (FIG. 4c). Osteocalcin$^+$ osteoblasts and osteoids as islets were observed in the marrow of the ACLT subchondral bone. Injection of TβRI inhibitor reduced the abnormal localization of the osteoid islets, as the osteocalcin$^+$ osteoblasts and osteoid were largely found on the bone surface, similar to their location in sham controls (FIG. 4b). Formation of osteoid islets was reduced by the TβRI inhibitor compared to the vehicle-treated group in fluorescent double labeling experiment (FIG. 4d).

Figure 4E:
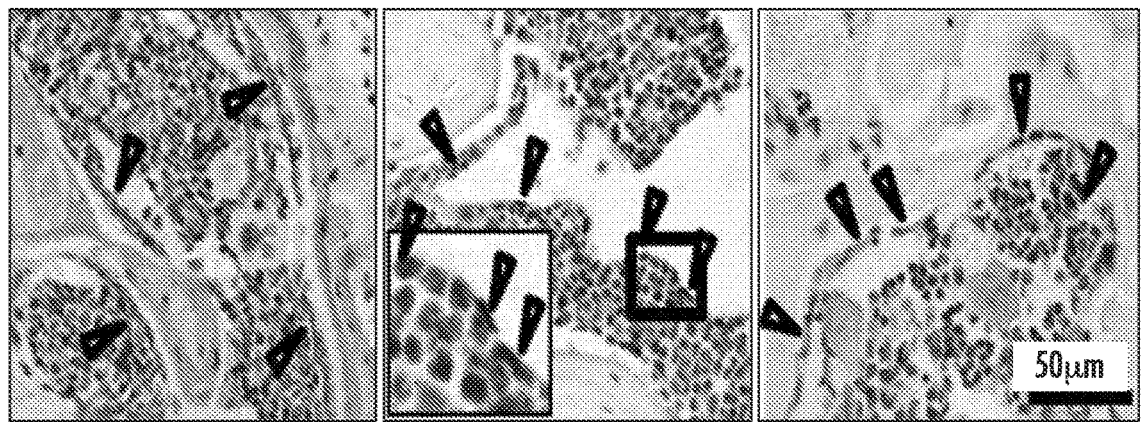
Figure 4F:
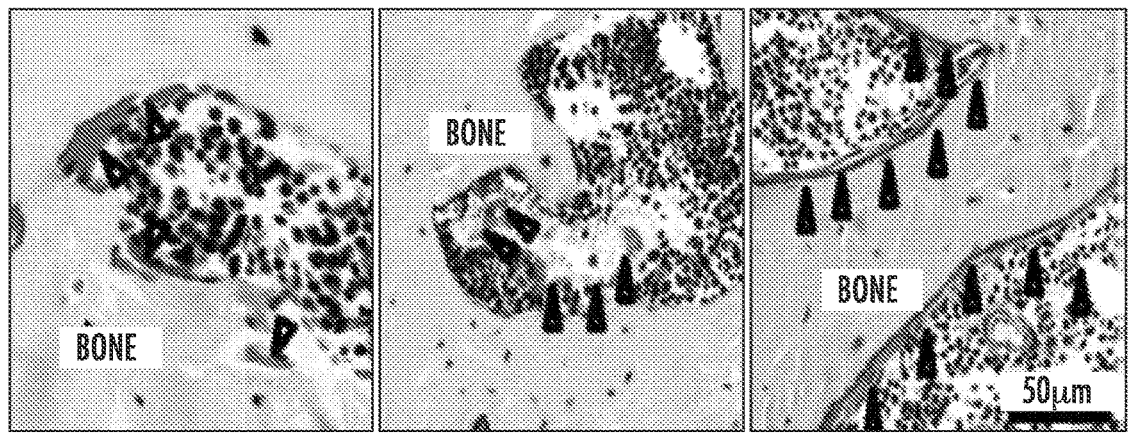
Figure 4G:
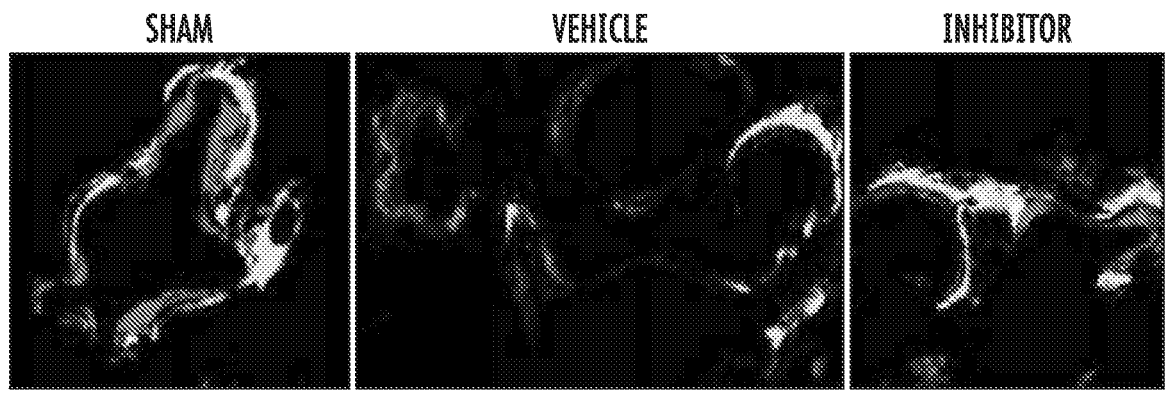
Figure 4H:
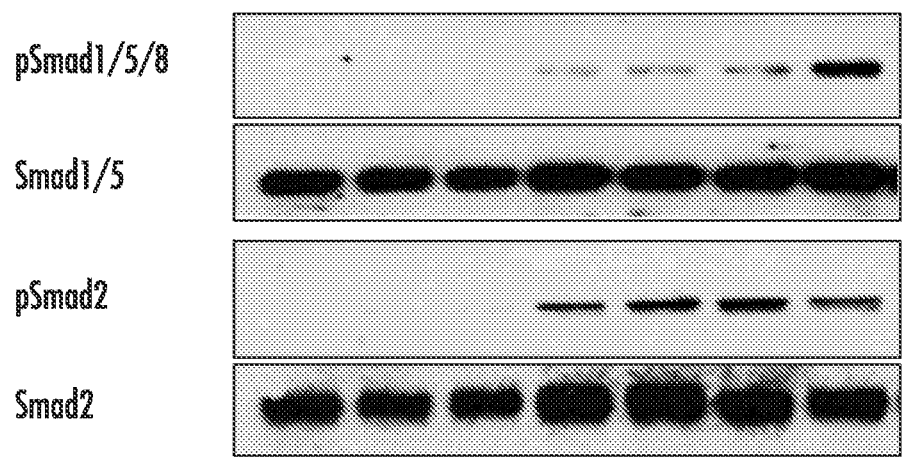
Figure 4I:
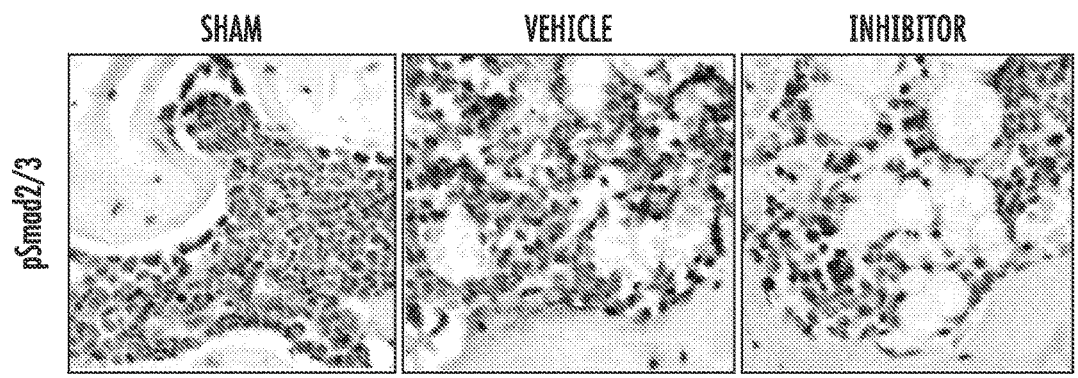
Figure 4J:
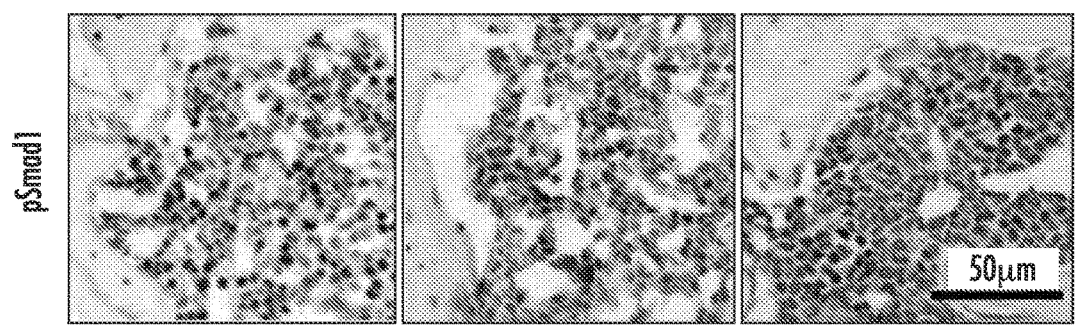
Figure 4K:
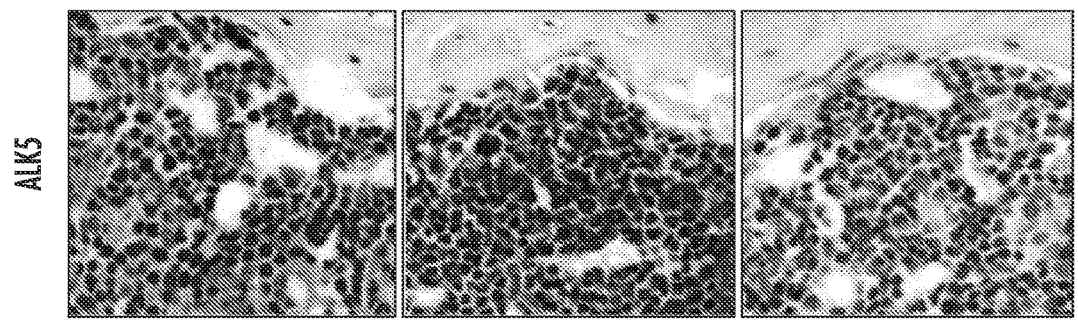
Figure 4L:
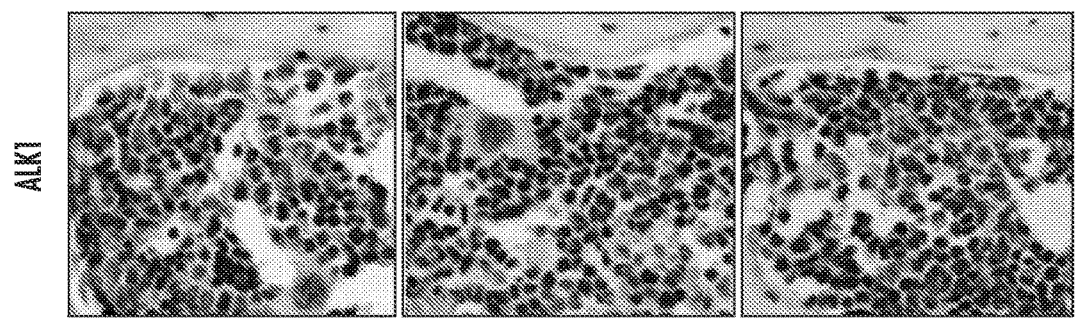
Figure 4O:
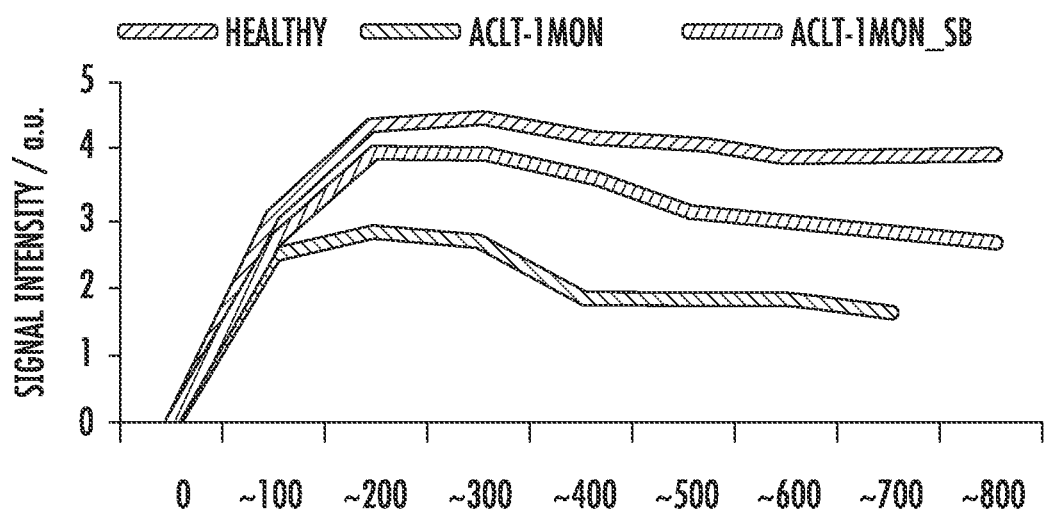
Figure 4P:
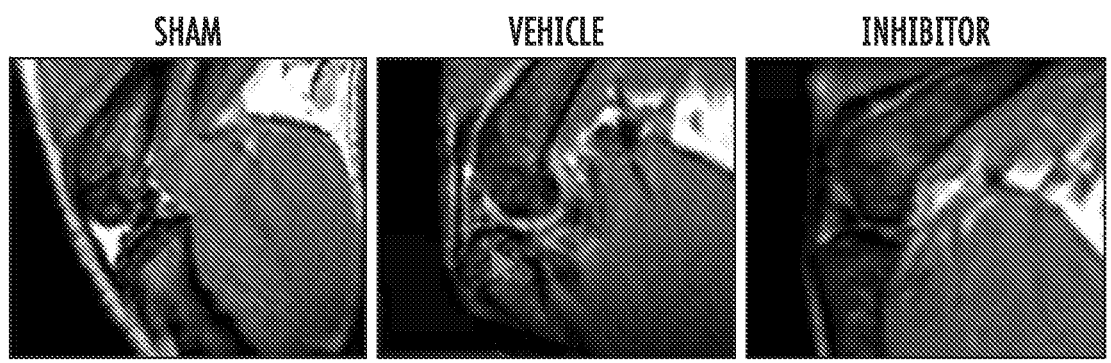

Phosphorylation of SmadI can be activated by TGF-β1 in endothelial progenitor cells. We examined whether TGF-β1 activates phosphorylation of Smad1 in MSCs. We found that TGF-β1 stimulated phosphorylation of both Smad2/3 and Smad1/5/8 at low concentrations, but a maximal increase of phosphorylated Smad1/5/8 was achieved at a higher dose of TGF-β1 (5 ng ml$^{-1}$) (FIG. 4e). Immunostaining of the subchondral bone showed that the number of pSmadI$^+$ cells remained relatively stable in ACLT mice treated with TβRI inhibitor relative to sham controls. (FIG. 4f). In contrast, pSmad2/3$^+$ cells were greatly increased in ACLT mice and the increase was prevented by TβRI inhibitor treatment (FIG. 4f), suggesting that phosphorylation of Smad2/3 is the primary downstream signal of TGF-β in the subchondral bone MSCs. Consistently, the expression level of ALK1 remained unchanged in ACLT mice treated with vehicle or inhibitor relative to sham operated control mice whereas the expression of ALK5 was significantly increased in ACLT mice relative to control mice and the increase was inhibited with injection of TβRI inhibitor (FIG. 4f). CD31$^+$ endothelial progenitors were significantly increased in the subchondral bone of ACLT mice relative to sham controls, which was reduced by injection of TβRI inhibitor. (FIG. 4g). Microfil contrast-enhanced angiography of subchondral bone confirmed that the inhibitor decreased angiogenesis (FIG. 4h). The contrast signal was significantly increased in vehicle treated mice at 1 month post ACLT in MRI perfusion analysis and the increase was prevented in the inhibitor treated group, indicating reduced new vessel formation (FIG. 4i). The bone marrow lesion in tibial subchondral bone detected by micro-MRI was also obviously smaller in size in the ACLT-inhibitor treated mice as compared to that of ACLT-vehicle treated mice (FIG. 4j), suggesting the association of bone marrow lesions with osteoid islets. These results indicate that high concentrations of active TGF-β increased the number of nestin$^+$ MSCs, leading to subchondral bone marrow osteoid islets and angiogenesis, representing pathological changes of subchondral bone post ACLT.

Example 5: Neutralizing Subchondral TGF-β Reduces Osteoarthritic Severity

Figure 5C:
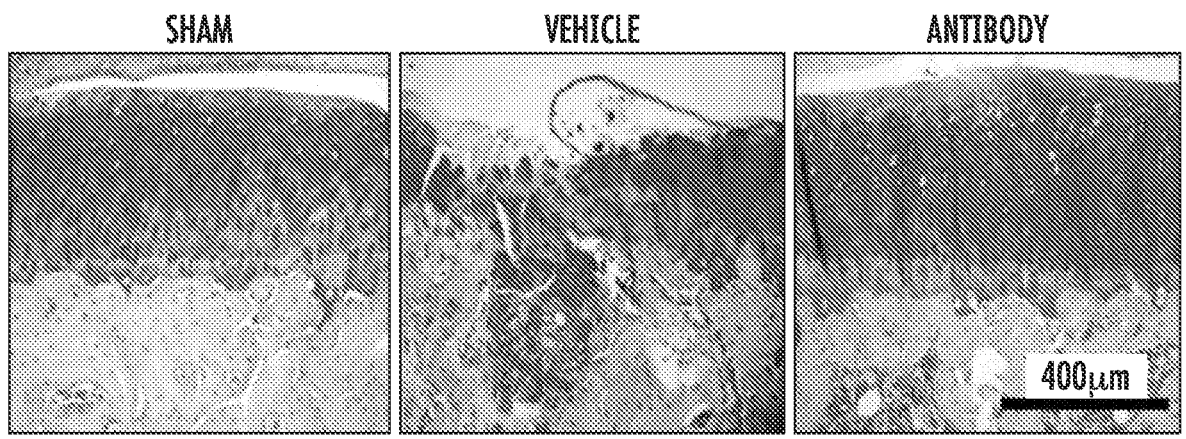
Figure 5D:
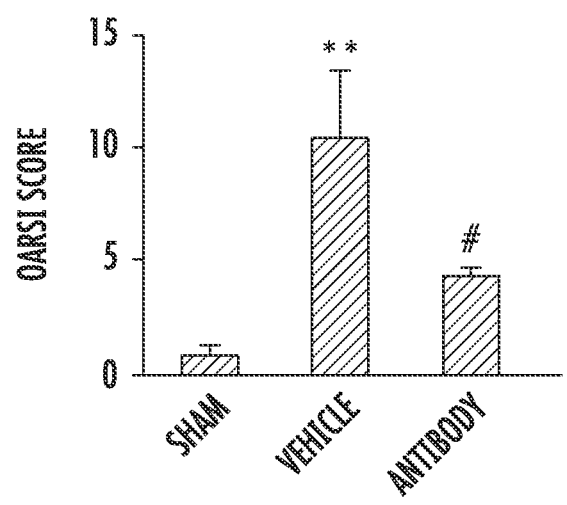

To validate the role of TGF-β in the subchondral bone at the onset of osteoarthritis, we implanted TGF-β antibody (1D11) in alginate beads directly in the tibial subchondral bone of rat ACLT joints. The knee joints were harvested 3 months post-surgery. Similar to systemic use of TβRI inhibitor, the micro-architecture of the bone was improved with local application of the antibody as compared to that of vehicle-treated ACLT rats (FIG. 5a-d). The number of osterix$^+$ progenitor clusters in bone marrow cavity of rat ACLT joints was significantly less in antibody-treated rats compared to that of the vehicle-treated rats (FIG. 5e). Notably, degeneration of articular cartilage was attenuated as reflected in OARSI scores by administration of the antibody in the subchondral bone (FIG. 5f (top), g). Moreover, the percentages of MMP13$^+$ and type X collagen$^+$ chondrocytes were significantly reduced, indicating protection from degeneration of articular cartilage (FIG. 5f), In contrast, MMP13 and ColX expression were not reduced significantly with systemic injection of TβRI inhibitor (FIG. 3g, h) since TGF-β is essential for homeostasis of articular cartilage. Therefore, specific administration of TGF-β antibody in the subchondral bone reduced aberrant bone formation, but did not inhibit TGF-β signaling in articular cartilage. The protective effect on articular cartilage in our rat osteoarthritis model was primarily through improvement of subchondral bone by site-specific administration of TGF-β antibody. The results further validate that the role of TGF-β in the subchondral bone is distinct horn its role in articular cartilage; high concentrations of active TGF-β1 in the subchondral bone induced abnormal bone formation leading to development of osteoarthritis.

Example 6: Knockout of TGFBR2 in MSCs Reduces Osteoarthritic Severity

Figure 6C:
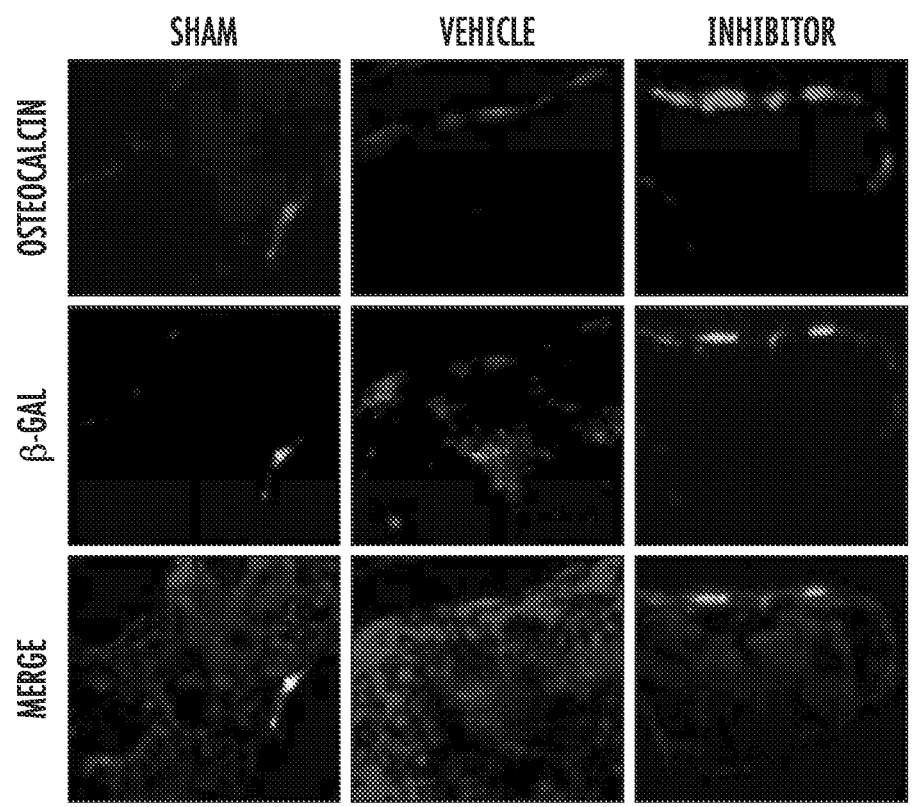
Figure 6D:
Figure 6E:
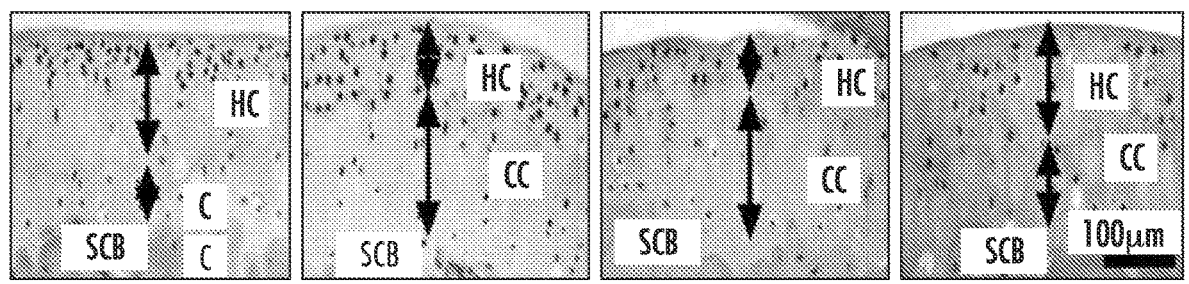
Figure 6F:
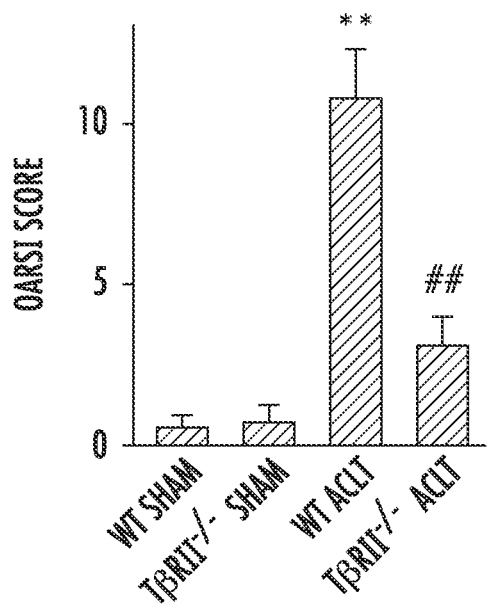
Figure 6G:
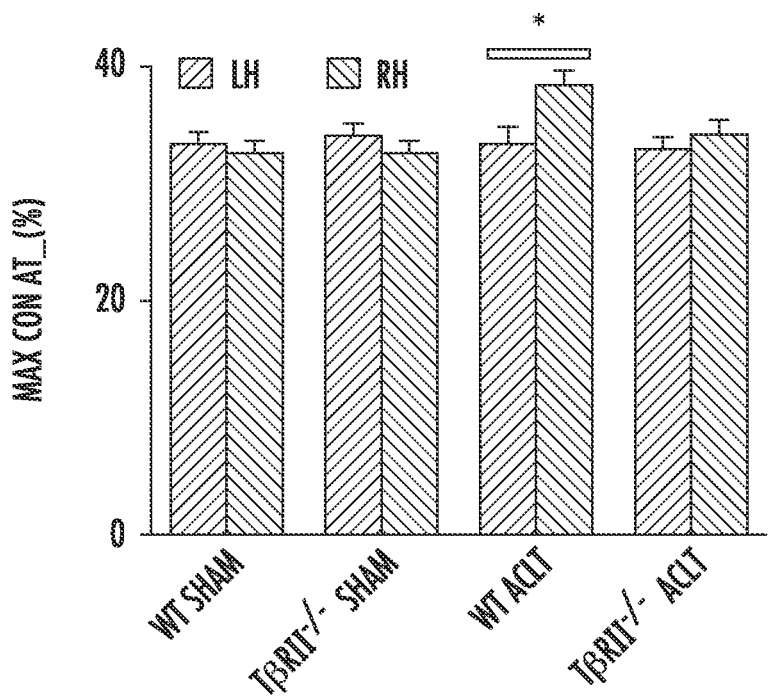
Figure 7A:
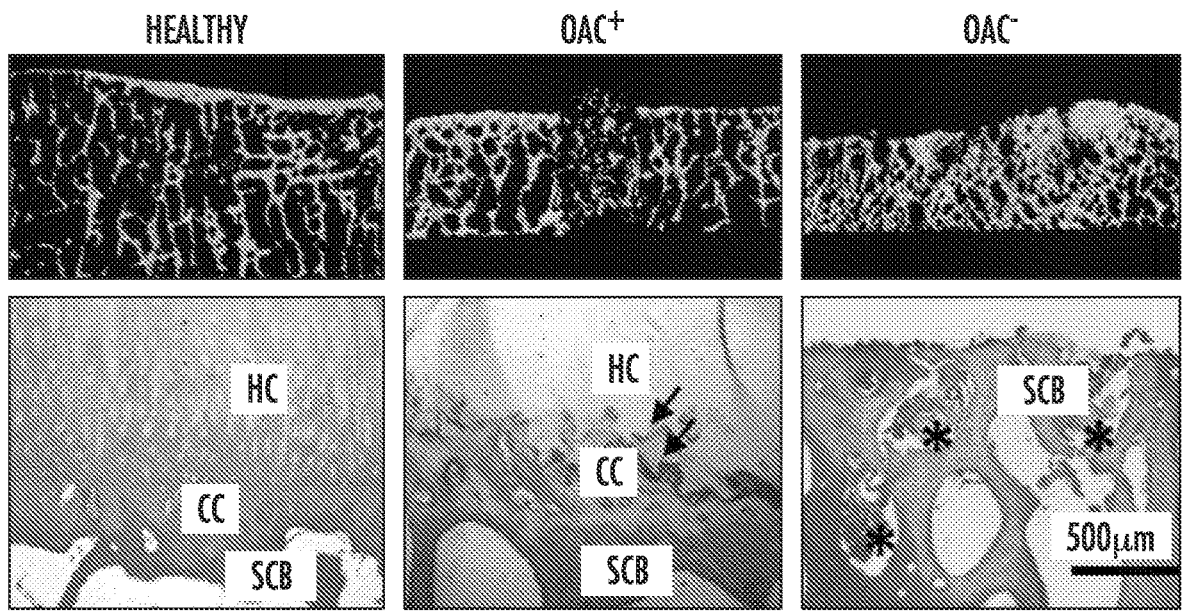
FIGS. 7A-7F. Characterization of human knee joints with OA.
Figure 7B:
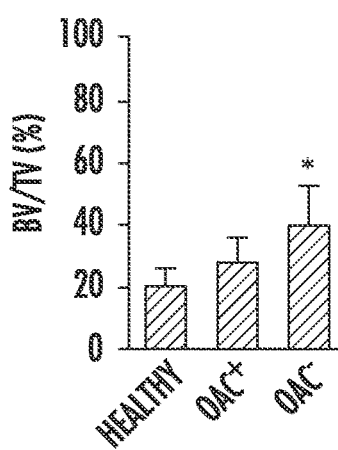
Figure 7C:
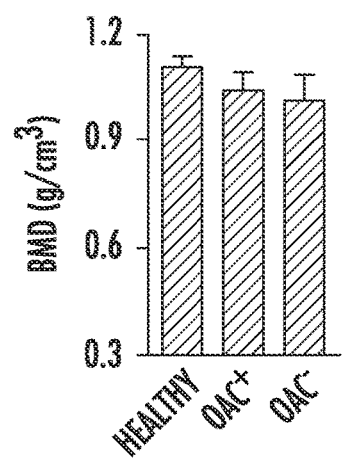
Figure 7D:
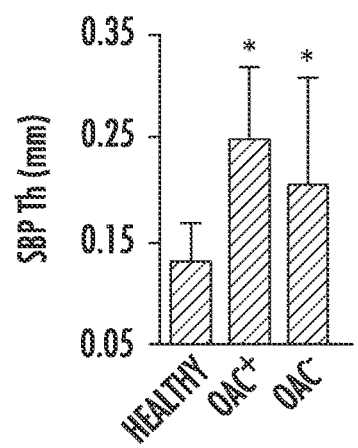
Figure 7E:
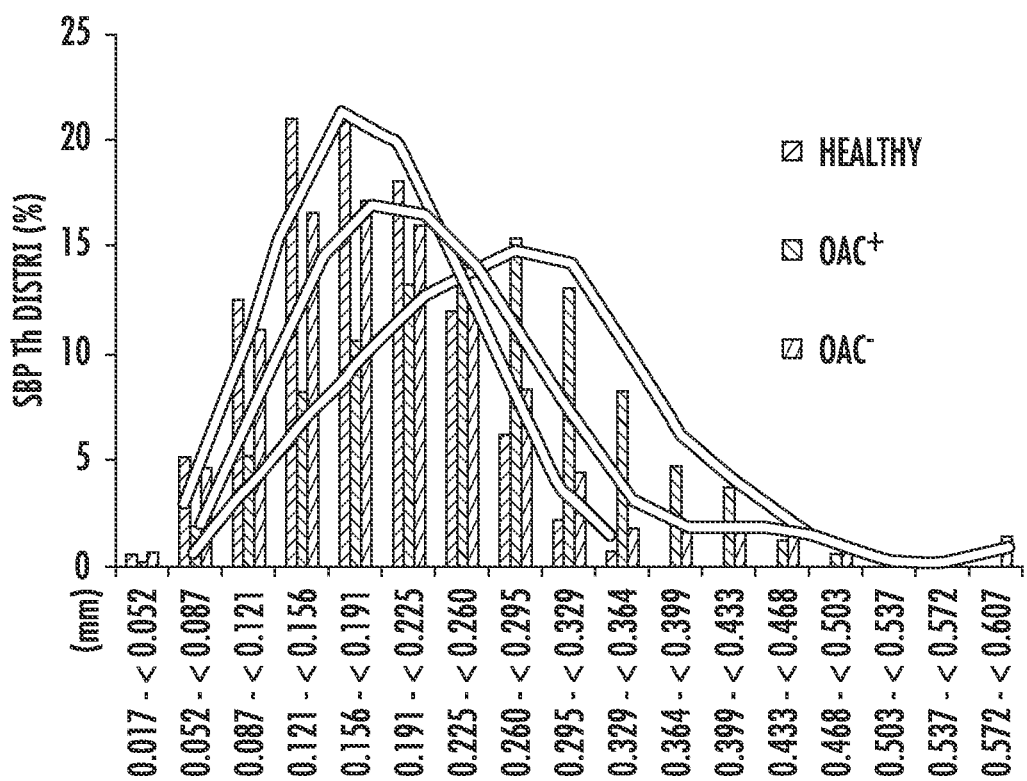
Figure 7F:
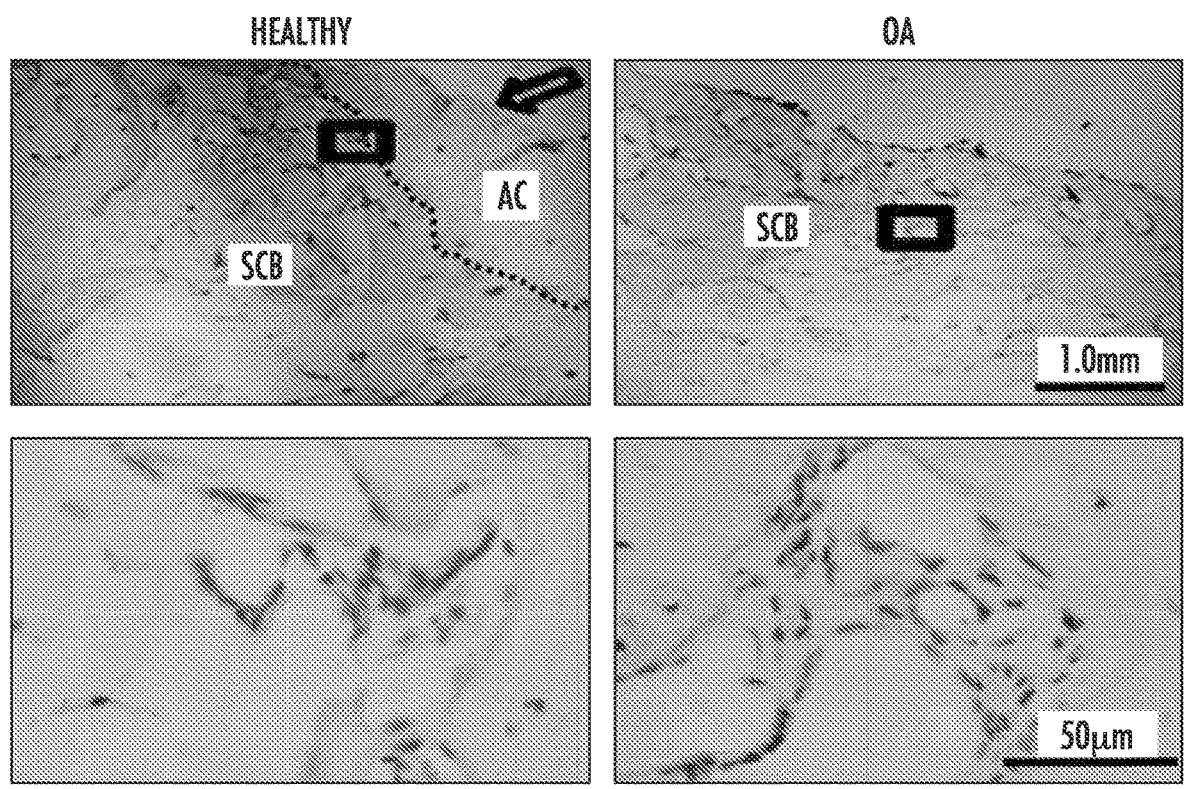
Figure 8A:
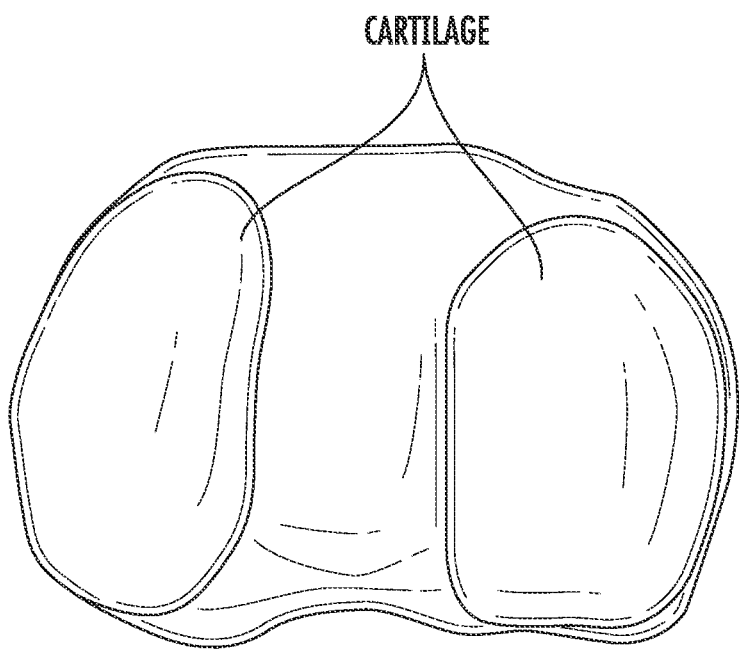
Figure 8B:
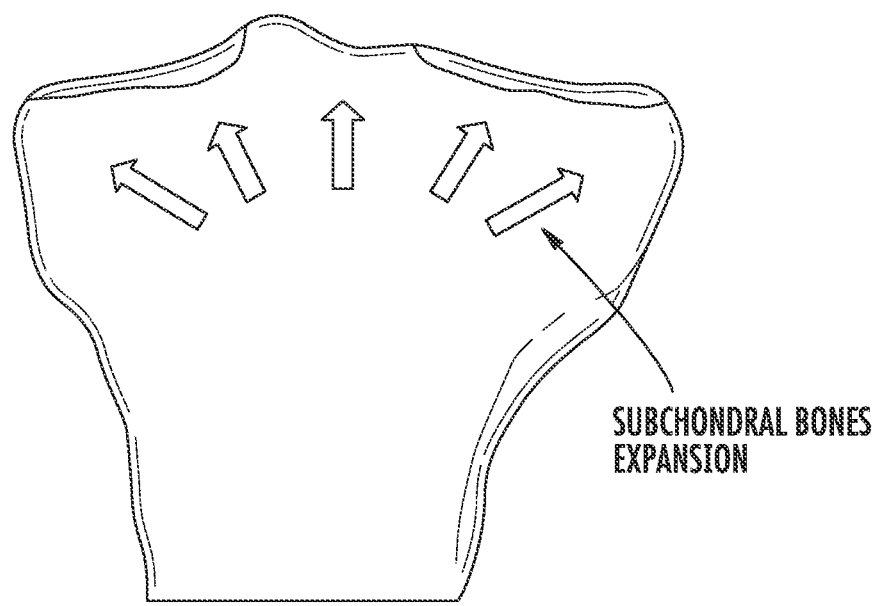
Figure 8F:
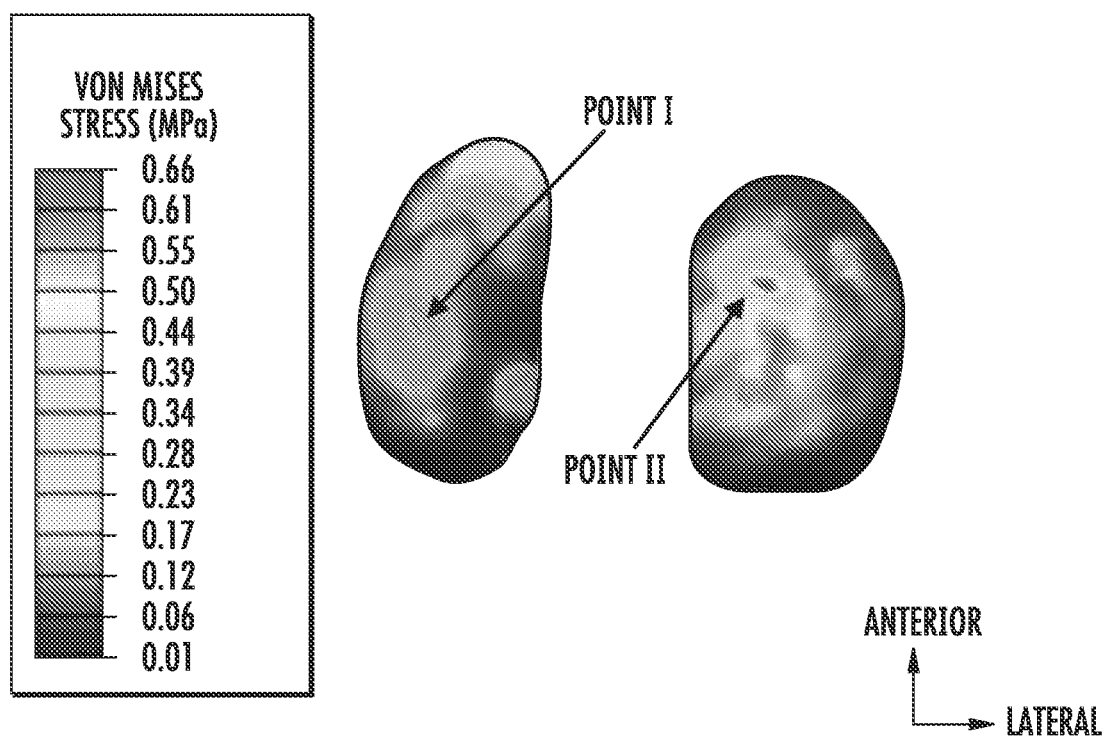
Figure 8G:
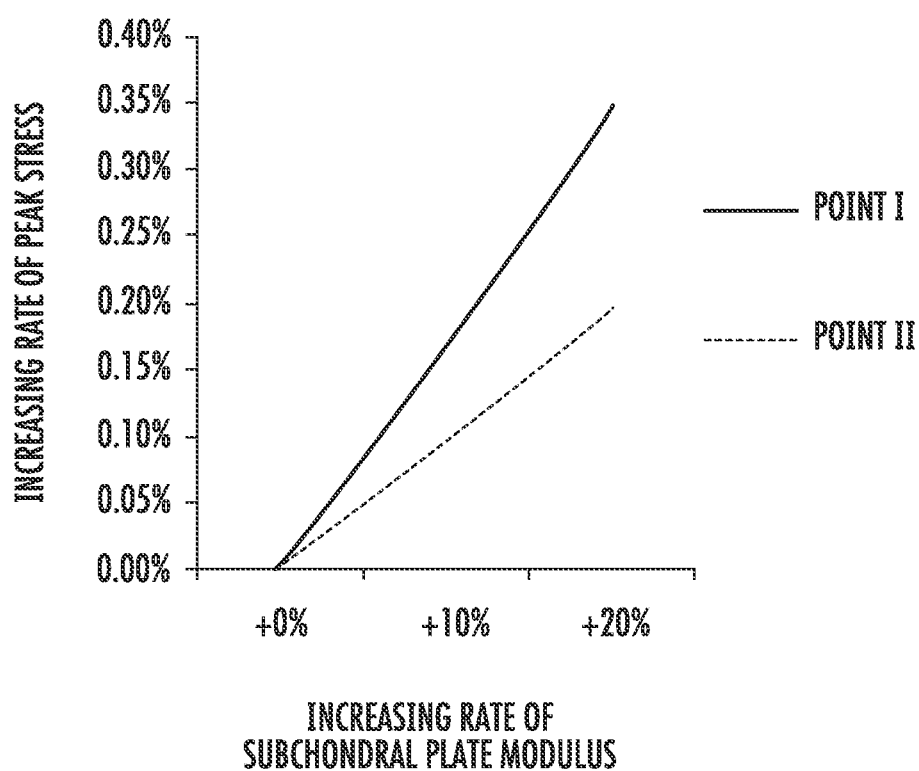

TGF-β binds to a complex of TGF-β type II receptor (TβRII) and TβRI to induce phosphorylation of downstream Smad2/3. Deletion of the TGFBR2 ensures blocking of the TGF-β signaling cascade. We induced knockout of TGFBR2 in nestin$^+$ MSCs of ACLT mice to confirm the critical role of TGF-β signaling in MSCs at the onset of osteoarthritis. Nestin-Cre™ER::TβRII$^{fl/fl}$ mice were injected with tamoxifen to delete TGFBR2 (TβRII$^{-/-}$) in the nestin MSCs unresponsive to TGF-β while the TGF-β signaling pathway in other cell types, including chondrocytes remained intact (FIG. 13). Similar to those of TβRI inhibitor treatment, the micro-architecture and Tb. Pf were significantly improved in the ACLT TβRII$^{-/-}$ mice at 2 months post-surgery relative to the ACLT wild type littermates (FIG. 6a). Osterix$^+$ osteoprogenitors in the subchondral bone remained primarily on the bone surface similar to ACLT wild type littermates (FIG. 6b). Moreover, co-staining of β-gal and osteocalcin in the subchondral bone of Nestin-Cre™ER::Rosa26 LacZ$^{fl/fl}$ mice revealed that the β-gal$^+$ MSC lineage cells were detected in the bone marrow in the vehicle-treated ACLT mice whereas β-gal$^+$ cells were primarily distributed on bone surface and were osteocalcin$^+$ in sham controls and TβRI inhibitor treated ACLT mice (FIG. 6c). The proteoglycan loss in articular cartilage was reduced in the ACLT TβRII$^{-/-}$ mice (FIG. 6d (top)). Calcification of articular cartilage was also attenuated and the thickness of calcified cartilage remained unchanged relative to ACLT wild type mice (FIG. 6d (bottom)). Immunostaining demonstrated that the concentrations of MMP13 and type X collagen expression were significantly inhibited in ACLT TβRII$^{-/-}$ mice relative to their ACLT wild-type littermates, indicating inhibition of articular cartilage degeneration (FIG. 6g). The protective effects on articular cartilage in ACLT TβRII$^{-/-}$ mice were reflected in OARSI scores (FIG. 6e). The disparity between the percentage of maximum contact time (Maxcontactat %) of the two hind limbs in wild type ACLT mice did not occur in their ACLT TβRII$^{-/-}$ littermates as revealed by gait analysis (FIG. 6f). Thus, this data further demonstrates that high concentrations of TGF-β initiate pathological changes in subchondral bone MSCs, contributing to the onset of osteoarthritis.

Example 7: Osteoid Islet in the Subchondral Bone Marrow can be Visualized by MRI T1-Weighted Images as Bone Marrow Lesions is a Biomarker of Joint Degeneration Joint pain and subchondral bone marrow lesions or edema are the early symptom of joint degeneration. Currently, nothing is known about the changes in subchondral bone in relation with pain and progression of articular cartilage degeneration, and there is no effective disease modifying treatment to prevent joint degeneration.

Increasing evidence suggests that the subchondral bone and articular cartilage acts as a functional unit in the joint. Changes at the osteochondral junction and in the subchondral bone are associated with early signs of joint degeneration such as bone marrow lesions or edema visualized under MRI and increased thickness of the subchondral plate and the calcified cartilage zone. However, it is unclear the pathological formation of subchondral bone marrow lesions. We have shown that TGFβ1 is activated during osteoclastic bone resorption and induces the migration of bone marrow mesenchymal stem cells (MSC) to resorption pits for the new bone formation, acting as a coupling factor. Transgenic expression of active TGFβ1 in osteoblastic cells leads to uncoupled bone remodeling with abnormal bone formation. More importantly, we have shown that high levels of active TGFβ1 in the subchondral bone initiate oetoid islets in the subchondral bone marrow causing calcification of articular cartilage in different OA animal models. Our data reveal that formation of osteoid islets is associated with subchondral bone marrow lesions, which is known to lead to articular cartilage loss and pain during joint degeneration. Therefore, formation of osteoid islets in the subchondral bone marrow is the onset of degeneration articular cartilage.

Figure 15A:
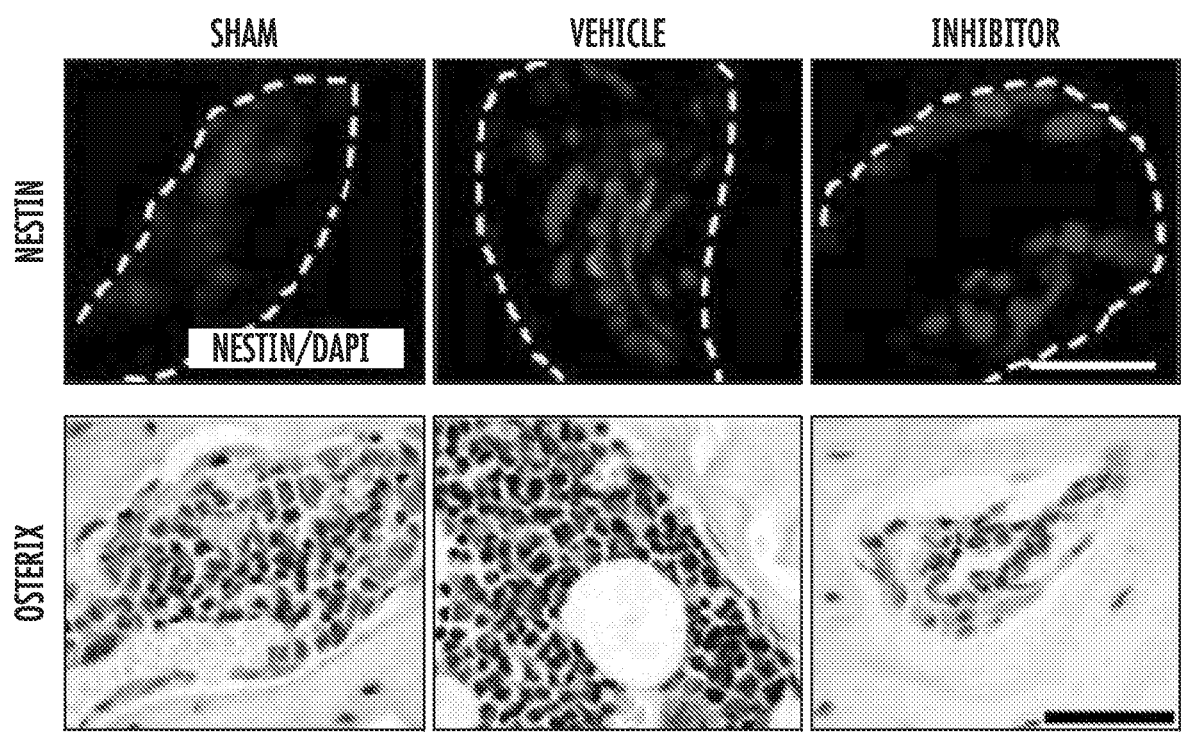
Figure 15B:
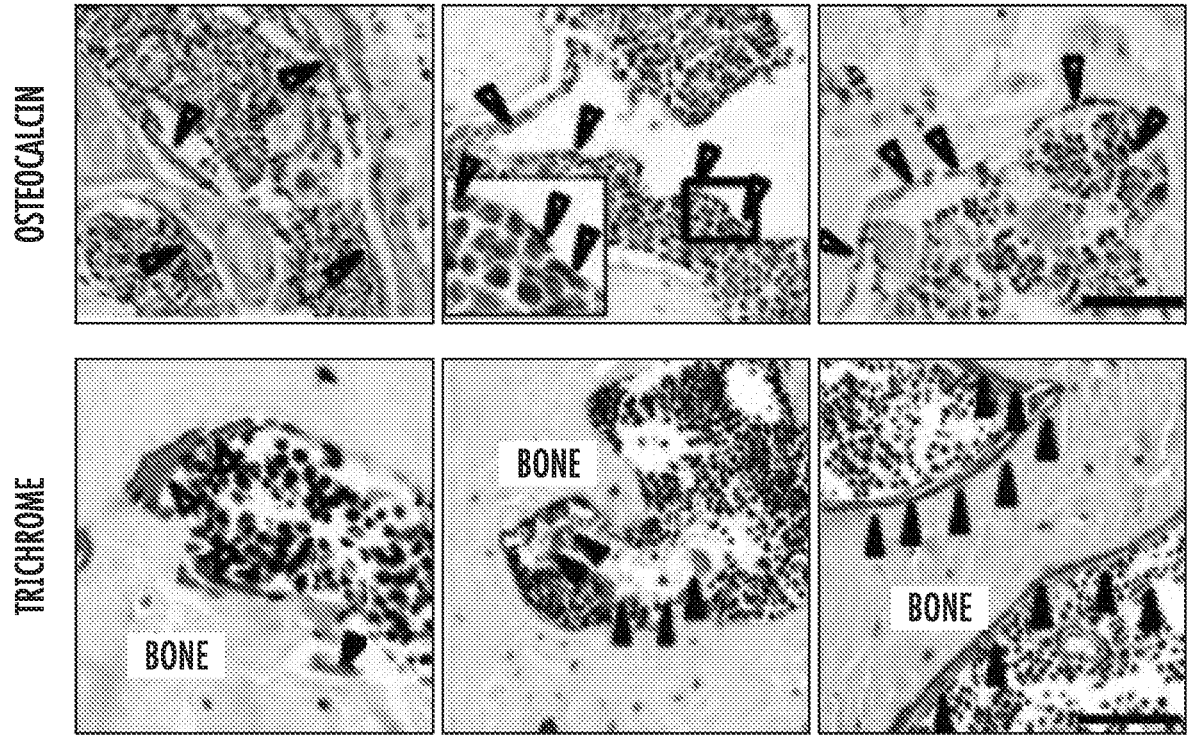
Figure 15C:
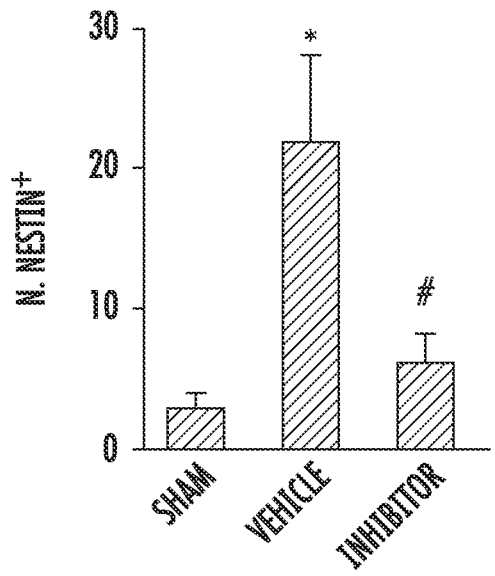
Figure 15C:
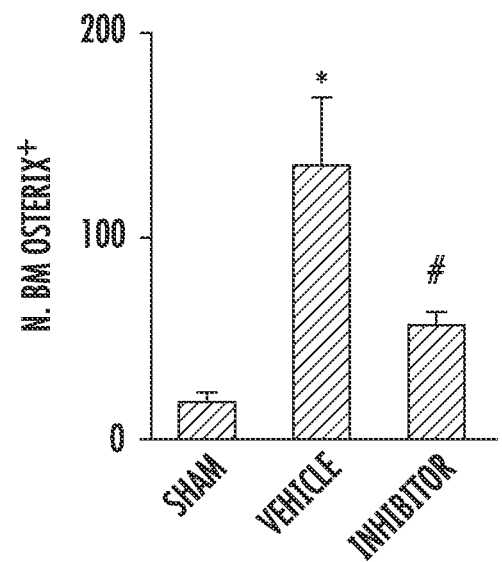
Figure 15C:
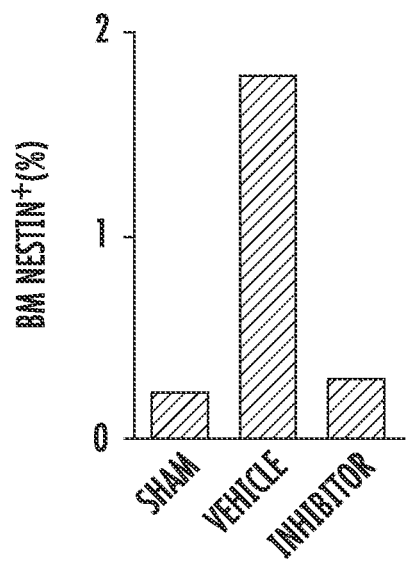
Figure 15C:
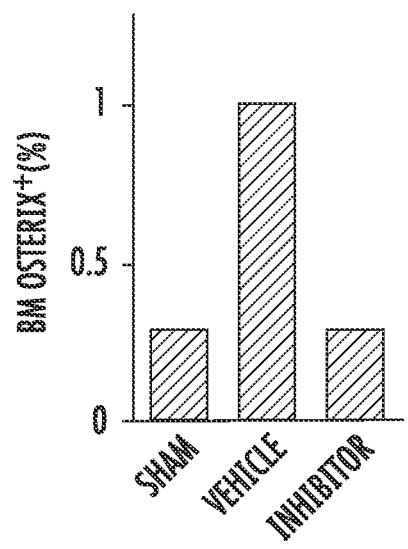
Figure 15D:
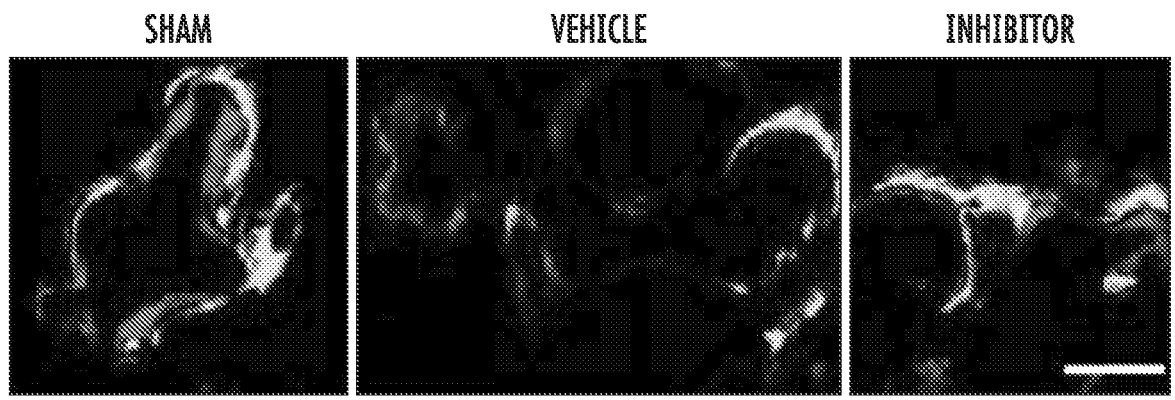

Specifically, we found by immunostaining that nestin$^+$ MSCs in subchondral bone marrow were dramatically increased in numbers by 30 days post-surgery in ACLT mice as compared to that of sham controls (FIG. 15a). This effect was prevented by the TβRI inhibitor (FIG. 15a). Similarly, osterix$^+$ osteoprogenitors were largely located on the bone surface in sham controls and the significantly increased number of osteoprogenitor clusters detected in the bone marrow in the vehicle-treated ACLT group was attenuated with TβRI inhibitor treatment (FIG. 15a). These results were confirmed in flow cytometry analysis of nestin$^+$ MSCs and osterix$^+$ osteoprogenitors from subchondral bone (FIG. 15c). Osteocalcin$^+$ osteoblasts and osteoids were observed in the subchondral bone marrow as bone marrow lesions (FIG. 15h), Injection of TβRI inhibitor reduced the abnormal localization, as the osteocalcin$^+$ osteoblasts and osteoid were largely found on the bone surface, similar to their location in sham controls (FIG. 15b). These osteoid islets in the subchondral bone marrow resulted uncoupled bone formation which was rescued by the TβRI inhibitor compared to the Vehicle-treated group in fluorescent double labeling experiment (FIG. 15d).

Figure 15E:
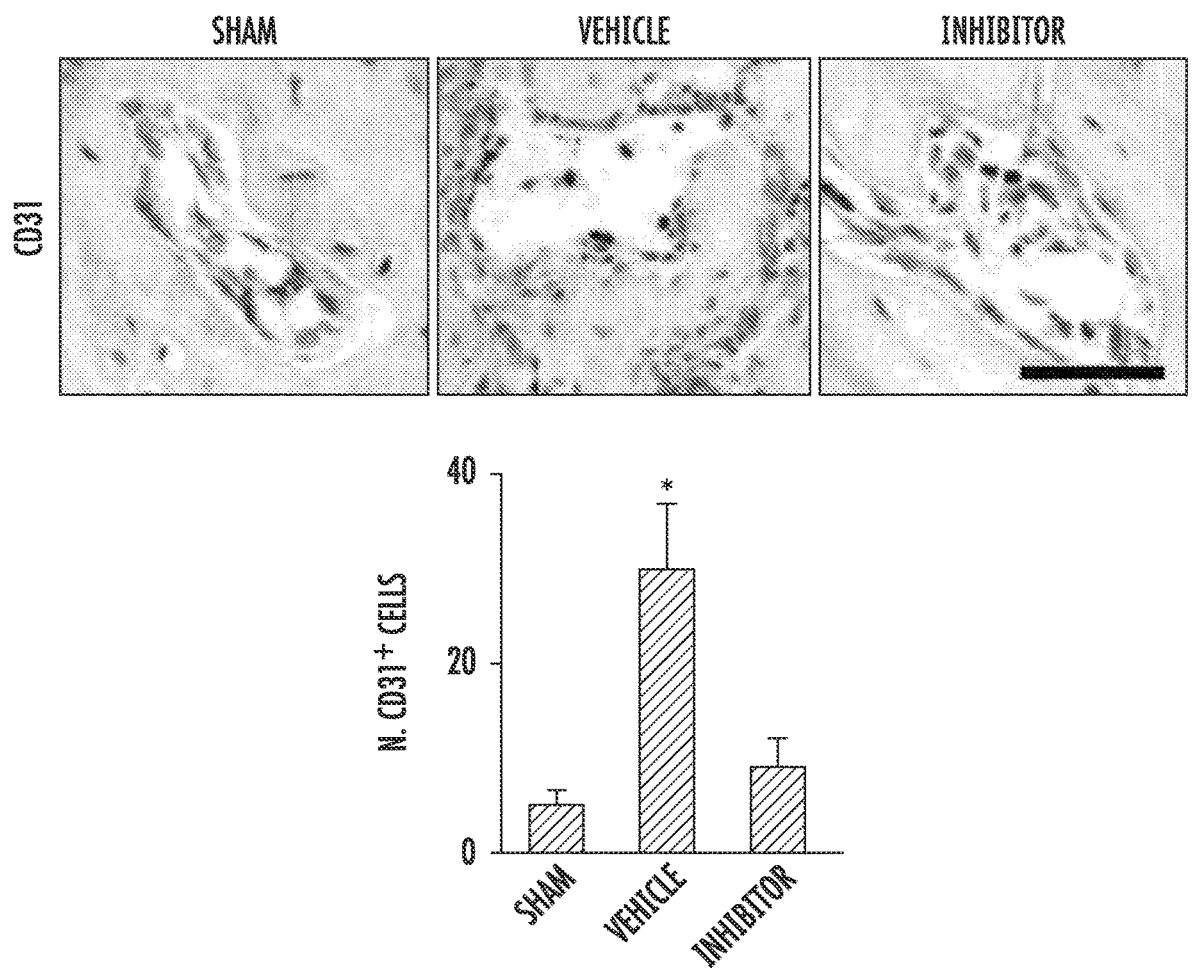
Figure 15F:
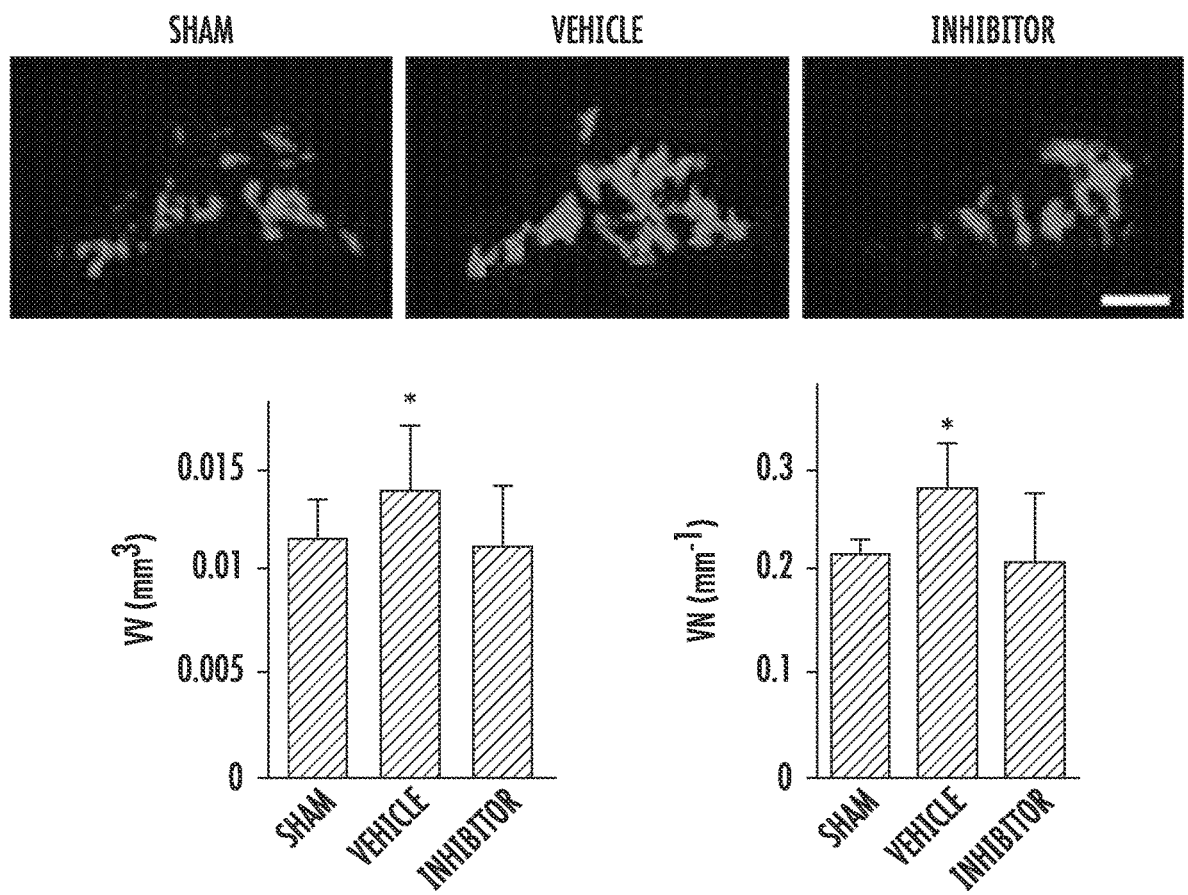
Figure 15G:
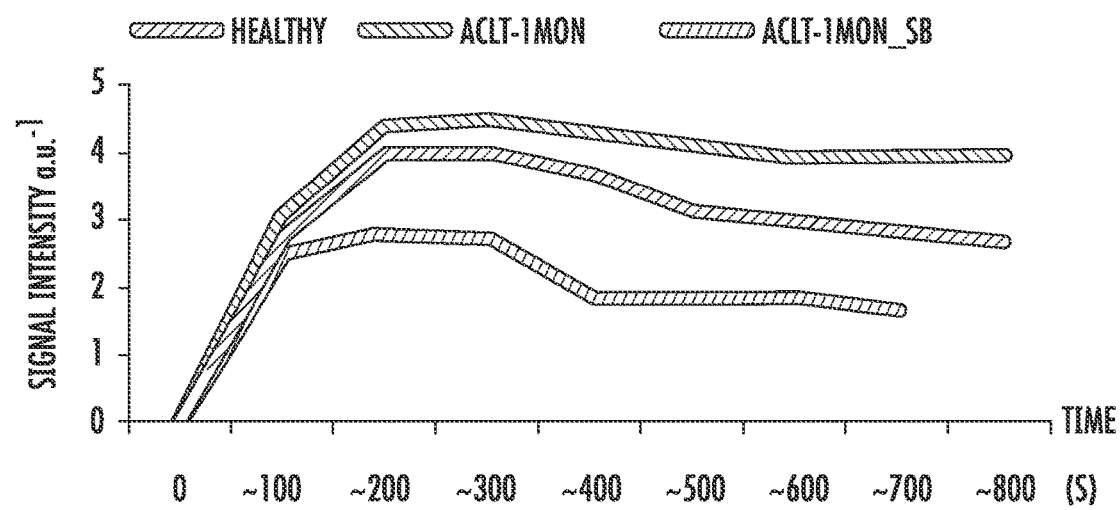
Figure 15H:
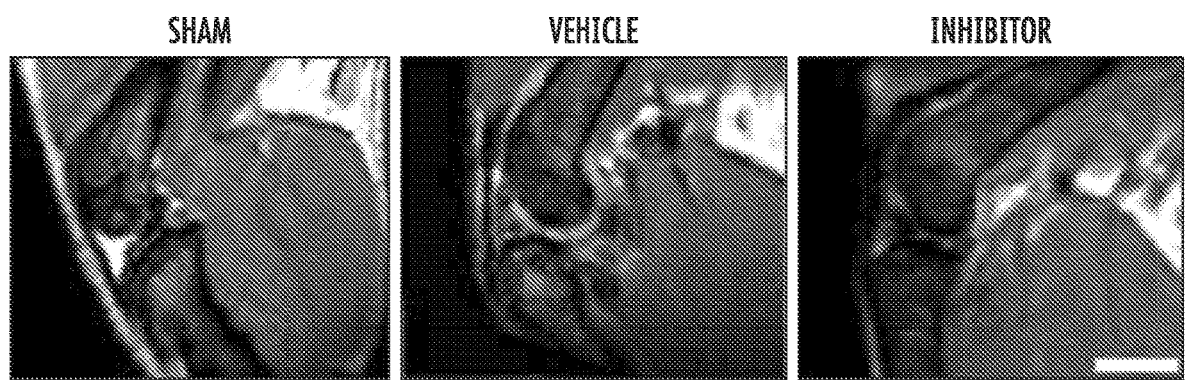

CD31$^+$ endothelial progenitors were significantly increased in the subchondral bone of ACLT mice relative to sham controls, which was reduced by injection of TβRI inhibitor. (FIG. 15e). Microfil contrast-enhanced angiography of subchondral bone confirmed that the inhibitor decreased angiogenesis (FIG. 15f), The contrast signal was significantly increased in vehicle treated mice at 1 month post ACLT in MRI perfusion analysis and the increase was prevented in the inhibitor treated group, indicating reduced new vessel formation (FIG. 15f). The bone marrow lesion in tibial subchondral bone detected by micro-MRI was also obviously smaller in size in the ACLT-inhibitor treated mice as compared to that of ACLT-vehicle treated mice (FIG. 15h). These results indicate that high concentrations of active TGF increased the number of nestin$^+$ MSCs, leading to osteoid islet formation in the subchondral bone marrow and angiogenesis, representing pathological changes of subchondral bone post ACLT. Dunkin Hartley guinea pigs develop spontaneous osteoarthritis. We observed subchondral bone marrow bone lesions in the knee joints. When the guinea pigs were injected with TGFβ type I receptor inhibitor for 3 months, the bone marrow lesions were significantly reduced (FIG. 16). Taken together, the osteoid islets in the subchondral bone marrow are associated the lesions visualized by MRI, which can be inhibited by TGFβ type I receptor inhibitor.

Discussion

TGF-β is known for its anabolic effects on articular cartilage homeostasis by stimulating the production of extracellular matrix proteins and preventing terminal differentiation of chondrocytes. In this study, we found that changes in mechanical loading on the joints increased the number of osteoclasts in the subchondral bone as early as 7 days post-surgery in the ACLT animal model. High concentrations of TGF-β1 were activated during osteoclast bone resorption to recruit nestin$^+$ MSCs for the subsequent uncoupled bone formation. Notably, osteoclastic bone resorption was spatiotemporally uncoupled with TGFβ1-induced recruitment of nestin MSCs and led to aberrant bone formation, which was further substantiated by development of osteoarthritic-like changes in CED mice. Relative to a single phase of uncoupled sequential bone resorption and formation in the mouse ACLT model, human osteoarthritis appeared more complex with multiple phases. We found some areas of the articular cartilage were still intact or in the middle stage of osteoarthritis progression when analyzing specimens from late stage osteoarthritis subjects who underwent knee joint replacement. Consistently, the thickness of the subchondral plate in osteoarthritis specimens is not uniform, although the percent distribution of subchondral plate generally became thicker (FIG. 7). Moreover, the concentrations of active TGF-β were higher in subchondral bone with articular cartilage compared that of the healthy controls. The observation suggests that inhibition of TGF-β activity in the subchondral bone may still have therapeutic effects even if individuals with osteoarthritis are not in the early stages. Our findings reveal that TGF-β plays a different role in subchondral bone as opposed to its anabolic effect on articular cartilage. Thus, the location of the elevated TGF-β1 concentrations in subchondral bone triggers a cascade of events that lead to the development of osteoarthritis.

Both clinical and animal studies report that progression of osteoarthritis is accompanied by the accumulation of mesenchymal progenitor cells in joint tissues and synovial fluids. Bone marrow lesions have been identified as a prognostic factor of osteoarthritis progression as it has been found to populate sites of cartilage destruction. We observed that elevations in TGF-β1 concentrations lead to an increased number of nestin+ MSCs in the subchondral bone marrow in various osteoarthritis animal models. During the normal remodeling process, osteoblasts and their progenitors are primarily observed at the resorption site on the bone surface. However, the altered microenvironment induced by abnormal mechanical loading may lead to "in situ" commitment of osteoprogenitors in the bone marrow cavities. Bone marrow lesions have been characterized as less well mineralized newly formed bone. These clustered bone marrow osteoprogenitors may lead to osteoid islets in the subchondral bone marrow that is visualized as bone marrow lesions under MRI. Moreover, knockout of TGFBR2 in nestin+ MSCs attenuated the development of osteoarthritis in ACLT mice. This result further confirmed our hypothesis that MSCs are the target cells of the aberrant TGF-β signals during osteoarthritis progression. Additionally, bone formation is often coupled with angiogenesis. It is known that the TGF-β signaling pathway in endothelial progenitor cells can promote angiogenesis and TGF-β may stimulate the paracrine machinery in MSCs that further facilitate angiogenesis. Our data revealed that blood vessels were increased in the subchondral bone of both ACLT and CED mice in angiography by microphil-perfused experiments. Reduced angiogenesis by inhibition of TGF-β activity may have further attenuated the de novo bone formation in the subchondral bone in the osteoarthritis joints of ACLT mice.

The subchondral bone and articular cartilage act as a functional unit in the joint. In human osteoarthritis joints, the subchondral plates become significantly thicker relative to that of healthy subjects. The subchondral bone was modeled post-surgery in ACLT animal models and their thickness dramatically fluctuated. The capacity of chondrocytes to modulate their functional state in response to alterations in mechanical loading is relatively limited compared to the adjacent subchondral bone. Changes in osteochondral junction are therefore likely involved in advancement of the calcified cartilage zone. The precise mechanism of degeneration of articular cartilage through abnormal subchondral bone changes is still unclear. In our established simulation model for human knee joints, expansion and increased stiffness of subchondral bone (FIG. 14) changed the distribution of articular cartilage stress. Therefore, TGF-β-induced abnormal bone formation may contribute to the alteration of the mechanical property of subchondral bone and initiate its expansion causing degeneration of articular cartilage.

I claim:

1. A method comprising the step of administering to a patient a transforming growth factor beta (TGF-beta) inhibitor, wherein the administering inhibits cartilage degeneration in the patient, wherein the inhibitor is administered into the subchondral bone area, wherein the TGF-beta inhibitor is a TGF-beta antibody or SB505124.

2. The method of claim 1, wherein the TGF beta is a member of the TGF-beta superfamily.

3. The method of claim 1, wherein the TGF-beta is TGF-beta 1, TGF-beta 2, TGF-beta 3.

4. The method of claim 1, wherein the TGF-beta is TGF-beta 1.

5. The method of claim 1, wherein the inhibitor inhibits active TGF-beta, a TGF-beta receptor, a protease responsible for activating a precursor TGF-beta into mature TGF-beta, expression of TGF-beta, or combinations of the foregoing.

6. The method of claim 1, wherein the cartilage degeneration is articular cartilage degeneration.

7. The method of claim 1, wherein the patient is suffering from osteoarthritis.

* * * * *